US008729272B2

(12) United States Patent
Dochnahl et al.

(10) Patent No.: US 8,729,272 B2
(45) Date of Patent: May 20, 2014

(54) PROCESS USING GRIGNARD REAGENTS

(75) Inventors: Maximilian Dochnahl, Mannheim (DE);
Michael Keil, Freinsheim (DE);
Joachim Gebhardt, Wachenheim (DE);
Uwe Josef Vogelbacher, Ludwigshafen (DE); Frederik Menges, Schriesheim (DE); Michael Rack, Eppelheim (DE);
Jens Renner, Dirmstein (DE); Bernd Wolf, Fussgoenheim (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 13/583,798

(22) PCT Filed: Mar. 15, 2011

(86) PCT No.: PCT/EP2011/053865
§ 371 (c)(1),
(2), (4) Date: Sep. 10, 2012

(87) PCT Pub. No.: WO2011/113820
PCT Pub. Date: Sep. 22, 2011

(65) Prior Publication Data
US 2013/0005985 A1    Jan. 3, 2013

Related U.S. Application Data

(60) Provisional application No. 61/314,185, filed on Mar. 16, 2010.

(30) Foreign Application Priority Data

Mar. 16, 2010  (EP) .................................... 10156601
Apr. 9, 2010   (EP) .................................... 10159510

(51) Int. Cl.
*C07D 405/06*   (2006.01)
*C07D 249/08*   (2006.01)
(52) U.S. Cl.
CPC ............ *C07D 249/08* (2013.01); *C07D 405/06* (2013.01)
USPC ..................................... 548/263.2; 548/266.6
(58) Field of Classification Search
None
See application file for complete search history.

(56) References Cited

U.S. PATENT DOCUMENTS

| 4,414,210 | A  | 11/1983 | Miller et al. |
| 4,723,042 | A  | 2/1988  | Janssen et al. |
| 4,804,785 | A  | 2/1989  | Janssen et al. |
| 4,898,954 | A  | 2/1990  | Mohrmann et al. |
| 5,162,357 | A  | 11/1992 | Seele et al. |
| 5,268,517 | A  | 12/1993 | Kober et al. |
| 5,639,918 | A  | 6/1997  | Hutt et al. |
| 5,859,039 | A  | 1/1999  | Jautelat et al. |
| 6,051,592 | A  | 4/2000  | Jautelat et al. |
| 6,057,353 | A  | 5/2000  | Jautelat et al. |
| 6,080,775 | A  | 6/2000  | Jautelat et al. |
| 6,114,368 | A  | 9/2000  | Jautelat et al. |
| 6,245,793 | B1 | 6/2001  | Hillebrand et al. |
| 6,245,794 | B1 | 6/2001  | Jautelat et al. |
| 6,274,610 | B1 | 8/2001  | Jautelat et al. |
| 6,329,411 | B1 | 12/2001 | Jautelat et al. |
| 6,369,044 | B1 | 4/2002  | Hillebrand et al. |
| 6,414,007 | B2 | 7/2002  | Hillebrand et al. |
| 6,420,406 | B1 | 7/2002  | Jautelat et al. |
| 6,586,415 | B2 | 7/2003  | Hillebrand et al. |
| 2010/0273651 | A1 | 10/2010 | Dietz et al. |
| 2010/0311581 | A1 | 12/2010 | Dietz et al. |
| 2010/0317515 | A1 | 12/2010 | Dietz et al. |
| 2011/0160056 | A1 | 6/2011  | Ulmschneider et al. |
| 2011/0172095 | A1 | 7/2011  | Dietz et al. |
| 2011/0172096 | A1 | 7/2011  | Ulmschneider et al. |
| 2011/0172097 | A1 | 7/2011  | Dietz et al. |
| 2011/0172098 | A1 | 7/2011  | Dietz et al. |
| 2011/0172099 | A1 | 7/2011  | Dietz et al. |
| 2011/0183842 | A1 | 7/2011  | Dietz et al. |
| 2011/0190122 | A1 | 8/2011  | Dietz et al. |

FOREIGN PATENT DOCUMENTS

| CA | 2011087     | 9/1990 |
| DE | 33 37 937   | 5/1984 |
| DE | 33 15 681   | 10/1984 |
| DE | 36 01 927   | 7/1987 |
| DE | 40 30 039   | 3/1992 |
| DE | 195 28 300  | 2/1997 |
| DE | 195 29 089  | 2/1997 |
| EP | 0 378 953   | 7/1990 |
| EP | 0 386 557   | 9/1990 |
| EP | 0 409 049   | 1/1991 |
| EP | 0 421 125   | 4/1991 |
| EP | 0 655 443   | 5/1995 |
| WO | WO 96/16048 | 5/1996 |
| WO | WO 96/38423 | 12/1996 |
| WO | WO 96/38440 | 12/1996 |
| WO | WO 96/41804 | 12/1996 |
| WO | WO 97/41107 | 11/1997 |
| WO | WO 97/42178 | 11/1997 |
| WO | WO 97/43269 | 11/1997 |
| WO | WO 97/44332 | 11/1997 |

(Continued)

OTHER PUBLICATIONS

Gestel et al., "Synthesis and Screening of a New Group of Fungicides: 1-(2- Phenyl-1,3-dioxolan-2-ylmethyl)-1,2,4-triazoles", Pestic. Sci. 1980, vol. 11, pp. 95-99.
Krasovskiy et al., "A LiCl-Mediated Br/Mg Exchange Reaction for the Preparation of Functionalized Aryl- and Heteroarylmagnesium Compounds from Organic Bromides", Angew. Chem. Int. Ed., 2004, vol. 43, pp. 3333-3336.
Krasovskiy et al., "Highly Efficient Reagents for Br/Mg Exchange", Angew. Chem. Int. Ed., 2006, vol. 45, pp. 159-162.
Research Disclosure, "Fungicidal mixtures of CGA 169374 with other fungicides for controlling cereal diseases", Jan. 1989, vol. 127, p. 13.
PCT/EP2011/053865, International Search Report, completed May 10, 2011.
PCT/EP2011/053865, International Preliminary Report on Patentability, issued Sep. 18, 2012.

*Primary Examiner* — Zinna Northington Davis
(74) *Attorney, Agent, or Firm* — Brinks Gilson & Lione

(57) ABSTRACT

The present invention relates to a process using Grignard reagents for providing thio-triazolo group-containing compounds.

15 Claims, No Drawings

(56) References Cited

FOREIGN PATENT DOCUMENTS

| | | |
|---|---|---|
| WO | WO 99/05149 | 2/1999 |
| WO | WO 99/21853 | 5/1999 |
| WO | WO 99/44331 | 9/1999 |
| WO | WO 2005/056548 | 6/2005 |
| WO | WO 2009/077443 | 6/2009 |
| WO | WO 2009/077471 | 6/2009 |
| WO | WO 2009/077497 | 6/2009 |
| WO | WO 2009/077500 | 6/2009 |
| WO | WO 2010/029000 | 3/2010 |
| WO | WO 2010/029001 | 3/2010 |
| WO | WO 2010/029002 | 3/2010 |
| WO | WO 2010/029003 | 3/2010 |
| WO | WO 2010/031721 | 3/2010 |
| WO | WO 2010/031842 | 3/2010 |
| WO | WO 2010/031847 | 3/2010 |
| WO | WO 2010/031848 | 3/2010 |
| WO | WO 2010/040717 | 4/2010 |
| WO | WO 2010/040718 | 4/2010 |
| WO | WO 2011/069894 | 6/2011 |
| WO | WO 2011/069912 | 6/2011 |
| WO | WO 2011/069916 | 6/2011 |
| WO | WO 2011/073145 | 6/2011 |
| ZA | 9604973 | 1/1997 |

PROCESS USING GRIGNARD REAGENTS

This application is a National Stage application of International Application No. PCT/EP2011/053865, filed Mar. 15, 2011, which claims the benefit of U.S. Provisional Application No. 61/314,185, filed Mar. 16, 2010, the entire contents of which are hereby incorporated herein by reference. This application also claims priority under 35 U.S.C. §119 to European Patent Application No. 10156601.6, filed Mar. 16, 2010, and European Patent Application No. 10159510.6, filed Apr. 9, 2010, the entire contents of which are hereby incorporated herein by reference.

The present invention relates to a process using Grignard reagents for providing thio-triazolo group-containing compounds, in particular pesticidal compounds of the triazole class having phytopathogenic activity, and for the synthesis of precursors therefor. The invention furthermore relates to intermediates and to their preparation.

Important pesticidal compounds carry a thio-triazolo group. Specific thio-triazole compounds that are known as active ingredients having pesticidal, in particular fungicidal activity, are known, for example, from WO 96/38440. Also WO 2009/077471 (PCT/EP2008/067483), WO 2009/077443 (PCT/EP2008/067394) WO 2009/077500 (PCT/EP2008/067545), WO 2009/077497 (PCT/EP2008/067539), EP 09178224 (PCT/EP2010/068848), EP 09178291 (PCT/EP2010/068853), EP09178288 (PCT/EP2010/068790) describe further specific thio-triazolo compounds. Therein, preparation routes for the disclosed compounds are explained.

In particular, it is known from the literature, for example, to introduce the thio-group into the respective triazole compounds using a strong base such as n-BuLi and sulfur powder. Alternatively, the triazole compounds are reacted with sulfur in the presence of an aprotic polar solvent, such as, for example, an amide (such as dimethylformamide (DMF)) or N-alkylpyrrolidone (such as N-octylpyrrolidone, N-dodecylpyrrolidone or N-methylpyrrolidone (NMP)). See also WO 99/19307, WO 97/06151, WO 97/05119 and WO 96/41804. The disadvantages of these methods are that the yields of the desired products are often not satisfying and that the reaction conditions often do not allow commercial scales. Regarding the reaction using n-BuLi, a further disadvantage is that the reagent is quite expensive and that the reaction has to be carried out at low temperatures, which necessitates special cooling equipment. Upscales are thus elaborate and expensive.

Consequently, the methods known from the literature are sometimes not suitable for the efficient synthesis of substituted thio-triazoles because the yield is not sufficient and/or the reaction conditions and parameters such as temperature and/or reactants are not suitable for an upscale to industrially relevant amounts. For example the reaction that involves strong bases often result in a high amount of side products and low yields of the desired products. Inter alia because some thio-triazolo compounds are promising fungicidally active compounds, there is an ongoing need for improved processes that easily make the thio-triazolo compounds available.

It has now surprisingly been found a highly efficient general synthesis for the introduction of sulfur into triazolo group-containing compounds involving the use of a Grignard reagent. The inventive process represents a new and general method for obtaining compounds containing a thio-triazolo-group. A key step in the process according to the invention is the deprotonation of the respective triazole compounds (IV) using a Grignard reagent, thereby resulting in the formation of a compound (IIIa) and/or (IIIb) (see below).

Accordingly, one aspect of the present invention is a process for the preparation of a compound (IIIa)

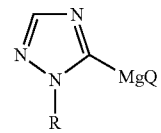

(IIIa)

comprising the step
(i) reacting a triazolo compound of formula (IV)

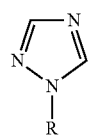

(IV)

with a Grignard reagent $R^1MgQ$ (V), wherein the variables are defined as follows:
R is an organic group;
Q is $R^1$ or X, wherein X is halogen; and
$R^1$ is $(C_1-C_{10})$-alkyl, $(C_2-C_{10})$-alkenyl, $(C_2-C_{10})$-alkynyl, $(C_3-C_8)$-cycloalkyl or $(C_6-C_{10})$-aryl, wherein the aryl is unsubstituted or substituted by one, two or three groups independently selected from the group consisting of halogen and $(C_1-C_4)$-alkyl.

Compound (IIIa) can be further reacted with a suitable electrophile to result directly in a target thio-triazolo-group-containing compound of formula (I)

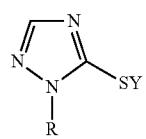

(I)

Alternatively, according to the invention, compound (IIIa) can be transformed into a magnesium thiolate (IIa)

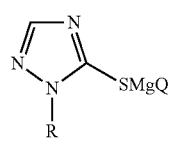

(IIa)

using sulfur. Intermediate (IIa) can further be reacted to a target compound (I) by protonating the magnesium thiolate (IIa) or by reacting the same with a suitable electrophilic compound.

Accordingly, the present invention provides a process for the preparation of a thio-triazolo group-containing compound of the formula (I), wherein the variables have the following meanings:
R is an organic group;
Y is hydrogen, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms from the group consisting of O, N and S, C(=S)R$^9$, SO$_2$R$^{10}$ or CN; wherein R$^9$ is NA$^3$A$^4$; wherein A$^3$,A$^4$ independently of one another are hydrogen, C$_1$-C$_8$-alkyl, C$_1$-C$_8$-haloalkyl, C$_2$-C$_8$-alkenyl, C$_2$-C$_8$-haloalkenyl, C$_2$-C$_8$-alkynyl, C$_2$-C$_8$-haloalkynyl, C$_3$-C$_8$-cycloalkyl, C$_3$-C$_8$-halocycloalkyl, C$_3$-C$_8$-cycloalkenyl, C$_3$-C$_8$-halocycloalkenyl, (C$_6$-C$_{10}$)-aryl, a five-, six-, seven-, eight-, nine- or ten-membered aromatic heterocycle that contains one, two, three or four heteroatoms from the group consisting of O, N and S;

R$^{10}$ is (C$_1$-C$_8$)-alkyl, phenyl-(C$_1$-C$_8$)-alkyl or phenyl, where the phenyl groups are in each case unsubstituted or substituted by one, two or three groups independently selected from the group consisting of halogen and (C$_1$-C$_4$)-alkyl.

Another aspect of the present invention is a compound of formula (IIIa) and (IIIb) (see below) and the synthesis and use thereof. Still another aspect of the present invention is a compound of formula (IIa) and the synthesis and use thereof. Furthermore, the present invention also relates to the use of a Grignard reagent R$^1$MgQ (V), as defined and preferably defined herein, for the synthesis of a thio-triazolo group-containing compound of the formula (I) as defined in detail herein, including the specific and/or preferred embodiments thereof.

The thio-triazolo groups of the general formula (I) can be present in two tautomeric forms (especially, in case "Y" is hydrogen)—the "thiol" form of the formula (Ia) or in the "thiono" form of the formula (Ib)

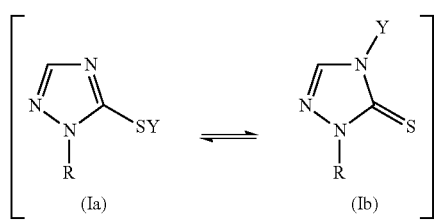

(I)

However, for the sake of simplicity, generally only one of the two forms, mostly the "thiol" form is shown here.

In some of the definitions of the symbols in the formulae given herein, collective terms are used which are generally representative of the following substituents:

halogen: fluorine, chlorine, bromine and iodine;

alkyl and the alkyl moieties of composite groups such as, for example, alkylamino:

saturated straight-chain or branched hydrocarbon radicals having 1 to 4, 6, 8 or 12 carbon atoms, for example C$_1$-C$_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methyl pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: alkyl as mentioned above, where some or all of the hydrogen atoms in these groups are replaced by halogen atoms as mentioned above; in particular C$_1$-C$_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl alkenyl and also the alkenyl moieties in composite groups, such as alkenyloxy:

unsaturated straight-chain or branched hydrocarbon radicals having 2 to 4, 2 to 6 or 2 to 8 carbon atoms and one double bond in any position. According to the invention, it may be preferred to use small alkenyl groups, such as (C$_2$-C$_4$)-alkenyl; on the other hand, it may also be preferred to employ larger alkenyl groups, such as (C$_5$-C$_8$)-alkenyl. Examples of alkenyl groups are, for example, C$_2$-C$_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

haloalkenyl: alkenyl as defined above, where some or all of the hydrogen atoms in these groups are replaced by halogen atoms as described above under haloalkyl, in particular by fluorine, chlorine or bromine;

alkadienyl: unsaturated straight-chain or branched hydrocarbon radicals having 4 to 6 or 4 to 8 carbon atoms and two double bonds in any position;

alkynyl and the alkynyl moieties in composite groups: straight-chain or branched hydrocarbon groups having 2 to 4, 2 to 6 or 2 to 8 carbon atoms and one or two triple bonds in any position, for example C$_2$-C$_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

haloalkynyl: alkynyl as defined above, where some or all of the hydrogen atoms in these groups are replaced by halogen atoms as described above under haloalkyl, in particular by fluorine, chlorine or bromine;

cycloalkyl and also the cycloalkyl moieties in composite groups: mono- or bicyclic saturated hydrocarbon groups having 3 to 8, in particular 3 to 6, carbon ring members, for example $C_3$-$C_6$-cycloalkyl, such as cyclopropyl, cyclobutyl, cyclopentyl, cyclohexyl;

halocycloalkyl: cycloalkyl as defined above, where some or all of the hydrogen atoms in these groups are replaced by halogen atoms as described above under haloalkyl, in particular by fluorine, chlorine or bromine;

cycloalkenyl: monocyclic monounsaturated hydrocarbon groups having preferably 3 to 8 or 4 to 6, in particular 5 to 6, carbon ring members, such as cyclopenten-1-yl, cyclopenten-3-yl, cyclohexen-1-yl, cyclohexen-3-yl, cyclohexen-4-yl and the like;

halocycloalkenyl: cycloalkenyl as defined above, where some or all of the hydrogen atoms in these groups are replaced by halogen atoms as described above under haloalkyl, in particular by fluorine, chlorine or bromine;

alkoxy: an alkyl group as defined above which is attached via an oxygen, preferably having 1 to 8, more preferably 2 to 6, carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy.

alkylene: divalent unbranched chains of $CH_2$ groups. Preference is given to ($C_1$-$C_6$)-alkylene, more preference to ($C_2$-$C_4$)-alkylene; furthermore, it may be preferred to use ($C_1$-$C_3$)-alkylene groups. Examples of preferred alkylene radicals are $CH_2$, $CH_2CH_2$, $CH_2CH_2CH_2$, $CH_2(CH_2)_2CH_2$, $CH_2(CH_2)_3CH_2$ and $CH_2(CH_2)_4CH_2$;

a 3-, 4-, 5-, 6-, 7-, 8-, 9- or 10-membered saturated or partially unsaturated heterocycle which contains 1, 2, 3 or 4 heteroatoms from the group consisting of O, N and S, where the heterocycle in question may be attached via a carbon atom or, if present, via a nitrogen atom. According to the invention, it may be preferred for the heterocycle in question to be attached via carbon, on the other hand, it may also be preferred for the heterocycle to be attached via nitrogen. In particular:

a three- or four-membered saturated heterocycle (hereinbelow also referred to as heterocyclyl) which contains one or two heteroatoms from the group consisting of O, N and S as ring members;

a five- or six-membered saturated or partially unsaturated heterocycle which contains one, two, three or four heteroatoms from the group consisting of O, N and S as ring members: for example monocyclic saturated or partially unsaturated heterocycles which, in addition to carbon ring members, contain one, two or three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the correspondingylidene radicals;

a seven-membered saturated or partially unsaturated heterocycle which contains one, two, three or four heteroatoms from the group consisting of O, N and S as ring members: for example mono- and bicyclic heterocycles having 7 ring members which, in addition to carbon ring members, contain one, two or three nitrogen atoms and/or one oxygen or sulfur atom or one or two oxygen and/or sulfur atoms, for example tetra- and hexahydroazepinyl, such as 2,3,4,5-tetrahydro[1H]azepin-1-,-

2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding ylidene radicals;

a 5-, 6-, 7-, 8-, 9- or 10-membered aromatic heterocycle which contains 1, 2, 3 or 4 heteroatoms from the group consisting of O, N and S: in particular a five- or six-membered aromatic mono- or bicyclic heterocycle which contains one, two, three or four heteroatoms from the group consisting of O, N and S: the heterocycle in question may be attached via a carbon atom or, if present, via a nitrogen atom. According to the invention, it may be preferred for the heterocycle in question to be attached via carbon, on the other hand, it may also be preferred for the heterocycle to be attached via nitrogen. The heterocycle is in particular:

5-membered heteroaryl which contains one, two, three or four nitrogen atoms or one, two or three nitrogen atoms and/or one sulfur or oxygen atom, where the heteroaryl may be attached via carbon or nitrogen, if present: 5-membered heteroaryl groups which, in addition to carbon atoms, may contain one to four nitrogen atoms or one, two or three nitrogen atoms and/or one sulfur or oxygen atom as ring members, for example furyl, thienyl, pyrrolyl, pyrazolyl, imidazolyl, triazolyl (1,2,3-; 1,2,4-triazolyl), tetrazolyl, oxazolyl, isoxazolyl, 1,3,4-oxadiazolyl, thiazolyl, isothiazolyl and thiadiazolyl, in particular 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl which contains one, two, three or four, preferably one, two or three, nitrogen atoms, where the heteroaryl may be attached via carbon or nitrogen, if present: 6-ring heteroaryl groups which, in addition to carbon atoms, may contain one to four or one, two or three nitrogen atoms as ring members, for example pyridinyl, pyrimidinyl, pyrazinyl, pyridazinyl, 1,2,3-triazinyl, 1,2,4-triazinyl, 1,3,5-triazinyl, in particular 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The finding of the present invention is that, ultimately, it offers a very general method for introducing sulfur into triazole groups. Therefore, R in principle can be any organic group that allows carrying out the reaction steps according to the inventive process ultimately resulting in thio-group-containing triazole groups. If necessary, some reactive groups within the "organic group" can be protected via suitable protecting groups. It is within the skill of a person of the art to choose suitable groups and it is general knowledge of the skilled person how to insert and remove such groups.

Important pesticidal compounds carry a thio-triazolo group. In particular, there are compounds of formula (I) known that are effective against phytopathogenic fungi. According to one aspect of the present invention, compounds of formula (I) are active compounds for controlling phytopathogenic fungi. Thus, compounds that can advantageously be synthesized using the new inventive process are for example fungicidal compounds of the triazole compound class.

For example, the inventive process has shown to be very useful for the synthesis of fungicidal thio-triazole compounds of the triazole compound class that contain an epoxide group. Compounds that contain labile functional groups such as an epoxide group can often not be efficiently and/or economically be synthesized via prior art processes. Such compounds are for example described in WO 96/38440, WO 2009/077471 (PCT/EP2008/067483), WO 2009/077443 (PCT/EP2008/067394) WO 2009/077500 (PCT/EP2008/067545) and WO 2009/077497 (PCT/EP2008/067539), EP 09178224 (PCT/EP2010/068848), EP 09178291 (PCT/EP2010/068853) and EP09178288 (PCT/EP2010/068790), wherein these documents also describe the fungicidal activity of said compounds. In said patent applications, also the respective triazole compounds (without sulfur group) and their synthesis are disclosed.

In the following, the meaning of the substituents of the compounds used according to the invention is further defined. Thereby, in each case the substituents are meant to have the given meanings and preferred meaning on their own or in any combination with the meanings or preferred meanings of any other substituent.

Accordingly, in one aspect of the inventive process, R in the compounds (I) and the precursors thereof, in particular in compounds (IV), has the following meaning (1):

wherein # shall mean the point of attachment to the triazolo group and A and B are as defined as follows:

A or B is a three-, four-, five-, six-, seven-, eight-, nine- or ten-membered saturated or partially unsaturated heterocycle or five-, six-, seven-, eight-, nine- or ten-membered aromatic heterocycle, where the heterocycle contains in each case one, two, three or four heteroatoms from the group consisting of O, N and S; is naphthyl or phenyl;

and the respective other variable B or A has
one of the meanings mentioned above for A or B or is $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, naphthyl or benzodioxolyl;

where A and/or B independently of one another are unsubstituted or substituted by one, two, three or four independently selected substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_n A^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5, A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino.

In group (1) particular preference is given to the following meanings of the substituents, in each case on their own or in combination.

According to one embodiment, A and B independently stand for unsubstituted phenyl or substituted phenyl containing one, two, three or four independently selected substituents L.

According to one specific embodiment, A is unsubstituted phenyl.

According to a further embodiment, A is phenyl, containing one, two, three or four, in particular one or two, independently selected substituents L, wherein L is as defined or as preferably defined herein. According to one aspect of this embodiment, one of the substituents is in 4-position (para) of the phenyl ring. According to a further aspect, L is in each case independently selected from F, Cl, Br, nitro, phenyl, phenoxy, methyl, ethyl, iso-propyl, tert-butyl, methoxy, ethoxy, trifluoromethyl, trichloromethyl, difluoromethyl, difluorochloromethyl, trifluoromethoxy, difluoromethoxy and trifluorochloromethyl. According to another specific aspect, L is in each case independently selected from F, Cl and Br, in particular F and Cl.

According to another embodiment, A is monosubstituted phenyl, containing one substituent L, wherein L is as defined or as preferably defined herein. According to one aspect, said substituent is in para-position.

According to a specific embodiment, A is 3-fluorophenyl.

According to another embodiment, A is phenyl, containing two or three independently selected substituents L.

According to another preferred embodiment of the invention, A is phenyl which is substituted by one F and contains a further substituent L, where the phenyl may additionally contain one or two substituents L selected independently of one another, wherein L is as defined or preferably defined herein. According to a preferred embodiment, A is a group A-1

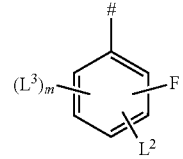

A-1 in which # is the point of attachment of the phenyl ring to the oxirane ring; and $L^2$ is selected from the group consisting of F, Cl, $NO_2$, phenyl, halogenphenyl, phenoxy, halogenphenoxy, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio;

$L^3$ is independently selected from the group consisting of F, Cl, Br, $NO_2$, phenyl, halogenphenyl, phenoxy, halogenphenoxy, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio; and m is 0, 1 or 2.

In one embodiment, $L^2$ is selected from the group consisting of F, Cl, methyl, methoxy, $CF_3$, $CHF_2$, $OCF_3$, $OCF_3$ and $OCHF_2$. According to a more specific embodiment, $L^2$ is F or Cl.

In one embodiment, $L^3$ is independently selected from the group consisting of F, Cl, methyl, methoxy, $CF_3$, $CHF_2$, $OCF_3$, $OCF_3$ or $OCHF_2$. According to a more specific embodiment, $L^3$ is independently F or Cl.

According to a preferred embodiment, m=0. According to a further preferred embodiment, m=1.

In the formula A-1, the fluorine substituent is, according to a preferred embodiment, in the 4-position.

According to still another embodiment, A is disubstituted phenyl, containing exactly two substituents L that are independently selected from each other, wherein L is as defined or as preferably defined herein. In particular, L is in each case independently selected from F, Cl, Br, $C_1$-$C_4$-alkyl, $C_1$-$C_4$-haloalkyl and $C_1$-$C_4$-alkoxy, in particular selected from F, Cl, $C_1$-$C_4$-alkyl, $C_1$-$C_4$-haloalkyl and $C_1$-$C_4$-alkoxy, in particular selected from F, Cl, methyl, trifluoromethyl and methoxy. According to a further aspect of this embodiment, the second substituent L is selected from methyl, methoxy and chloro. According to another aspect, one of the substituents is in the 4-position of the phenyl ring. According to another specific aspect, A is phenyl containing one F and exactly one further substituent L as defined or preferably defined herein.

According to yet a further preferred embodiment, A is disubstituted phenyl which contains one F and a further substituent L selected from the group consisting of Cl, $C_1$-$C_4$-alkyl, $C_1$-$C_4$-haloalkyl and $C_1$-$C_4$-alkoxy, in particular selected from the group consisting of Cl, methyl, trifluoromethyl and methoxy. The second substituent L is specifically selected from the group consisting of methyl, methoxy and chlorine. According to one aspect thereof, one of the substituents is located in the 4-position of the phenyl ring.

According to another specific embodiment, A is 2,4-disubstituted phenyl. According to still another specific embodiment, A is 2,3-disubstituted phenyl. According to still another specific embodiment, A is 2,5-disubstituted phenyl. According to still another specific embodiment, A is 2,6-disubstituted phenyl. According to still another specific embodiment, A is 3,4-disubstituted phenyl. According to still another specific embodiment, A is 3,5-disubstituted phenyl.

According to a further preferred embodiment of the invention, A is phenyl which is substituted by exactly two F. According to one aspect, A is 2,3-difluoro-substituted. According to a further aspect, A is 2,4-difluoro-substituted. According to yet a further aspect, A is 2,5-difluoro-substituted. According to yet a further aspect, A is 2,6-difluoro-substituted. According to yet a further aspect, A is 3,4-difluoro-substituted. According to yet a further aspect, A is 3,5-difluoro-substituted.

According to a further embodiment, A is trisubstituted phenyl containing exactly three independently selected substitutents L, wherein L is as defined or preferably defined herein. According to yet a further embodiment, A is phenyl which is substituted by exactly three F. According to one aspect, A is 2,3,4-trisubstituted, in particular 2,3,4-trifluoro-substituted. According to another aspect, A is 2,3,5-trisubstituted, in particular 2,3,5-trifluoro-substituted. According to still another aspect, A is 2,3,6-trisubstituted, in particular 2,3,6-trifluoro-substituted. According to still another aspect, A is 2,4,6-trisubstituted, in particular 2,4,6-trifluoro-substituted. According to still another aspect, A is 3,4,5-trisubstituted, in particular 3,4,5-trifluoro-substituted. According to still another aspect, A is 2,4,5-trisubstituted, in particular 2,4,5-trifluoro-substituted.

According to a preferred embodiment, B is phenyl, that is unsubstituted or phenyl which contains one, two, three or four independently selected substituents L, wherein L is as defined or preferably defined herein.

According to one embodiment of the invention, B is unsubstituted phenyl.

According to a further embodiment, B is phenyl which contains one, two, three or four independently selected substituents L, wherein L is as defined or preferably defined herein.

According to a further embodiment, B is phenyl which contains one, two or three, preferably one or two, independently selected substituents L, wherein L is as defined or preferably defined herein. According to a specific aspect, L is in each case independently selected from F, Cl, Br, methyl, methoxy and trifluoromethyl. According to still another embodiment, B is phenyl, which contains one, two or three, preferably, one or two, halogen substituents.

According to a further embodiment, B is phenyl which contains one, two, three or four substituents L, wherein L is independently selected from F, Cl, Br, methyl, ethyl, isopropyl, tert-butyl, methoxy, ethoxy, trifluoromethyl, trichloromethyl, difluoromethyl, difluorochloromethyl, trifluoromethoxy, difluoromethoxy and difluorochloromethyl. According to a specific aspect, L is in each case independently selected from F, Cl and Br.

According to still a further embodiment, B is unsubstituted phenyl or phenyl which contains one, two or three substituents independently selected from halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio and $C_1$-$C_4$-alkylthio.

According to a further embodiment, B is a phenyl ring that is monosubstituted by one substituent L, where according to a special aspect of this embodiment, L is located in the ortho-position to the point of attachment of the phenyl ring to the oxirane ring. L is as defined or preferably defined herein. According to a further specific embodiment, B is monochloro-substituted phenyl, in particular 2-chlorophenyl.

According to a further embodiment, B is phenyl, which contains two or three, in particular two, independently selected substitutents L, wherein L is as defined or preferably defined herein.

According to a further embodiment of the invention, B is a phenyl ring which contains a substituent L in the ortho-position and furthermore has one further independently selected substituent L. According to one aspect, the phenyl ring is 2,3-disubstituted. According to a further aspect, the phenyl ring is 2,4-disubstituted. According to yet a further aspect, the phenyl ring is 2,5-disubstituted. According to yet a further aspect, the phenyl ring is 2,6-disubstituted.

According to a further embodiment of the invention, B is a phenyl ring which contains a substituent L in the ortho-position and furthermore contains two further independently selected substituents L. According to one aspect, the phenyl ring is 2,3,5-trisubstituted. According to a further aspect, the phenyl ring is 2,3,4-trisubstituted. According to yet a further aspect, the phenyl ring is 2,4,5-trisubstituted.

In a further embodiment, B is phenyl which contains one substituent L in the 2-position and one, two or three further independently selected substituents L. According to a preferred embodiment, B is a group B-1

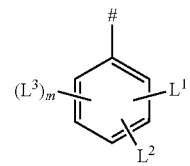

B-1 in which # denotes the point of attachment of the phenyl ring to the oxirane ring; and $L^1$ is selected from the group consisting of halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio, preferably selected from the group consisting of F, Cl, methyl, ethyl, methoxy, ethoxy, $CF_3$, $CHF_2$, $OCF_3$, $OCHF_2$ and $SCF_3$;

$L^2$ is selected from the group consisting of halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio, preferably selected from the group consisting of F, Cl, methyl, ethyl, methoxy, ethoxy, $CF_3$, $CHF_2$, $OCF_3$, $OCHF_2$ and $SCF_3$;

$L^3$ is independently selected from the group consisting of halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio, preferably selected from the group consisting of F, Cl, methyl, ethyl, methoxy, ethoxy, $CF_3$, $CHF_2$, $OCF_3$, $OCHF_2$ and $SCF_3$; and m is 0, 1 or 2.

According to a preferred embodiment, $L^1$ is F. According to another preferred embodiment, $L^1$ is Cl. According to a further preferred embodiment, $L^1$ is methyl. According to yet a further preferred embodiment, $L^1$ is methoxy. According to yet a further preferred embodiment, $L^1$ is $CF_3$. According to yet a further preferred embodiment, $L^1$ is $OCF_3$ or $OCHF_2$. According to a preferred embodiment, in the compounds of the formula I according to the invention, B is thus phenyl which contains a substituent selected from the group consisting of F, Cl, $CH_3$, $OCH_3$, $CF_3$, $CHF_2$, $OCF_3$ and $OCHF_2$ in the 2-position and one or two further independently selected substituents L.

According to a further preferred embodiment, $L^2$ is F. According to another preferred embodiment, $L^2$ is Cl.

According to a further preferred embodiment, $L^2$ is methyl. According to yet a further preferred embodiment, $L^2$ is methoxy. According to yet a further preferred embodiment, $L^2$ is $CF_3$. According to yet a further preferred embodiment, $L^2$ is $OCF_3$ or $OCHF_2$.

According to a preferred embodiment, $L^3$ is F. According to another preferred embodiment, $L^3$ is Cl. According to a further preferred embodiment, $L^3$ is methyl. According to yet a further preferred embodiment, $L^3$ is methoxy. According to yet a further preferred embodiment, $L^3$ is $CF_3$. According to yet a further preferred embodiment, $L^3$ is $OCF_3$ or $OCHF_2$.

According to a preferred embodiment, m=0; i.e. B is a disubstituted phenyl ring. According to a preferred aspect, B is a 2,3-disubstituted phenyl ring. According to a further preferred aspect, the phenyl ring B is 2,4-disubstituted. According to yet a further preferred aspect, the phenyl ring B is 2,5-disubstituted. According to yet a further preferred aspect, the phenyl ring is 2,6-disubstituted.

According to a further preferred embodiment, m=1; i.e. B is a trisubstituted phenyl ring. According to a preferred aspect, the phenyl ring B is 2,3,5-trisubstituted. According to another preferred further aspect, the phenyl ring B is 2,3,4-trisubstituted. According to yet a further preferred embodiment, the phenyl ring B is 2,4,5-trisubstituted.

Unless indicated otherwise, in group (1) L independently has the following preferred meanings:

According to one embodiment, L is independently selected from the group consisting of halogen, cyano, nitro, cyanato (OCN), $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl, S-$A^1$, C(=O)$A^2$, C(=S)$A^2$, $NA^3A$;

where $A^1$, $A^2$, $A^5$, $A^6$ are as defined below:
  $A^1$ is hydrogen, hydroxy, $C_1$-$C_4$-alkyl, $C_1$-$C_4$-haloalkyl;
  $A^2$ is one of the groups mentioned under $A^1$ or $C_1$-$C_4$-alkoxy, $C_1$-$C_4$-haloalkoxy, $C_3$-$C_6$-cycloalkyl, $C_3$-$C_6$-halocycloalkyl, $C_3$-$C_6$-cycloalkoxy or $C_3$-$C_6$-halocycloalkoxy;
  $A^5$,$A^6$ independently of one another are hydrogen, $C_1$-$C_4$-alkyl, $C_1$-$C_4$-haloalkyl;
  where the aliphatic and/or alicyclic groups of the radical definitions of L for their part may carry one, two, three or four identical or different groups $R^L$:
  $R^L$ is halogen, cyano, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl, amino, $C_1$-$C_8$-alkylamino, di-$C_1$-$C_8$-alkylamino.

Furthermore preferably, L is independently selected from the group consisting of halogen, $NO_2$, amino, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylamino, di-$C_1$-$C_4$-alkylamino, thio and $C_1$-$C_4$-alkylthio.

Furthermore preferably, L is independently selected from the group consisting of halogen, $C_1$-$C_4$-alkyl, $C_1$-$C_4$-haloalkyl, $C_1$-$C_4$-alkoxy, $C_1$-$C_4$-haloalkoxy and $C_1$-$C_4$-haloalkylthio, in particular halogen, $C_1$-$C_4$-alkyl and $C_1$-$C_4$-haloalkyl.

According to a further preferred embodiment, L is independently selected from the group consisting of F, Cl, Br, $CH_3$, $C_2H_5$, i-$C_3H_7$, t-$C_4H_9$, $OCH_3$, $OC_2H_5$, $CF_3$, $CCl_3$, $CHF_2$, $CClF_2$, $OCF_3$, $OCHF_2$ and $SCF_3$, in particular selected from the group consisting of F, Cl, $CH_3$, $C_2H_5$, $OCH_3$, $OC_2H_5$, $CF_3$, $CHF_2$, $OCF_3$, $OCHF_2$ and $SCF_3$. According to one aspect, L is independently selected from the group consisting of F, Cl, $CH_3$, $OCH_3$, $CF_3$, $OCF_3$ and $OCHF_2$. It may be preferred for L to be independently F or Cl.

According to one preferred embodiment, A and B are as defined as follows:

A phenyl, which is unsubstituted or substituted by one, two or three substituents L that may be the same or different, independently selected from F, Cl, Br, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio; and B phenyl, that is substituted by one, two or three substituents L that may be the same or different, independently selected from F, Cl, Br, methyl, ethyl, iso-propyl, tert-butyl, methoxy, ethoxy, trifluoromethyl, trichloromethyl, difluoromethyl, difluorochloromethyl, trifluoromethoxy, difluoromethoxy and trifluoromethylthio.

In specific groups (1) A and B are defined as follows:

A is phenyl, 4-chlorophenyl, 2,4-chlorophenyl, 2-chlorophenyl, 2-fluorophenyl, 4-fluorophenyl, 4-methylphenyl, 3-bromo-4-fluorophenyl, 4-bromophenyl, 3,4-dichlorophenyl, 4-tert-butyl-phenyl, 3-chlorophenyl, 3,5-dichlorophenyl or 4-trifluoromethoxyphenyl and B is 2-chlorophenyl. In one specific group (1) A is 4-fluorphenyl and B is 2-chlorophenyl.

A is 4-fluorophenyl and B is 2-difluoromethoxyphenyl.

A is phenyl, 4-chlorophenyl, 2,4-chlorophenyl, 2-chlorophenyl, 2-fluorophenyl, 4-methylphenyl, 4-fluorophenyl, 3-bromo-4-fluorophenyl, 4-bromophenyl, 3,4-dichlorophenyl, 4-tert-butyl-phenyl, 3-chlorophenyl, 3,5-dichlorophenyl or 4-trifluoromethoxyphenyl, and B is 2-fluorophenyl.

A is phenyl, 4-chlorophenyl, 2,4-chlorophenyl, 2-chlorophenyl, 2-fluorophenyl, 4-methylphenyl, 4-fluorophenyl, 3-bromo-4-fluorophenyl, 4-bromophenyl, 3,4-dichlorophenyl, 4-tert-butyl-phenyl, 3-chlorophenyl, 3,5-dichlorophenyl or 4-trifluoromethoxyphenyl, and B is 2-bromophenyl.

In further specific groups (1) A and B are defined as follows:

A is 2,4-difluorophenyl and B is 2-chlorophenyl.

A is 3,4-difluorophenyl and B is 2-chlorophenyl.

A is 2,4-difluorophenyl and B is 2-fluorophenyl.

A is 3,4-difluorophenyl and B is 2-fluorophenyl.

A is 2,4-difluorophenyl and B is 2-trifluoromethylphenyl.

A is 3,4-difluorophenyl and B is 2-trifluoromethylphenyl.

A is 3,4-difluorophenyl and B is 2-methylphenyl

In further specific groups (1) A and B are defined as follows:

A is phenyl and B is 2,4-dichlorophenyl.

A is phenyl and B is 2-fluoro-3-chlorophenyl.

A is phenyl and B is 2,3,4-trichlorophenyl.

A is 4-fluorophenyl and B is 2,4-dichlorophenyl.

A is 4-fluorophenyl and B is 2-fluoro-3-chlorophenyl.

A is 4-fluorophenyl and B is 2,3,4-trichlorophenyl.

A is 2-chlorophenyl and B is 2,4-dichlorophenyl.

A is 2-chlorophenyl and B is 2-fluoro-3-chlorophenyl.

A is 2-chlorophenyl and B is 2,3,4-trichlorophenyl.

The meanings described above of the variables A, B and L for groups (1) apply for R=group (1) in compounds (I) and, unless indicated otherwise, correspondingly to the precursors of the compounds (I) and side products.

The precursors for compounds (I)-(1), such as the respective compounds (IV)-(1) can be synthesized as described in the above mentioned patent applications.

The compounds (IV)-(1) can be prepared in an advantageous manner from compounds of the formula (XI)

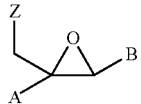
(XI)

in which Z is a leaving group, such as, for example, halogen (for example Cl or Br) or $OSO_2R$, where R is $C_1$-$C_6$-alkyl, $C_1$-$C_6$-haloalkyl, aryl or substituted aryl; $OSO_2R$ is in particular a mesylate, triflate, phenyl or toluenesulfonate group. To obtain compounds of the formula (IV)-(1), compounds of the formula (XI), are reacted with 1,2,4-triazole and a base such as, for example, sodium hydride, for example in DMF. See also, for example, EP 0 421 125 A2.

Compounds of the formula (XI) can be obtained from compounds (XI), wherein Z is a hydroxy group by introducing the leaving group Z by methods known to the person skilled in the art. Thus, the respective hydroxy compound is reacted, for example, with R—$SO_2Y$, where R is as defined for formula (XI) and Y is halogen, where R—$SO_2Y$ is, for example, mesyl chloride, in the presence of a base (for example $NEt_3$) (see also EP386557). To obtain compounds (XI), in which Z is halogen, the corresponding hydroxy compound can be reacted with $C(Hal)_4$ (Hal=Br or Cl) with $PPh_3$, for example in $CH_2Cl_2$. Alternatively, $SOCl_2$/pyridine can be used (see also WO 2005/056548). The hydroxy compounds of the formula (XI) (Z=OH) can be obtained from α,β-disubstituted enals of the type of the formula

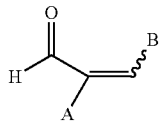

by initial epoxidation, for example with $H_2O_2$ or tert-butyl hydroperoxide, in the presence of a base such as, for example, NaOH or by reaction with a peracid (for example MCPBA=m-chloroperoxybenzoic acid). The resulting aldehyde can then be reduced to the hydroxy compound, for example with $NaBH_4$ (see also EP 0 386 557A1). Processes for epoxidation and reduction of the aldehyde group are well known to the person skilled in the art. The double bond can be present either in the (E) or in the (Z) configuration. This is indicated by the zig-zag bond between B and the double bond. The acrolein compounds can be synthesized, for example, analogously to the procedure described in DE3601927. According to one alternative, they can be prepared via an aldol synthesis according to the scheme below:

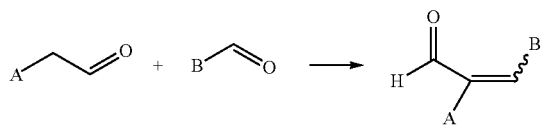

Another way to prepare the compounds (XI) consists in converting the double bond in compounds of the formula

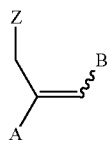

to the epoxide. Suitable epoxidation methods are known to the person skilled in the art. It is possible, for example, to use hydrogen peroxide/maleic anhydride for this purpose. The double bond may be present either in (E) or in (Z) configuration. This is indicated by the zigzag bond between B and the double bond. These compounds can be

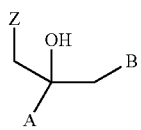

by reacting, for example, with acetic acid/$H_2SO_4$ in a suitable organic solvent such as, for example, an ether, such as $Et_2O$ or dioxane, to form the double bond. Suitable methods are known to the person skilled in the art. These compounds can be obtained, for example, by a Grignard reaction according to the following scheme:

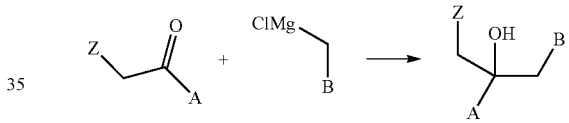

See also EP 409049.

According to the inventive process, the pure enantiomers or a mixture of enantiomers (racemic or enantiomerically enriched) of the reactants, in particular of compounds of formula (IV), can be used. According to a preferred embodiment, the racemic mixture is used. Depending on the use of the respective reactant, in particular of compound of formula (IV), it is possible to obtain compounds of formula (I) having a certain stereochemistry. For example, the following different stereoisomers of compounds (I)-(1) can be obtained using the inventive process:

Compound (I)-(1)-a): Formula (I)-(1), wherein A is 4-fluoro-phenyl and B is 2-chlorophenyl; Y is H; Stereoisomers of compound (I)-(1)-a):

compound (I)-(1)-a1):

Formula (I)-(1), wherein A is 4-fluoro-phenyl and B is 2-chlorophenyl; Y is H: 2-[(2S,3S)-3-(2-Chloro-phenyl)-2-(4-fluoro-phenyl)-oxiranylmethyl]-2H-[1,2,4]triazole-3-thiol ("cis")

compound (I)-(1)-a2):

Formula (I)-(1), wherein A is 4-fluoro-phenyl and B is 2-chlorophenyl; Y is H: 2-[(2R,3R)-3-(2-Chloro-phenyl)-2-(4-fluoro-phenyl)-oxiranylmethyl]-2H-[1,2,4]triazole-3-thiol ("cis")

compound (I)-(1)-a3):

Formula (I)-(1), wherein A is 4-fluoro-phenyl and B is 2-chlorophenyl; Y is H: 2-[(2S,3R)-3-(2-Chloro-phenyl)-2-(4-fluoro-phenyl)-oxiranylmethyl]-2H-[1,2,4]triazole-3-thiol ("trans")

compound (I)-(1)-a4):

Formula (I)-(1), wherein A is 4-fluoro-phenyl and B is 2-chlorophenyl; Y is H: 2-[(2R,3S)-3-(2-Chloro-phenyl)-2-(4-fluoro-phenyl)-oxiranylmethyl]-2H-[1,2,4]triazole-3-thiol ("trans")

Compound (I)-(1)-b):

compound (I)-(1)-b1): Formula (I)-(1), wherein A is 2,4-difluoro-phenyl and B is 2-chlorophenyl; Y is H; Stereoisomers of compound (I)-(1)-b):

Formula (I)-(1), wherein A is 2,4-difluoro-phenyl and B is 2-chlorophenyl; Y is H 2-[(2S,3S)-3-(2-Chloro-phenyl)-2-(2,4-difluoro-phenyl)-oxiranylmethyl]-2H-[1,2,4]triazole-3-thiol ("cis")

compound (I)-(1)-b2):

Formula (I)-(1), wherein A is 2,4-difluoro-phenyl and B is 2-chlorophenyl; Y is H: 2-[(2R,3R)-3-(2-Chloro-phenyl)-2-(2,4-difluoro-phenyl)-oxiranylmethyl]-2H-[1,2,4]triazole-3-thiol ("cis")

compound (I)-(1)-b3):

Formula (I)-(1), wherein A is 2,4-difluoro-phenyl and B is 2-chlorophenyl; Y is H: 2-[(2S,3R)-3-(2-Chloro-phenyl)-2-(2,4-difluoro-phenyl)-oxiranylmethyl]-2H-[1,2,4]triazole-3-thiol ("trans")

compound (I)-(1)-b4):

Formula (I)-(1), wherein A is 2,4-difluoro-phenyl and B is 2-chlorophenyl; Y is H: 2-[(2R,3S)-3-(2-Chloro-phenyl)-2-(2,4-difluoro-phenyl)-oxiranylmethyl]-2H-[1,2,4]triazole-3-thiol ("trans")

Furthermore, the following different stereoisomers of compounds (I)-(1) can be obtained using the inventive process:

Compound (I)-(1)-c): Formula (I)-(1), wherein A=2,4-difluorophenyl, B=2-chlorophenyl and Y is allyl. Stereoisomers of compound (I)-(1)-c):

(I)-(1)-c1): 5-allylsulfanyl-1-[[(2S,3S)-3-(2-chlorophenyl)-2-(2,4-difluorophenyl)oxiran-2-yl]methyl]-1,2,4-triazole ("cis")

(I)-(1)-c2): 5-allylsulfanyl-1-[[(2R,3R)-3-(2-chlorophenyl)-2-(2,4-difluorophenyl)oxiran-2-yl]methyl]-1,2,4-triazole ("cis")

(I)-(1)-c3): 5-allylsulfanyl-1-[[(2S,3R)-3-(2-chlorophenyl)-2-(2,4-difluorophenyl)oxiran-2-yl]methyl]-1,2,4-triazole ("trans")

(I)-(1)-c4): 5-allylsulfanyl-1-[[(2R,3S)-3-(2-chlorophenyl)-2-(2,4-difluorophenyl)oxiran-2-yl]methyl]-1,2,4-triazole ("trans")

Compound (I)-(1)-d): Formula (I)-(1), wherein A=4-fluorophenyl, B=2-chlorophenyl and Y is allyl. Stereoisomers of compound (I)-(1)-d):

(I)-(1)-d1): 5-allylsulfanyl-1-[[(2S,3S)-3-(2-chlorophenyl)-2-(4-fluorophenyl)oxiran-2-yl]methyl]-1,2,4-triazole ("cis")

(I)-(1)-d2): 5-allylsulfanyl-1-[[(2R,3R)-3-(2-chlorophenyl)-2-(4-fluorophenyl)oxiran-2-yl]methyl]-1,2,4-triazole ("cis")

(I)-(1)-d3): 5-allylsulfanyl-1-[[(2S,3R)-3-(2-chlorophenyl)-2-(4-fluorophenyl)oxiran-2-yl]methyl]-1,2,4-triazole ("trans")

(I)-(1)-d4): 5-allylsulfanyl-1-[[(2R,3S)-3-(2-chlorophenyl)-2-(4-fluorophenyl)oxiran-2-yl]methyl]-1,2,4-triazole ("trans")

Compound (I)-(1)-e): Formula (I)-(1), wherein A=2,4-difluorophenyl, B=2-chlorophenyl and Y is CN. Stereoisomers of compound (I)-(1)-e):

(I)-(1)-e1): 1-[rel(2S,3S)-3-(2-chlorophenyl)-2-(2,4-difluorophenyl)oxiranylmethyl]-5-thiocyanato-1H-[1,2,4]triazole ("cis")

(I)-(1)-e2): 1-[rel(2R,3R)-3-(2-chlorophenyl)-2-(2,4-difluorophenyl)oxiranylmethyl]-5-thiocyanato-1H-[1,2,4]triazole ("cis")

(I)-(1)-e3): 1-[rel(2S,3R)-3-(2-chlorophenyl)-2-(2,4-difluorophenyl)oxiranylmethyl]-5-thiocyanato-1H-[1,2,4]triazole ("trans")

(I)-(1)-e3): 1-[rel(2R,3S)-3-(2-chlorophenyl)-2-(2,4-difluorophenyl)oxiranylmethyl]-5-thiocyanato-1H-[1,2,4]triazole ("trans")

With respect to the fungicidal activity of the end products, it may be preferred, if the "trans" diastereomers are synthesized in the inventive process.

Specific compounds (I)-(1) and (IV)-(1) are such compounds, wherein A and B have the meaning as defined in tables 1a to 138a in combination with table A below (there, A and B are defined for compounds (X)-(1)).

According to one embodiment of the invention, in the inventive processes, R is (1) and therein, A is 2,4-difluorophenyl and B is 2-chlorophenyl or A is 4-fluorophenyl and B is 2-chlorophenyl.

One undesired side product in the synthesis of compounds (I)-(1) that may occur in undesired amounts with prior art processes and that can be reduced or even avoided using the new inventive process is the cyclizised hydroxy compound IA:

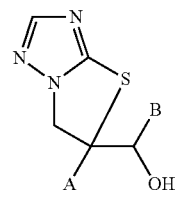

IA wherein A and B are as defined and preferably defined as for compounds (I)-(1). In conventional processes, for example using high temperature or n-butyllithium as a base, product IA may occur to up to 100%, leading, consequently, to very low yields of the desired product of formula (I). According to the inventive process, in particular when carrying out the process steps (ii) and (iii-1), more particular steps (i), (ii) and (iii-1), in case R has the meaning (1), side product IA is formed preferably to equal or less than 10%, more preferably equal or less than 8%, even more preferably equal or less than 5%, even more preferably equal or less than 3%.

Another undesired side product in the synthesis of compounds (I)-(1) that may occur in undesired amounts with prior art processes and that can be reduced or even avoided using the new inventive process, is the cyclizised hydroxy compound IB:

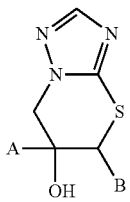

wherein A and B are as defined and preferably defined as for compounds (I)-(1). In conventional processes, for example using high temperature or n-butyllithium as a base, product IB may occur to up to 100%, leading, consequently, to very low yields of the desired product of formula (I). According to the inventive process, in particular when carrying out the process steps (ii) and (iii-1), more particular steps (i), (ii) and (iii-1), in case R has the meaning (1), side product IA is formed preferably to equal or less than 10%, more preferably equal or less than 8%, even more preferably equal or less than 5%, even more preferably equal or less than 3%.

Specifically, in the synthesis of compounds (I)-(1), wherein A and B are as defined in the following table B, the respective compounds IB-1 to IB-81 as individualized in table B, are undesired side products that are preferably reduced according to the inventive process.

TABLE B

| specific compounds IB | | |
|---|---|---|
| compound | A | B |
| IB-1 | 2-fluorophenyl | 2-chlorophenyl |
| IB-2 | 2-fluorophenyl | 3-chlorophenyl |
| IB-3 | 2-fluorophenyl | 4-chlorophenyl |
| IB-4 | 2-fluorophenyl | 2-methylphenyl |
| IB-5 | 2-fluorophenyl | 3-methylphenyl |
| IB-6 | 2-fluorophenyl | 4-methylphenyl |
| IB-7 | 2-fluorophenyl | 2-trifluoromethylphenyl |
| IB-8 | 2-fluorophenyl | 3-trifluoromethylphenyl |
| IB-9 | 2-fluorophenyl | 4-trifluoromethylphenyl |
| IB-10 | 3-fluorophenyl | 2-chlorophenyl |
| IB-11 | 3-fluorophenyl | 3-chlorophenyl |
| IB-12 | 3-fluorophenyl | 4-chlorophenyl |
| IB-13 | 3-fluorophenyl | 2-methylphenyl |
| IB-14 | 3-fluorophenyl | 3-methylphenyl |
| IB-15 | 3-fluorophenyl | 4-methylphenyl |
| IB-16 | 3-fluorophenyl | 2-trifluoromethylphenyl |
| IB-17 | 3-fluorophenyl | 3-trifluoromethylphenyl |
| IB-18 | 3-fluorophenyl | 4-trifluoromethylphenyl |
| IB-19 | 4-fluorophenyl | 2-chlorophenyl |
| IB-20 | 4-fluorophenyl | 3-chlorophenyl |
| IB-21 | 4-fluorophenyl | 4-chlorophenyl |
| IB-22 | 4-fluorophenyl | 2-methylphenyl |
| IB-23 | 4-fluorophenyl | 3-methylphenyl |
| IB-24 | 4-fluorophenyl | 4-methylphenyl |
| IB-25 | 4-fluorophenyl | 2-trifluoromethylphenyl |
| IB-26 | 4-fluorophenyl | 3-trifluoromethylphenyl |
| IB-27 | 4-fluorophenyl | 4-trifluoromethylphenyl |
| IB-28 | 2,3-difluorophenyl | 2-chlorophenyl |
| IB-29 | 2,3-difluorophenyl | 3-chlorophenyl |
| IB-30 | 2,3-difluorophenyl | 4-chlorophenyl |
| IB-31 | 2,3-difluorophenyl | 2-methylphenyl |
| IB-32 | 2,3-difluorophenyl | 3-methylphenyl |
| IB-33 | 2,3-difluorophenyl | 4-methylphenyl |
| IB-34 | 2,3-difluorophenyl | 2-trifluoromethylphenyl |
| IB-35 | 2,3-difluorophenyl | 3-trifluoromethylphenyl |
| IB-36 | 2,3-difluorophenyl | 4-trifluoromethylphenyl |
| IB-37 | 2,4-difluorophenyl | 2-chlorophenyl |
| IB-38 | 2,4-difluorophenyl | 3-chlorophenyl |
| IB-39 | 2,4-difluorophenyl | 4-chlorophenyl |
| IB-40 | 2,4-difluorophenyl | 2-methylphenyl |
| IB-41 | 2,4-difluorophenyl | 3-methylphenyl |

TABLE B-continued

| specific compounds IB | | |
|---|---|---|
| compound | A | B |
| IB-42 | 2,4-difluorophenyl | 4-methylphenyl |
| IB-43 | 2,4-difluorophenyl | 2-trifluoromethylphenyl |
| IB-44 | 2,4-difluorophenyl | 3-trifluoromethylphenyl |
| IB-45 | 2,4-difluorophenyl | 4-trifluoromethylphenyl |
| IB-46 | 2,5-difluorophenyl | 2-chlorophenyl |
| IB-47 | 2,5-difluorophenyl | 3-chlorophenyl |
| IB-48 | 2,5-difluorophenyl | 4-chlorophenyl |
| IB-49 | 2,5-difluorophenyl | 2-methylphenyl |
| IB-50 | 2,5-difluorophenyl | 3-methylphenyl |
| IB-51 | 2,5-difluorophenyl | 4-methylphenyl |
| IB-52 | 2,5-difluorophenyl | 2-trifluoromethylphenyl |
| IB-53 | 2,5-difluorophenyl | 3-trifluoromethylphenyl |
| IB-54 | 2,5-difluorophenyl | 4-trifluoromethylphenyl |
| IB-55 | 2,6-difluorophenyl | 2-chlorophenyl |
| IB-56 | 2,6-difluorophenyl | 3-chlorophenyl |
| IB-57 | 2,6-difluorophenyl | 4-chlorophenyl |
| IB-58 | 2,6-difluorophenyl | 2-methylphenyl |
| IB-59 | 2,6-difluorophenyl | 3-methylphenyl |
| IB-60 | 2,6-difluorophenyl | 4-methylphenyl |
| IB-61 | 2,6-difluorophenyl | 2-trifluoromethylphenyl |
| IB-62 | 2,6-difluorophenyl | 3-trifluoromethylphenyl |
| IB-63 | 2,6-difluorophenyl | 4-trifluoromethylphenyl |
| IB-64 | 3,4-difluorophenyl | 2-chlorophenyl |
| IB-65 | 3,4-difluorophenyl | 3-chlorophenyl |
| IB-66 | 3,4-difluorophenyl | 4-chlorophenyl |
| IB-67 | 3,4-difluorophenyl | 2-methylphenyl |
| IB-68 | 3,4-difluorophenyl | 3-methylphenyl |
| IB-69 | 3,4-difluorophenyl | 4-methylphenyl |
| IB-70 | 3,4-difluorophenyl | 2-trifluoromethylphenyl |
| IB-71 | 3,4-difluorophenyl | 3-trifluoromethylphenyl |
| IB-72 | 3,4-difluorophenyl | 4-trifluoromethylphenyl |
| IB-73 | 3,5-difluorophenyl | 2-chlorophenyl |
| IB-74 | 3,5-difluorophenyl | 3-chlorophenyl |
| IB-75 | 3,5-difluorophenyl | 4-chlorophenyl |
| IB-76 | 3,5-difluorophenyl | 2-methylphenyl |
| IB-77 | 3,5-difluorophenyl | 3-methylphenyl |
| IB-78 | 3,5-difluorophenyl | 4-methylphenyl |
| IB-79 | 3,5-difluorophenyl | 2-trifluoromethylphenyl |
| IB-80 | 3,5-difluorophenyl | 3-trifluoromethylphenyl |
| IB-81 | 3,5-difluorophenyl | 4-trifluoromethylphenyl |

According to another embodiment of the present invention, the organic group R in the compounds (I) and the precursors thereof carries a free hydroxy group and compounds (I) are from the triazole class of fungicides. In a particular embodiment thereof, R stands for a group of formula (2):

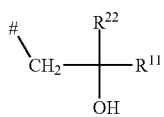

wherein $R^{11}$ and $R^{22}$ have the following meanings:

$R^{11}$, $R^{22}$ independently of one another $C_1$-$C_6$-alkyl, $C_1$-$C_6$-haloalkyl, $C_3$-$C_6$-cycloalkyl, $C_3$-$C_6$-halocycloalkyl or phenyl, wherein the alkyl, cycloalkyl and phenyl moieties may be unsubstituted or substituted by one, two, three or four substituents L as defined or preferably defined above for compounds, wherein R is a group (1); or $R^{11}$ and $R^{22}$, together with the carbon atom to which they are attached, form a five- or six-membered saturated or partially unsaturated ring, that can be unsubstituted or substituted by one, two, three, four or five substituents U, wherein U stands for L as defined above or stands for a group

wherein $R^{33}$ and $R^{44}$ independently are selected from the group of hydrogen and the meaning for L as defined above.

According to one embodiment, $R^{11}$ and $R^{12}$ are preferably independently selected from $C_1$-$C_4$-alkyl and phenyl, wherein the alkyl and phenyl group independently may contain one, two, three or four substitutents, independently selected from F, Cl, Br, methoxy, ethoxy, propoxy, isopropoxy, $C_1$-$C_2$-alkoximino, cyclopropyl, cyclobutyl, cyclopentyl and/or cyclohexyl. Specifically, $R^{11}$ stands for $C_1$-$C_4$-alkyl that is substituted by one or two substituents independently selected from F, Cl, methoxy, cyclopropyl, cyclopentyl and/or cyclohexyl and $R^{12}$ stands for phenyl, that is substituted by one, two, three or four substituents independently selected from F, Cl, Br and methoxy. In one specific embodiment, $R^{11}$ is 1-ethyl that is 1-substituted by cyclopropyl and $R^{12}$ is 4-chlorophenyl. According to another specific embodiment, $R^{11}$ is n-butyl and $R^{12}$ is 2,4-dichlorophenyl.

According to another embodiment, $R^{11}$ and $R^{12}$ are preferably independently selected from $C_1$-$C_4$-alkyl, phenyl-$C_1$-$C_4$-alkyl and $C_3$-$C_6$-cycloalkyl, preferably phenyl-$C_1$-$C_4$-alkyl and $C_3$-$C_6$-cycloalkyl, wherein the alkyl, phenyl and cycloalkyl groups independently may contain one, two, three or four substitutents, independently selected from F, Cl, Br, CN, methyl, ethyl, propyl, isopropyl and/or tert-butyl. Specifically, $R^{11}$ stands for phenyl-$C_1$-$C_4$-alkyl that is substituted in the phenyl moiety by one, two, three or four substituents independently selected from F, Cl and methoxy and $R^{12}$ stands for $C_3$-$C_6$-cycloalkyl, that is substituted by one, two, three or four substituents independently selected from F, Cl, Br and methoxy. In one specific embodiment, $R^{11}$ is 2-chlorophenylmethyl and $R^{12}$ is 1-chlorocyclopropyl.

According to still another embodiment, $R^{11}$ and $R^{12}$ are preferably independently selected from $C_1$-$C_4$-alkyl and phenyl-$C_1$-$C_4$-alkyl, wherein the alkyl and phenyl groups may contain one, two, three or four substituents, independently selected from F, Cl, Br, CN, methyl, ethyl, propyl, isopropyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxyvarbonyl, methoxyiminomethyl, 1-methoximinoethyl and nitro. Specifically, $R^{11}$ stands for $C_1$-$C_4$-alkyl that may be substituted by one or two substituents, independently selected from methyl, ethyl, propyl, isopropyl and tert-butyl and $R^{12}$ stands for phenyl-$C_1$-$C_4$-alkyl, that is substituted in the phenyl moiety by one, two, three or four substituents independently selected from F, Cl, Br, CN, methyl, trifluoromethyl and methoxy. In one specific embodiment $R^{11}$ is tert-butyl and $R^{12}$ is 2-(4-chlorophenyl)-1-ethyl.

According to still another embodiment, $R^{11}$ and $R^{12}$ are preferably independently selected from phenyl, wherein the phenyl moieties may contain one, two, three or four substitutents, independently selected from F, Cl, Br, CN, methyl, ethyl, propyl, iso-propyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxyvarbonyl, methoxyiminomethyl, 1-methoximinoethyl and nitro. Specifically, $R^{11}$ and $R^{12}$ independently stand for phenyl, that may contain one, two or three substitutents, independently selected from F, Cl and Br. In one specific embodiment $R^{11}$ is 2-fluorophenyl and $R^{12}$ is 4-fluorophenyl.

According to still another embodiment, preferably $R^{11}$ and $R^{22}$, together with the carbon atom to which they are attached, form a five- or six-membered saturated ring, that can be unsubstituted or substituted by one, two or three substituents L', wherein L' stands for L as defined above or stands for a group

wherein $R^{33}$ and $R^{44}$ independently are selected from the group of hydrogen, $C_1$-$C_4$-alkyl and phenyl, wherein the alkyl and phenyl groups may contain one, two, three or four substitutents, independently selected from F, Cl, Br, CN, methyl, ethyl, propyl, isopropyl, tert-butyl, methoxy, ethoxy, methylthio, trifluoromethyl, trifluoromethoxy, trifluoromethylthio, chlorodifluoromethoxy, difluoromethoxy and nitro. Specifically, $R^{11}$ and $R^{22}$, together with the carbon atom to which they are attached, form a five-membered saturated ring, that is substituted by one, two or three substituents L', wherein L' stands for $C_1$-$C_4$-alkyl or for a group

wherein $R^{33}$ and $R^{44}$ independently are selected from the group of hydrogen, $C_1$-$C_4$-alkyl and phenyl, wherein the alkyl and phenyl groups may contain one, two, three or four substitutents, independently selected from F, Cl, CN, methyl, isopropyl, tert-butyl and methoxy. In one specific embodiment $R^{11}$ and $R^{22}$, together with the carbon atom to which they are attached, form a five-membered saturated ring, that is substituted in 5-position by two methyl groups and contains a group

wherein $R^{33}$ is hydrogen and $R^{44}$ is 4-chlorophenyl in 2-position.

According to still another embodiment, $R^{11}$ and $R^{22}$, together with the carbon atom to which they are attached, form a five- or six-membered saturated ring, that can be un-substituted or substituted by one, two or three substituents, independently selected from F, Cl, Br, CN, methyl, ethyl, propyl, isopropyl, tert-butyl, methoxy, ethoxy, methylthio, trifluoromethyl, trifluoromethoxy, trifluoromethylthio, chlorodifluoromethoxy, difluoromethoxy, nitro, benzyl, wherein the phenyl moiety itself may contain on, two, three or four substituents, independently selected from F, Cl, CN, methyl, isopropyl, tert-butyl and methoxy. In one specific embodiment $R^{11}$ and $R^{22}$, together with the carbon atom to which they are attached, form a five-membered saturated ring, that is substituted in 5-position by two methyl groups and contains a 4-chlorobenzyl group in 2-position. Regarding compounds (I)-(2) and the synthesis of precursors thereof see also WO 96/16048, WO 96/38423, EP378953, EP655443, DE 4030039, DE 3337937, DE3315681, U.S. Pat. No. 4,414, 210.

According to another embodiment of the present invention, R stands for a group of formula (3):

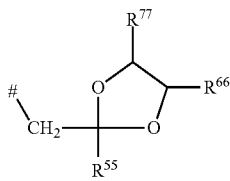

(3)

wherein $R^{55}$, $R^{66}$ and $R^{77}$ have the following meanings:

$R^{55}$ phenyl-$C_1$-$C_8$-alkyl, phenyl or a five- or six-membered saturated, partially unsaturated or aromatic heterocycle which contains one, two, three or four heteroatoms from the group consisting of O, N and S; where the aliphatic and/or aromatic and/or heterocyclic groups for their part may carry one, two, three or four identical or different groups selected from halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino, phenyl, halophenyl, phenyloxy, halophenyloxy;

$R^{66}$, $R^{77}$ independently of one another hydrogen, $C_1$-$C_6$-alkyl, $C_1$-$C_6$-haloalkyl, $C_3$-$C_6$-cycloalkyl, $C_3$-$C_6$-halocycloalkyl or phenyl, wherein the alkyl, cycloalkyl or phenyl moieties may be unsubstituted or substituted by one, two or three substituents selected from halogen, cyano, nitro, $C_1$-$C_8$-alkyl, $C_1$-$C_8$-haloalkyl, $C_1$-$C_8$-alkoxy, $C_1$-$C_8$-haloalkoxy According to one embodiment, $R^{55}$ is phenyl, that is unsubstituted or substituted by one, two, three or four substituents independently selected from halogen, $C_1$-$C_6$-alkyl, $C_1$-$C_6$-haloalkyl, phenoxy-$C_1$-$C_6$-alkyl and halophenyloxy, and $R^{66}$ and $R^{77}$ are independently selected from hydrogen, methyl, ethyl, n-propyl and n-butyl. Specifically, $R^{55}$ is phenyl, that contains one, two or three substituents independently selected from F, Cl and halophenoxy, wherein the phenoxy moiety contains one or two halogen atoms selected from Cl and F; and $R^{66}$ is hydrogen and $R^{77}$ is $C_1$-$C_4$-alkyl. In one specific embodiment $R^{55}$ is 4-(4-chlorophenoxy)-2-chlorophenyl, $R^{66}$ is hydrogen and $R^{77}$ is methyl. In another specific embodiment $R^{55}$ is 2,4-dichlorophenyl, $R^{66}$ is hydrogen and $R^{77}$ is n-propyl.

Regarding compounds (I)-(3) and the synthesis of precursors thereof see also WO 96/41804 and Pestic. Sci, 1980, 11, 95 and Research Disclosure 1989, 297,13.

According to another embodiment of the present invention, R stands for a group of formula (4):

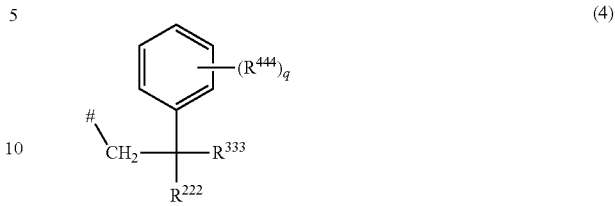

(4)

wherein $R^{222}$, $R^{333}$ and $R^{444}$ have the following meanings:

$R^{222}$ and $R^{333}$ are independently selected from hydrogen, cyano, $C_1$-$C_6$-alkyl and $C_1$-$C_6$-haloalkyl, wherein the alkyl moieties may be unsubstituted or substituted by one, two, three or four substituents L as defined or preferably defined above for compounds, wherein R is a group (1). In particular, $R^{222}$ and $R^{333}$ are independently selected from hydrogen, cyano and $C_1$-$C_4$-alkyl, wherein the alkyl moiety may contain one, two, three or four substituents independently selected from F, Cl, CN, $C_1$-$C_4$-alkoxy and $C_1$-$C_4$-haloalkoxy. q is one, two three or five, preferably one or two, and $R^{444}$ are independently selected from L as defined or preferably defined above for compounds, wherein R is a group (1), in particular independently selected from F, Cl, CN, methyl, isopropyl, tert-butyl and methoxy, more specifically independently selected from Cl and F. According to one specific embodiment, $R^{222}$, is hydrogen, $R^{333}$ is methyl, substituted by 1,1,2,2-tetrafluoroethoxy, and $R^{444}$ is 2,4-dichlorophenyl. According to another specific embodiment, $R^{222}$ is cyano, $R^{333}$ is n-butyl and $R^{444}$ is 4-chlorophenyl. According to still another specific embodiment, $R^{222}$ is hydrogen, $R^{333}$ is n-propyl and $R^{444}$ is 2,4-dichlorophenyl. Regarding compounds (I)-(4) and the synthesis of precursors thereof see also DE19528300, DE19529089.

According to another embodiment of the present invention. R stands for a group of formula (5):

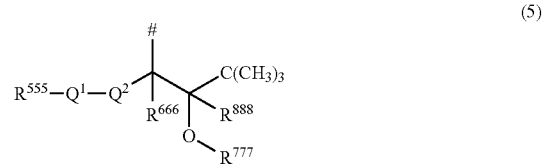

(5)

wherein # shall mean the point of attachment to the triazolo group and $Q^1$, $Q^2$, $R^{555}$, $R^{666}$, $R^{777}$ and $R^{888}$ are as defined as follows:

$Q^1$ O or a single bond to $R^{555}$;

$Q^2$ saturated hydrocarbon chain containing two to five carbon atoms, which may contain one, two or three substituents $R^z$, wherein $R^z$ has the meaning:

$R^z$ halogen, $C_1$-$C_8$-alkyl, $C_1$-$C_8$-haloalkyl, $C_2$-$C_8$-alkenyl, $C_2$-$C_8$-haloalkenyl, $C_1$-$C_8$-alkoxy, $C_1$-$C_8$-haloalkoxy, $C_1$-$C_8$-alkylcarbonyloxy, $C_2$-$C_8$-alkenyloxy, $C_2$-$C_8$-haloalkenyloxy, $C_3$-$C_8$-cycloalkyl, $C_3$-$C_8$-halo cycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, $C_1$-$C_6$-alkylen, oxy-$C_2$-$C_4$-alkylen, phenoxy, phenyl; wherein $R^z$ in each case is unsubstituted or contains one, two or three substituents, independently selected from $L^1$;

$R^{555}$ phenyl, which is unsubstituted or contains one, two, three, four or five independently selected substituents $L^1$, wherein $L^1$ has the meanings:

$L^1$ halogen, $C_1$-$C_8$-alkyl, $C_1$-$C_8$-haloalkyl, $C_2$-$C_8$-alkenyl, $C_2$-$C_8$-haloalkenyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_2$-$C_8$-alkenyloxy, $C_2$-$C_8$-haloalkenyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, $C_1$-$C_6$-alkylen, the aliphatic and/or alicyclic and/or aromatic groups of the definitions of $L^1$ may contain one, two, three or four groups $R^{L1}$ that are the same or different from each other:

$R^{L1}$ halogen, hydroxy, cyano, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl, $C_3$-$C_8$-cycloalkenyl, $C_3$-$C_8$-cycloalkoxy, $C_3$-$C_8$-halocycloalkoxy, $C_1$-$C_6$-alkylen, oxy-$C_2$-$C_4$-alkylen, oxy-$C_1$-$C_3$-alkylenoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

$R^{666}$ hydrogen, halogen, $C_1$-$C_{10}$-alkyl, $C_1$-$C_{10}$-haloalkyl, $C_2$-$C_{10}$-alkenyl, $C_2$-$C_{10}$-haloalkenyl, $C_3$-$C_{10}$-cycloalkyl, $C_3$-$C_{10}$-halocycloalkyl;

$R^{777}$ hydrogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkinyl, $C_3$-$C_{10}$-cycloalkyl, $C_3$-$C_{10}$-halocycloalkyl, $C_3$-$C_{10}$-cycloalkenyl, $C_3$-$C_{10}$-halocycloalkenyl, tri-$C_1$-$C_{10}$-alkylsilyl;

$R^{888}$ hydrogen, $C_1$-$C_{10}$-alkyl, $C_1$-$C_{10}$-haloalkyl, $C_2$-$C_{10}$-alkenyl, $C_2$-$C_{10}$-halogenalkenyl, $C_3$-$C_{10}$-cycloalkyl;

$R^{666}$, $R^{777}$ and $R^{888}$ are, if it is not indicated otherwise, independently from each other unsubstituted or substituted with one, two, three, four or five $L^1$, as defined above.

Specific compounds (I)-(5) that may be synthesized according to the present invention, including the respective intermediate compounds, are the following, including each one of the possible stereoisomers thereof:

(I)-(5)-a): formula (I)-(5), in which $Q^1$-$Q^2$=$(CH_2)_4$, $R^{555}$=2-fluorophenyl and $R^{666}$, $R^{777}$ and $R^{888}$ are hydrogen; Y=H;

(I)-(5)-b): formula (I)-(5), in which $Q^1$-$Q^2$=$CH_2CH(CH_3)CH_2$, $R^{555}$=2,4-dichlorophenyl and $R^{666}$, $R^{777}$ and $R^{888}$ are hydrogen; Y=H.

For compounds (I)-(5) and their precursors (in particular wherein the triazole group does not contain SH or a derivatized sulfur group) and the preparation of the same, see WO2010/029001, WO2010/029002, WO 2010/029000, WO 2010/029003, WO2010/031721, WO 2010/031847, WO 2010/031848, WO 2010/031842 (PCT/EP 2009/062122) and/or WO 2010/040718 (PCT/EP2009/062909).

Y in the compounds (I) is hydrogen, halogen, $(C_1$-$C_8)$-alkyl, $(C_1$-$C_8)$-haloalkyl, $(C_2$-$C_8)$-alkenyl, $(C_2$-$C_8)$-haloalkenyl, $(C_2$-$C_8)$-alkynyl, $(C_2$-$C_8)$-haloalkynyl, $(C_6$-$C_{10})$-aryl, a five-, six-, seven-, eight-, nine- or ten-membered aromatic heterocycle that contains one, two, three or four heteroatoms from the group consisting of O, N and S, $C(=S)R^9$, $SO_2R^{10}$ or CN; wherein $R^9$ is $NA^3A^4$; wherein $A^3$, $A^4$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $(C_6$-$C_{10})$-aryl, a five-, six-, seven-, eight-, nine- or ten-membered aromatic heterocycle that contains one, two, three or four heteroatoms from the group consisting of O, N and S;

$R^{10}$ is $(C_1$-$C_8)$-alkyl, phenyl-$(C_1$-$C_8)$-alkyl or phenyl, where the phenyl groups are in each case unsubstituted or substituted by one, two or three groups independently selected from the group consisting of halogen and $(C_1$-$C_4)$-alkyl.

According to one embodiment, Y in compounds (I) is hydrogen.

According to a further embodiment of the invention, Y in compounds (I) is $(C_1$-$C_8)$-alkyl, $(C_2$-$C_8)$-alkenyl or CN.

According to a further embodiment of the invention, Y in compounds (I) is $C_1$-$C_8$-alkyl, preferably $C_1$-$C_5$-alkyl or $C_1$-$C_4$-alkyl. According to one specific embodiment, Y in compounds (I) is $C_3$-alkyl, according to another specific embodiment, Y in compounds (I) is $C_5$-alkyl. Particular examples of preferred Y are methyl, ethyl, iso-propyl, n-butyl or n-pentyl.

According to still a further embodiment of the invention Y in compounds (I) is $(C_2$-$C_8)$-alkenyl, in particular $(C_3$-$C_6)$-alkenyl such as Y=allyl.

According to still a further embodiment of the invention Y in compounds (I) is CN.

One key step of the present invention is providing a triazole magnesium compound of formula (IIIa)

(IIIa)

by means of a process comprising the step
(i) reacting a triazolo compound of formula (IV)

(IV)

with a Grignard reagent $R^1MgQ$ (V), wherein the variables are defined above.

According to one embodiment of the invention Q is $R^1$. According to another embodiment of the invention, Q is X, wherein X is halogen, in particular Cl or Br.

$R^1$ is $(C_1$-$C_{10})$-alkyl, $(C_2$-$C_{10})$-alkenyl, $(C_2$-$C_{10})$-alkynyl, $(C_3$-$C_8)$-cycloalkyl or $(C_6$-$C_{10})$-aryl, wherein the aryl is unsubstituted or substituted by one, two or three groups independently selected from the group consisting of halogen and $(C_1$-$C_4)$-alkyl. In particular, $R^1$ is $(C_1$-$C_6)$-alkyl, $(C_2$-$C_6)$-alkenyl, $(C_3$-$C_6)$-cycloalkyl or phenyl, optionally containing one, two or three substituents selected from Cl, F, methyl and ethyl. According to one embodiment, $R^1$ is $(C_1$-$C_6)$-alkyl, in particular $(C_2$-$C_4)$-alkyl. Specific examples for $R^1$ are methyl, ethyl, n-propyl, iso-propyl, n-butyl, iso-butyl and tert-butyl. It may be preferred according to the invention to use secondary Grignard reagents, wherein the secondary group may be cyclic or acyclic. Secondary Grignard reagents are for example compounds (V), wherein $R^1$ is iso-propyl or cyclopentyl.

According to another embodiment, $R^1$ is $(C_2$-$C_6)$-alkenyl, in particular vinyl.

According to still another embodiment, $R^1$ is unsubstituted phenyl.

Specific Grignard reagents $R^1MgQ$ (V) that are suitable for the inventive process are, for example, MeMgCl, MeMgBr, EtMgCl, EtMgBr, iBuMgCl, iPrMgCl, CyclopentylMgCl, CyclohexylMgCl, tBuMgCl, VinylMgCl and PhMgCl. Also possible is the use of $(R^1)_2Mg$ such as n-Bu$_2$Mg.

As generally known to the skilled person, the structure of a Grignard reagent can be described by the so-called Schlenck-equilibrium. A Grignard reagent undergoes a solvent-dependent equilibrium between different magnesium compounds. The Schlenck-equilibrium for the Grignard reagent used according to the present invention can be schematically illustrated as follows:

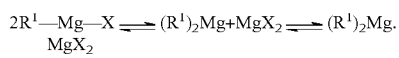

Furthermore, it is known, that solvent molecules, in particular ethers such as diethylether or THF, which are commonly used for reactions with Grignard reagents, can add to the magnesium of the Grignard reagent thereby forming etherates. The different magnesium compounds of the Schlenck equilibrium and possible adducts with solvent molecules are also encompassed by the present invention.

As defined above, the Grignard reagent used according to the inventive process is compound (V): $R^1MgQ$, wherein Q may have the meaning $R^1$. Consequently, according to the invention, it is possible to use a Grignard reagent of the structure $(R^1)_2Mg$ (Q=$R^1$) in the first place. On the other hand, if $R^1MgX$ (Q=X) is used, the Schlenck-equilibrium may result in the formation of $(R^1)_2Mg$ in situ.

The Schlenck-equilibrium may also exist for the reaction product of step (i). Thus, beside product (IIIa) also the compound of formula (IIIb) may be formed:

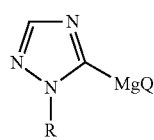
(IIIa)

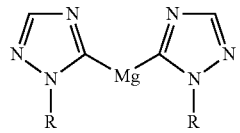
(IIIb)

Furthermore, depending on the solvent used in the reaction, solvent molecules may add to the Mg-reagents, thereby forming—in case of the use of ethers—the respective etherates. Also these addition products with solvent molecules are encompassed by the present invention.

According to an embodiment of the inventive process, LiCl is added to the reaction mixture of step (i). According to an alternative, before contacting the Grignard reagent (v) with a compound of formula (IV), it is brought together with LiCl, thereby forming an addition product $R^1MgX\cdot LiCl$ ((V).LiCl). According to this alternative, ((V).LiCl) is then used in step (i). The use of LiCl together with Grignard reagents is generally known in the art, see for example Angew. Chem. Int. Ed. 2004, 43, 3333 and Angew. Chem. Int. Ed. 2006, 45, 159.

The Grignard reagents (V) or their addition products with LiCl ((V).LiCl) are commercially available or can be made according to processes well-known to the skilled person (see Angew. Chem. Int. Ed. 2004, 43, 3333).

The process step (i) according to the invention can be carried out in any organic solvent that is suitable for Grignard reagents. In general, the use of ethers is advantageous. Possible solvents are for example tetrahydrofuran (THF), 2-methyl-tetrahydrofuran (2-Me-THF), diethyl ether, TBME (tert-butyl methyl ether), CPME (cyclopentyl methyl ether), DME (1,2-dimethoxyethane) and 1,4-dioxane. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

As mentioned above, one advantage of the inventive process is, that it can be carried out in a large temperature range. This especially applies to step (i). In particular, there is no need for cooling the reaction mixture, although the reaction also tolerates cooling. It can also be advantageous to work at elevated temperatures. This can be favourable in order to achieve higher conversion of the reagents to the products. Suitable temperature ranges are −30° C. to 100° C., in particular −10° C. to 80° C., more particularly 0° C. to 20° C. It may be preferred to carry out the reaction at temperatures of 15° C. to 50° C. It may be also preferred to work at temperatures of 40° C. to 60° C.

The reaction components in step (i) are usually employed in amounts such that 1 to 10 moles, in particular 1.1 to 6, more specifically 1.2 to 5, even more specifically 1.2 to 3 moles of Grignard reagent are used per mole of the compound (IV). It may be preferred if 1 to 2.5 moles of Grignard reagent are used per mole of the compound (IV).

Compounds of formula (IIIa) are novel. Accordingly, a further aspect of the present invention is a compound of formula (IIIa)

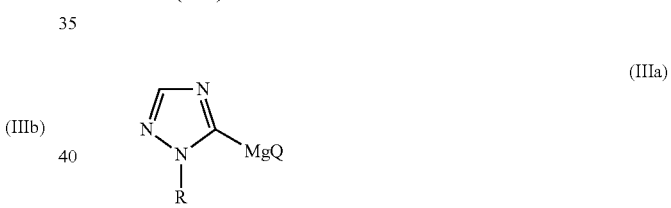
(IIIa)

wherein Q is $R^1$, as defined and preferably defined above or X, wherein X is halogen, in particular Br or Cl, and R is as defined or preferably defined above, wherein it is preferred if R is one of sub-groups (1), (2), (3), (4) or (5) as defined and preferably defined above. According to one specific embodiment, R in compounds (IIIa) is a group (1) as defined above, including the specific embodiments thereof.

Compounds of formula (IIIb) are also novel. Accordingly, a further aspect of the present invention is a compound of formula (IIIb)

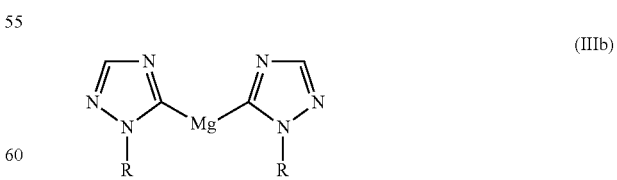
(IIIb)

wherein R is as defined or preferably defined above, wherein it is preferred if R is one of sub-groups (1), (2), (3), (4) or (5) as defined and preferably defined above. According to one specific embodiment, R in compounds (IIIb) is a group (1) as defined above, including the specific embodiments thereof.

According to one specific embodiment, R in compounds (IIIa), respectively, is a group (1) as defined above, including the specific embodiments thereof. In particular, compounds (X)-(1),

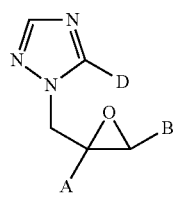
(X)-(1)

wherein D is MgX, according to the invention compiled in tables 1a to 138a in combination with rows 1 to 298 and 597 to 745 of table A below are precursors (IIIa) that are particularly suitable for the inventive process. The groups mentioned for a substituent in the tables are furthermore per se, independently of the combination in which they are mentioned, a particularly preferred aspect of the substituent in question.

A further aspect of the present invention is a use of a compound of formula (IIa) as defined and preferably defined herein, for the synthesis of a thio-triazolo group-containing compound of the formula (I) as defined herein.

According to one aspect of the present invention, a thio-triazolo group-containing compound of the formula (I) is provided by the process described in the following:

A process for the preparation of a thio-triazolo group-containing compound of the formula (I)

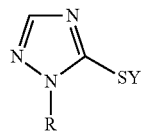
(I)

comprising either step (i) together with steps (ii) and (iii-1) or step (i) together with step (ii) and step (iii-2); or comprising step (i) together with step (iv):

(i) reacting a triazolo compound of formula (IV) as defined and preferably defined herein, and preferably defined herein;
(ii) reacting the reaction mixture resulting from step (i) with sulfur; and
(iii-1) reacting the product of step (ii) with a protonating agent, in order to obtain compounds of formula (I), wherein Y is hydrogen; or
(iii-2) reacting the product of step (ii) with an electrophilic compound $Y^1$-LG in order to obtain compounds of formula (I), wherein Y is $Y^1$, wherein
$Y^1$ is $(C_1$-$C_8)$-alkyl, $(C_1$-$C_8)$-haloalkyl, $(C_2$-$C_8)$-alkenyl, $(C_2$-$C_8)$-haloalkenyl, $(C_2$-$C_8)$-alkynyl, $(C_2$-$C_8)$-haloalkynyl, $C(=S)R^9$, $SO_2R^{10}$ or CN; wherein $R^9$ and $R^{10}$ are as defined and preferably defined herein; and
LG is a leaving group as defined herein;
or
(iv) reacting the reaction mixture resulting from step (i) with an electrophile selected from
(VI) a disulfide $R^2$—S—S—$R^2$, in order to obtain a compound of formula (I), wherein Y is $R^2$;
(VII) $R^3$—S—$SO_2$—$R^3$, in order to obtain a compound of formula (I), wherein Y is $R^3$; or
(VIII) $R^4$—S-Hal, wherein Hal is halogen, in order to obtain a compound of formula (I), wherein Y is $R^4$;
wherein the variables are defined and preferably defined herein.

More specifically, according to a further aspect of the present invention, thio-triazolo-group-containing compounds (I), particularly pesticidal compounds of the triazole class having phytopathogenic activity of formula (I)

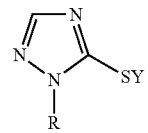
(I)

are synthesized by a process comprising either step (ii) together with step (iii-1) or (iii-2); or comprising step (iv):
(ii) reacting a compound of formula (IIIa)

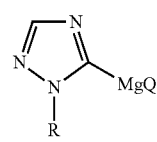
(IIIa)

with sulfur, wherein R and Q are as defined above, in order to obtain a compound of

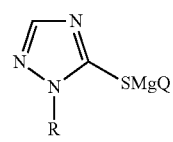
(IIa)

and
(iii-1) protonating said compound of formula (IIa), in order to obtain compounds of formula (I), wherein Y is hydrogen; or
(iii-2) reacting said compound of formula (IIa) with an electrophilic compound $Y^1$-LG in order to obtain compounds of formula (I), wherein Y is $Y^1$, wherein
$Y^1$ is $(C_1$-$C_8)$-alkyl, $(C_1$-$C_8)$-haloalkyl, $(C_2$-$C_8)$-alkenyl, $(C_2$-$C_8)$-haloalkenyl, $(C_2$-$C_8)$-alkynyl, $(C_2$-$C_8)$-haloalkynyl, $C(=S)R^9$, $SO_2R^{10}$ or CN; wherein $R^9$ and $R^{10}$ are as defined below; and
LG is a leaving group;
or
(iv) reacting a compound of formula (IIIa)

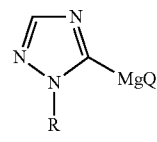
(IIIa)

with an electrophile selected from
(VI) a disulfide $R^2$—S—S—$R^2$, in order to obtain a compound of formula (I), wherein Y is $R^2$;

(VII) $R^3$—S—$SO_2$—$R^3$, in order to obtain a compound of formula (I), wherein Y is $R^3$;

(VIII) $R^4$—S-Hal, wherein Hal is halogen, in order to obtain a compound of formula (I), wherein Y is $R^4$;

wherein R, Q, and Y are as defined and preferably defined above. The remaining variables have the following meanings:

$R^2$, $R^3$ are independently from another ($C_1$-$C_8$)-alkyl, ($C_1$-$C_8$)-haloalkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_6$-$C_{10}$)-aryl, a five-, six-, seven-, eight-, nine- or ten-membered aromatic heterocycle that contains one, two, three or four heteroatoms from the group consisting of O, N and S, C(=S)$R^9$ or CN; and $R^4$ is halogen, ($C_1$-$C_8$)-alkyl, ($C_1$-$C_8$)-haloalkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_6$-$C_{10}$)-aryl or a five-, six-, seven-, eight-, nine- or ten-membered aromatic heterocycle that contains one, two, three or four heteroatoms from the group consisting of O, N and S, or CN.

According to step (ii), a compound (IIIa) is reacted with sulfur, thereby forming magnesium thiolates of formula (IIa). Sulfur ($S_8$) is preferably used as a powder. The reaction components are usually employed in amounts such that 1 to 20 moles, in particular 1.2 to 10, more particularly 1.5 to 5 moles of sulfur are used per mole of the compound (IIIa). It may be preferred if 1 to 4 moles of sulfur are used per mole of the compound (IIIa).

Suitable solvents for step (ii) are all inert organic solvents, where preferably ethers such as tetrahydrofuran, 2-methyl-tetrahydrofuran, 1,4-dioxane, diethyl ether and 1,2-dimethoxyethane can be used. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The reaction temperature is preferably between −30 and 80° C., in particular between −10 and 60° C. It may be preferred to work at temperatures of −5 to 20° C., 0 to 50° C. or 0 to 40° C.

The reaction is generally carried out under atmospheric pressure.

Usually, the reaction mixture resulting from step (ii) is directly used for subsequent steps (iii-1) or (iii-2). However, in case a work-up is suitable, it can be carried out according to procedures generally known to the person skilled in the art.

According to step (iii-1), the respective compound (IIa) is protonated in order to obtain compounds of formula (I), wherein Y is hydrogen (in the following also called compounds (I.1):

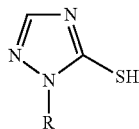

(I.1)

Suitable reagents for the protonation are for example hydrohalic acids, such as hydrogen fluoride, hydrogen chloride, hydrogen bromide and hydrogen iodide, carbonic acid, sulfuric acid, phosphoric acid and nitric acid. The latter acids are generally used in an aqueous medium. Also organic acids can be used for step (iii-1), for example formic acid and alkanoic acids, such as acetic acid, trifluoroacetic acid, trichloroacetic acid and propionic acid, and also glycolic acid, lactic acid, succinic acid, citric acid, benzoic acid and other arylcarboxylic acids, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc.

Furthermore, the protonation step (iii-1) of the inventive process may be carried out using other protonating agents, such as alcohols, for example ($C_1$-$C_6$)-alcohols, in particular methanol, ethanol, isopropanol or isobutanol. Also water as such may be used. It may be preferred to use water, if appropriate in the presence of an organic or inorganic acid such as, for example, acetic acid, dilute sulfuric acid or dilute hydrochloric acid.

According to step (iii-2), the respective compound (IIa) is reacted with the respective electophilic reagent $Y^1$-LG in order to obtain compounds of formula (I), wherein Y is $Y^1$, which is ($C_1$-$C_8$)-alkyl, ($C_1$-$C_8$)-haloalkyl, ($C_2$-$C_8$)-alkenyl, ($C_2$-$C_8$)-haloalkenyl, ($C_2$-$C_8$)-alkynyl, ($C_2$-$C_8$)-haloalkynyl, C(=S)$R^9$, $SO_2R^{10}$ or CN; wherein $R^9$ and $R^{10}$ are as defined and preferably defined above.

LG stands for a leaving group, such as, for example, halogen, such as Cl, Br or I, or alkyl or arylsulfonates like methanesulfonate, benzenesulfonate, 4-toluenesulfonate, 2-nitrobenzenesulfonate, 4-nitrobenzenesulfonate and 4-bromobenzenesulfonate, or perfluorinated alkylsulfonates like trifluoromethanesulfonate or nonafluorobutanesulfonate. Cl, Br and I are mostly preferably used.

In order to obtain target compounds, wherein Y is $C_1$-$C_8$-alkyl, preferably $C_1$-$C_8$-alkyl or $C_1$-$C_4$-alkyl, in particular $C_3$-alkyl or $C_5$-alkyl, specifically methyl, ethyl, iso-propyl, n-butyl or n-pentyl, a compound (IIa) is preferably reacted with the corresponding alkyl halide.

Target compounds (I) with Y being ($C_2$-$C_8$)-alkenyl, in particular ($C_3$-$C_6$)-alkenyl such as Y=allyl, are similarly accessible by reacting compounds (IIa) with the respective ($C_2$-$C_8$)-alkenyl-LG, LG preferably being Br, Cl or I, wherein one particularly suitable reagent is prop-2-enyl bromide.

For target compounds, wherein Y=CN the reagent BrCN is suitable for the inventive process. Also ClCN can be used according to the invention. Furthermore, $(SCN)_2$ is a suitable reagent for obtaining target compounds, wherein Y=CN.

In general, from 1 to 3 equivalents, preferably from 1 to 2.5 equivalents, of reagent $Y^1$-LG are employed per mole of the compound of the formula II.

Suitable solvents for steps (iii-1) and (iii-2) are all inert organic solvents, where preferably ethers such as tetrahydrofuran, dioxane, diethyl ether and 1,2-dimethoxyethane can be used. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The reaction of step (iii-1) or (iii-2) is generally carried out under atmospheric pressure.

The protonation step (iii-1) or the trapping reaction using an electrophile $Y^1$-LG (iii-2), respectively, may be carried out at temperatures from −30 to 80° C., preferably −10 to 60° C., more preferably 0 to 50° C., also preferred 0 to 40° C. In some cases it may be preferred, if temperatures of −30 to 40° C., preferably −10 to 20° C., more preferably 0 to 50° C., also preferred 0 to 40° C., are used.

Work-up of the reaction mixture resulting from reaction step (iii-1) or (iii-2), respectively, is carried out by procedures known in a general manner to the person skilled in the art. Usually, the reaction mixture is extracted with a suitable organic solvent (for example aromatic hydrocarbons such as toluene and xylenes) and the residue is, if appropriate, purified by recrystallization and/or chromatography.

According to one embodiment of step (iv), an inventive magnesium compound (IIIa) and/or (IIIb) is reacted with a disulfide $R^2$—S—S—$R^2$, in order to obtain a compound of formula (I), wherein Y is $R^2$ and $R^2$ is $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_5-C_{10})$-aryl, a five-, six-, seven-, eight-, nine- or ten-membered aromatic heterocycle that contains one, two, three or four heteroatoms from the group consisting of O, N and S, C(=S)$R^9$ or CN, in particular $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, C(=S)$R^9$ or CN. Preferably, $R^2$ is $(C_1-C_5)$-alkyl, in particular methyl, ethyl, iso-propyl, n-propyl, n-butyl or n-pentyl, $(C_3-C_6)$-alkenyl, in particular allyl, or CN. According to a specific embodiment thereof, dirhodane NC—S—S—CN is used in order to result in compounds (I) with Y=CN.

According to a further embodiment of step (iv), an inventive magnesium compound (IIIa) and/or (IIIb) is reacted with a reagent (VII) $R^3$—S—$SO_2$—$R^3$, in order to obtain a compound of formula (I), wherein Y is $R^3$ and $R^3$ is $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms from the group consisting of O, N and S, C(=S)$R^9$ or CN, in particular $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, C(=S)$R^9$ or CN. Preferably, $R^3$ is $(C_1-C_5)$-alkyl, in particular methyl, ethyl, iso-propyl, n-propyl, n-butyl or n-pentyl, $(C_3-C_6)$-alkenyl, in particular allyl or CN.

According to still a further embodiment of step (iv), an inventive magnesium compound (IIIa) and/or (IIIb) is reacted with a reagent (VIII) $R^4$—S-Hal, wherein Hal is halogen, in particular Cl or Br, in order to obtain a compound of formula (I), wherein Y is $R^4$, wherein $R^4$ is halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms from the group consisting of O, N and S, or CN. Specific examples are Y=$R^4$=CN or $CCl_3$. One further particular reagent is $SHal_2$ ($R^4$=Hal), in order to obtain a compound of formula (I), wherein Y is Halogen, in particular Cl. According to still a further embodiment a reagent BrSCN is used in order to obtain a compound (I), wherein Y=$R^4$=CN.

Accordingly, a further aspect of the present invention is a use of a compound of formula (IIIa) as defined and preferably defined herein, for the synthesis of a thio-triazolo group-containing compound of the formula (I) as defined herein.

Suitable solvents for step (iv) and are all inert organic solvents, where preferably ethers such as tetrahydrofuran, 1,4-dioxane, diethyl ether and 1,2-dimethoxyethane can be used. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes. The reaction temperature is preferably between −30° C. and 80° C., in particular between −10° C. and 60° C. It may be preferred to work at temperatures of −5° C. to 20° C. or 0° C. to 40° C.

The reaction is generally carried out under atmospheric pressure.

The electrophile, in particular the disulfide or BrSCN, is usually employed in equivalent amount compared to of the compound (IIIa) and/or (IIIb) or in excess, such that usually 1 to 8 moles, in particular 2 to 6 or 3 to 5 moles are used per mole of the compound (IIIa) and/or (IIIb).

In case a work-up is suitable, it can be carried out according to procedures generally known to the person skilled in the art. Usually, the reaction mixture is extracted with a suitable organic solvent, and the residue is, if appropriate, purified by recrystallization and/or chromatography.

Furthermore, it is possible by means of the inventive process as described above to insert a group S-$M^{14}$, (Y=$M^{14}$ in compounds (I)) wherein $M^{14}$ is defined as below.

Compounds of formula (IIa) are novel. Accordingly, a further aspect of the present invention is compound of formula (IIa)

wherein X is halogen, in particular Br or Cl, and R is as defined or preferably defined above, wherein R=group (1), (2), (3), (4) or (5) is preferred.

According to one specific embodiment, R in compounds (IIa) is a group (1) as defined above, including the specific embodiments thereof. In particular, compounds (X)-(1),

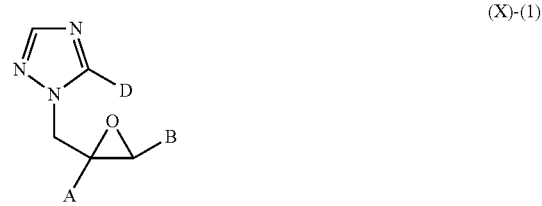

wherein D is SMgX, according to the invention compiled in tables 1a to 138a in combination with rows 299 to 596 of table A below are precursors (IIa) that are particularly suitable for the synthesis of the respective fungicides of formula (I)-(1) and/or that are obtained by the inventive process. According to a further specific embodiment, R in compounds (IIIa) is a group (1) as defined above, including the specific embodiments thereof. In particular, compounds (X)-(1), wherein D is MgX, according to the invention compiled in tables 1a to 138a in combination with rows 1 to 298 and 597 to 745 of table A below are precursors (IIIa) that are particularly suitable for the synthesis of the respective fungicides of formula (I)-(1) and/or that are obtained by the inventive process. The groups mentioned for a substituent in the tables are furthermore per se, independently of the combination in which they are mentioned, a particularly preferred aspect of the substituent in question.

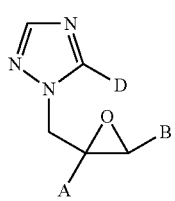
(X)-(1)

table 1a
Compounds (X)-(1), wherein A is 2,3-difluorophenyl and the combination of B and D corresponds in each case to one row of table A (Compounds (X)-(1).1aA-1 to (X)(1).1aA-745)

table 2a
Compounds (X)-(1), wherein A is 2,4-difluorophenyl and the combination of B and D corresponds in each case to one row of table A (Compounds (X)-(1).2aA-1 to (X)(1).2aA-745)

table 3a
Compounds (X)-(1), wherein A is 2,5-difluorophenyl and the combination of B and D corresponds in each case to one row of table A (Compounds (X)-(1).3aA-1 to (X)(1).3aA-745)

table 4a
Compounds (X)-(1), wherein A is 2,6-difluorophenyl and the combination of B and D corresponds in each case to one row of table A (Compounds (X)-(1).4aA-1 to (X)(1).4aA-745)

table 5a
Compounds (X)-(1), wherein A is 3,4-difluorophenyl and the combination of B and D corresponds in each case to one row of table A (Compounds (X)-(1).5aA-1 to (X)(1).5aA-745)

table 6a
Compounds (X)-(1), wherein A is 3,5-difluorophenyl and the combination of B and D corresponds in each case to one row of table A (Compounds (X)-(1).6aA-1 to (X)(1).6aA-745)

table 7a
Compounds (X)-(1), wherein A is 2-fluoro-3-chlorophenyl and the combination of B and D corresponds in each case to one row of table A (Compounds (X)-(1).7aA-1 to (X)-(1).7aA-745)

table 8a
Compounds (X)-(1), wherein A is 2-fluoro-4-chlorophenyl and the combination of B and D corresponds in each case to one row of table A (Compounds (X)-(1).8aA-1 to (X)-(1).8aA-745)

table 9a
Compounds (X)-(1), wherein A is 2-fluoro-5-chlorophenyl and the combination of B and D corresponds in each case to one row of table A (Compounds (X)-(1).9aA-1 to (X)-(1).9aA-745)

table 10a
Compounds (X)-(1), wherein A is 2-fluoro-6-chlorophenyl and the combination of B and D corresponds in each case to one row of table A (Compounds (X)-(1).10aA-1 to (X)-(1).10aA-745)

table 11a
Compounds (X)-(1), wherein A is 3-fluoro-4-chlorophenyl and the combination of B and D corresponds in each case to one row of table A (Compounds (X)-(1).11aA-1 to (X)-(1).11aA-745)

table 12a
Compounds (X)-(1), wherein A is 3-fluoro-5-chlorophenyl and the combination of B and D corresponds in each case to one row of table A (Compounds (X)-(1).12aA-1 to (X)-(1).12aA-745)

table 13a
Compounds (X)-(1), wherein A is 2-chloro-3-fluorophenyl and the combination of B and D corresponds in each case to one row of table A (Compounds (X)-(1).13aA-1 to (X)-(1).13aA-745)

table 14a
Compounds (X)-(1), wherein A is 2-chloro-4-fluorophenyl and the combination of B and D corresponds in each case to one row of table A (Compounds (X)-(1).14aA-1 to (X)-(1).14aA-745)

table 15a
Compounds (X)-(1), wherein A is 2-chloro-5-fluorophenyl and the combination of B and D corresponds in each case to one row of table A (Compounds (X)-(1).15aA-1 to (X)-(1).15aA-745)

table 16a
Compounds (X)-(1), wherein A is 3-chloro-4-fluorophenyl and the combination of B and D corresponds in each case to one row of table A (Compounds (X)-(1).16aA-1 to (X)-(1).16aA-745)

table 17a
Compounds (X)-(1), wherein A is 2-methyl-3-fluorophenyl and the combination of B and D corresponds in each case to one row of table A (Compounds (X)-(1).17aA-1 to (X)-(1).17aA-745)

table 18a
Compounds (X)-(1), wherein A is 2-methyl-4-fluorophenyl and the combination of B and D corresponds in each case to one row of table A (Compounds (X)-(1).18aA-1 to (X)-(1).18aA-745)

table 19a
Compounds (X)-(1), wherein A is 2-methyl-5-fluorophenyl and the combination of B and D corresponds in each case to one row of table A (Compounds (X)-(1).19aA-1 to (X)-(1).19aA-745)

table 20a
Compounds (X)-(1), wherein A is 2-methyl-6-fluorophenyl and the combination of B and D corresponds in each case to one row of table A (Compounds (X)-(1).20aA-1 to (X)-(1).20aA-745)

table 21a
Compounds (X)-(1), wherein A is 3-methyl-4-fluorophenyl and the combination of B and D corresponds in each case to one row of table A (Compounds (X)-(1).21aA-1 to (X)-(1).21aA-745)

table 22a
Compounds (X)-(1), wherein A is 3-methyl-5-fluorophenyl and the combination of B and D corresponds in each case to one row of table A (Compounds (X)-(1).22aA-1 to (X)-(1).22aA-745)

table 23a
Compounds (X)-(1), wherein A is 2-fluoro-3-methylphenyl and the combination of B and D corresponds in each case to one row of table A (Compounds (X)-(1).23aA-1 to (X)-(1).23aA-745)

table 24a
Compounds (X)-(1), wherein A is 2-fluoro-4-methylphenyl and the combination of B and D corresponds in each case to one row of table A (Compounds (X)-(1).24aA-1 to (X)-(1).24aA-745)

table 25a
Compounds (X)-(1), wherein A is 2-fluoro-5-methylphenyl and the combination of B and D corresponds in each case to one row of table A (Compounds (X)-(1).25aA-1 to (X)-(1).25aA-745)

table 26a
Compounds (X)-(1), wherein A is 3-fluoro-4-methylphenyl and the combination of B and D corresponds in each case to one row of table A (Compounds (X)-(1).26aA-1 to (X)-(1).26aA-745)

table 27a aA-745aA-745aA-745aA-745aA-745aA-745aA-745aA-745aA-745aA-745
Compounds (X)-(1), wherein A is 2-methoxy-3-fluorophenyl and the combination of B and D corresponds in each case to one row of table A (Compounds (X)-(1).27aA-1 to (X)-(1).27aA-745)

table 28a
Compounds (X)-(1), wherein A is 2-methoxy-4-fluorophenyl and the combination of B and D corresponds in each case to one row of table A (Compounds (X)-(1).28aA-1 to (X)-(1).28aA-745)

table 29a
Compounds (X)-(1), wherein A is 2-methoxy-5-fluorophenyl and the combination of B and D corresponds in each case to one row of table A (Compounds (X)-(1).29aA-1 to (X)-(1).29aA-745)

table 30a
Compounds (X)-(1), wherein A is 2-methoxy-6-fluorophenyl and the combination of B and D corresponds in each case to one row of table A (Compounds (X)-(1).30aA-1 to (X)-(1).30aA-745)

table 31a
Compounds (X)-(1), wherein A is 3-methoxy-4-fluorophenyl and the combination of B and D corresponds in each case to one row of table A (Compounds (X)-(1).31aA-1 to (X)-(1).31aA-745)

table 32a
Compounds (X)-(1), wherein A is 3-methoxy-5-fluorophenyl and the combination of B and D corresponds in each case to one row of table A (Compounds (X)-(1).32aA-1 to (X)-(1).32aA-745)

table 33a
Compounds (X)-(1), wherein A is 2-fluoro-3-methoxyphenyl and the combination of B and D corresponds in each case to one row of table A (Compounds (X)-(1).33aA-1 to (X)-(1).33aA-745)

table 34a
Compounds (X)-(1), wherein A is 2-fluoro-4-methoxyphenyl and the combination of B and D corresponds in each case to one row of table A (Compounds (X)-(1).34aA-1 to (X)-(1).34aA-745)

table 35a
Compounds (X)-(1), wherein A is 2-fluoro-5-methoxyphenyl and the combination of B and D corresponds in each case to one row of table A (Compounds (X)-(1).35aA-1 to (X)-(1).35aA-745)

table 36a
Compounds (X)-(1), wherein A is 3-fluoro-4-methoxyphenyl and the combination of B and D corresponds in each case to one row of table A (Compounds (X)-(1).36aA-1 to (X)-(1).36aA-745)

table 37a
Compounds (X)-(1), wherein A is 3-fluoro-5-methoxyphenyl and the combination of B and D corresponds in each case to one row of table A (Compounds (X)-(1).37aA-1 to (X)-(1).37aA-745)

table 38a
Compounds (X)-(1), wherein A is 2-(difluoromethoxy)-3-fluorophenyl and the combination of B and D corresponds in each case to one row of table A (Compounds (X)-(1).38aA-1 to (X)-(1).38aA-745)

table 39a
Compounds (X)-(1), wherein A is 2-(difluoromethoxy)-4-fluorophenyl and the combination of B and D corresponds in each case to one row of table A (Compounds (X)-(1).39aA-1 to (X)-(1).39aA-745)

table 40a
Compounds (X)-(1), wherein A is 2-(difluoromethoxy)-5-fluorophenyl and the combination of B and D corresponds in each case to one row of table A (Compounds (X)-(1).40aA-1 to (X)-(1).40aA-745)

table 41a
Compounds (X)-(1), wherein A is 2-(difluoromethoxy)-6-fluorophenyl and the combination of B and D corresponds in each case to one row of table A (Compounds (X)-(1).41aA-1 to (X)-(1).41aA-745)

table 42a
Compounds (X)-(1), wherein A is 3-(difluoromethoxy)-4-fluorophenyl and the combination of B and D corresponds in each case to one row of table A (Compounds (X)-(1).42aA-1 to (X)-(1).42aA-745)

table 43a
Compounds (X)-(1), wherein A is 3-(difluoromethoxy)-5-fluorophenyl and the combination of B and D corresponds in each case to one row of table A (Compounds (X)-(1).43aA-1 to (X)-(1).43aA-745)

table 44a
Compounds (X)-(1), wherein A is 2-fluoro-3-(difluoromethoxy)phenyl and the combination of B and D corresponds in each case to one row of table A (Compounds (X)-(1).44aA-1 to (X)-(1).44aA-745)

table 45a
Compounds (X)-(1), wherein A is 2-fluoro-4-(difluoromethoxy)phenyl and the combination of B and D corresponds in each case to one row of table A (Compounds (X)-(1).45aA-1 to (X)-(1).45aA-745)

table 46a
Compounds (X)-(1), wherein A is 2-fluoro-5-(difluoromethoxy)phenyl and the combination of B and D corresponds in each case to one row of table A (Compounds (X)-(1).46aA-1 to (X)-(1).46aA-745)

table 47a
Compounds (X)-(1), wherein A is 3-fluoro-4-(difluoromethoxy)phenyl and the combination of B and D corresponds in each case to one row of table A (Compounds (X)-(1).47aA-1 to (X)-(1).47aA-745)

table 48a
Compounds (X)-(1), wherein A is 2,3,4-trifluorophenyl and the combination of B and D corresponds in each case to one row of table A (Compounds (X)(1).48aA-1 to (X)-(1).48aA-745)

table 49a
Compounds (X)-(1), wherein A is 2,3,5-trifluorophenyl and the combination of B and D corresponds in each case to one row of table A (Compounds (X)-(1).49aA-1 to (X)-(1).49aA-745)

table 50a
Compounds (X)-(1), wherein A is 2,3,6-trifluorophenyl and the combination of B and D corresponds in each case to one row of table A (Compounds (X)-(1).50aA-1 to (X)-(1).50aA-745)

table 51a
Compounds (X)-(1), wherein A is 2,4,5-trifluorophenyl and the combination of B and D corresponds in each case to one row of table A (Compounds (X)-(1).51 aA-1 to (X)-(1).51aA-745)

table 52a
Compounds (X)-(1), wherein A is 2,4,6-trifluorophenyl and the combination of B and D corresponds in each case to one row of table A (Compounds (X)-(1).52aA-1 to (X)-(1).52aA-745)

table 53a
Compounds (X)-(1), wherein A is 3,4,5-trifluorophenyl and the combination of B and D corresponds in each case to one row of table A (Compounds (X)-(1).53aA-1 to (X)-(1).53aA-745)

table 54a
Compounds (X)-(1), wherein A is phenyl and the combination of B and D corresponds in each case to one row of table A (Compounds (X)-(1).54aA-1 to (X)(1).54aA-745)

table 55a
Compounds (X)-(1), wherein A is 2-chlorophenyl and the combination of B and D corresponds in each case to one row of table A (Compounds (X)-(1).55aA-1 to (X)(1).55aA-745)

table 56a
Compounds (X)-(1), wherein A is 3-chlorophenyl and the combination of B and D corresponds in each case to one row of table A (Compounds (X)-(1).56aA-1 to (X)(1).56aA-745)

table 57a
Compounds (X)-(1), wherein A is 4-chlorophenyl and the combination of B and D corresponds in each case to one row of table A (Compounds (X)-(1).57aA-1 to (X)(1).57aA-745)

table 58a
Compounds (X)-(1), wherein A is 2-fluorophenyl and the combination of B and D corresponds in each case to one row of table A (Compounds (X)-(1).58aA-1 to (X)(1).58aA-745)

table 59a
Compounds (X)-(1), wherein A is 3-fluorophenyl and the combination of B and D corresponds in each case to one row of table A (Compounds (X)-(1).59aA-1 to (X)(1).59aA-745)

table 60a
Compounds (X)-(1), wherein A is 4-fluorophenyl and the combination of B and D corresponds in each case to one row of table A (Compounds (X)-(1).60aA-1 to (X)(1).60aA-745)

table 61a
Compounds (X)-(1), wherein A is 2-methylphenyl and the combination of B and D corresponds in each case to one row of table A (Compounds (X)-(1).61aA-1 to (X)(1).61aA-745)

table 62a v
Compounds (X)-(1), wherein A is 3-methylphenyl and the combination of B and D corresponds in each case to one row of table A (Compounds (X)-(1).62aA-1 to (X)(1).62aA-745)

table 63a
Compounds (X)-(1), wherein A is 4-methylphenyl and the combination of B and D corresponds in each case to one row of table A (Compounds (X)-(1).63aA-1 to (X)(1).63aA-745)

table 64a
Compounds (X)-(1), wherein A is 2-methoxyphenyl and the combination of B and D corresponds in each case to one row of table A (Compounds (X)-(1).64aA-1 to (X)(1).64aA-745)

table 65a
Compounds (X)-(1), wherein A is 3-methoxyphenyl and the combination of B and D corresponds in each case to one row of table A (Compounds (X)-(1).65aA-1 to (X)(1).65aA-745)

table 66a
Compounds (X)-(1), wherein A is 4-methoxyphenyl and the combination of B and D corresponds in each case to one row of table A (Compounds (X)-(1).66aA-1 to (X)(1).66aA-745)

table 67a
Compounds (X)-(1), wherein A is 2-trifluoromethylphenyl and the combination of B and D corresponds in each case to one row of table A (Compounds (X)-(1).67aA-1 to (X)-(1).67aA-745)

table 68a
Compounds (X)-(1), wherein A is 3-trifluoromethylphenyl and the combination of B and D corresponds in each case to one row of table A (Compounds (X)-(1).68aA-1 to (X)-(1).68aA-745)

table 69a
Compounds (X)-(1), wherein A is 4-trifluoromethylphenyl and the combination of B and D corresponds in each case to one row of table A (Compounds (X)-(1).69aA-1 to (X)-(1).69aA-745)

table 70a
Compounds (X)-(1), wherein A is 2-difluoromethoxyphenyl and the combination of B and D corresponds in each case to one row of table A (Compounds (X)-(1).70aA-1 to (X)-(1).70aA-745)

table 71a
Compounds (X)-(1), wherein A is 3-difluoromethoxyphenyl and the combination of B and D corresponds in each case to one row of table A (Compounds (X)-(1).71aA-1 to (X)-(1).71aA-745)

table 72a
Compounds (X)-(1), wherein A is 4-difluoromethoxyphenyl and the combination of B and D corresponds in each case to one row of table A (Compounds (X)-(1).72aA-1 to (X)-(1).72aA-745)

table 73a
Compounds (X)-(1), wherein A is 2,3-dichlorophenyl and the combination of B and D corresponds in each case to one row of table A (Compounds (X)-(1).73aA-1 to (X)-(1).73aA-745)

table 74a
Compounds (X)-(1), wherein A is 2,4-dichlorophenyl and the combination of B and D corresponds in each case to one row of table A (Compounds (X)-(1).74aA-1 to (X)-(1).74aA-745)

table 75a
Compounds (X)-(1), wherein A is 2,5-dichlorophenyl and the combination of B and D corresponds in each case to one row of table A (Compounds (X)-(1).75aA-1 to (X)-(1).75aA-745)

table 76a
Compounds (X)-(1), wherein A is 2,6-dichlorophenyl and the combination of B and D corresponds in each case to one row of table A (Compounds (X)-(1).76aA-1 to (X)-(1).76aA-745)

table 77a
Compounds (X)-(1), wherein A is 3,4-dichlorophenyl and the combination of B and D corresponds in each case to one row of table A (Compounds (X)-(1).77aA-1 to (X)-(1).77aA-745)

table 78a
Compounds (X)-(1), wherein A is 3,5-dichlorophenyl and the combination of B and D corresponds in each case to one row of table A (Compounds (X)-(1).78aA-1 to (X)-(1).78aA-745)

table 79a
Compounds (X)-(1), wherein A is 2,3-dimethylphenyl and the combination of B and D corresponds in each case to one row of table A (Compounds (X)-(1).79aA-1 to (X)-(1).79aA-745)

table 80a
Compounds (X)-(1), wherein A is 2,4-dimethylphenyl and the combination of B and D corresponds in each case to one row of table A (Compounds (X)-(1).80aA-1 to (X)-(1).80aA-745)

table 81a
Compounds (X)-(1), wherein A is 2,5-dimethylphenyl and the combination of B and D corresponds in each case to one row of table A (Compounds (X)-(1).81 aA-1 to (X)-(1).81aA-745)

table 82a
Compounds (X)-(1), wherein A is 2,6-dimethylphenyl and the combination of B and D corresponds in each case to one row of table A (Compounds (X)-(1).82aA-1 to (X)-(1).821aA-745)

table 83a
Compounds (X)-(1), wherein A is 3,4-dimethylphenyl and the combination of B and D corresponds in each case to one row of table A (Compounds (X)-(1).83aA-1 to (X)-(1).83aA-745)

table 84a
Compounds (X)-(1), wherein A is 3,5-dimethylphenyl and the combination of B and D corresponds in each case to one row of table A (Compounds (X)-(1).84aA-1 to (X)-(1).84aA-745)

table 85a
table 86a
Compounds (X)-(1), wherein A is 2,3-dimethoxyphenyl and the combination of B and D corresponds in each case to one row of table A (Compounds (X)-(1).86aA-1 to (X)-(1).86aA-745)

table 87a
Compounds (X)-(1), wherein A is 2,4-dimethoxyphenyl and the combination of B and D corresponds in each case to one row of table A (Compounds (X)-(1).87aA-1 to (X)-(1).87aA-745)

table 88a
Compounds (X)-(1), wherein A is 2,5-dimethoxyphenyl and the combination of B and D corresponds in each case to one row of table A (Compounds (X)-(1).88aA-1 to (X)-(1).88aA-745)

table 89a
Compounds (X)-(1), wherein A is 2,6-dimethoxyphenyl and the combination of B and D corresponds in each case to one row of table A (Compounds (X)-(1).89aA-1 to (X)-(1).89aA-745)

table 90a
Compounds (X)-(1), wherein A is 3,4-dimethoxyphenyl and the combination of B and D corresponds in each case to one row of table A (Compounds (X)-(1).90aA-1 to (X)-(1).90aA-745)

table 91a
Compounds (X)-(1), wherein A is 3,5-dimethoxyphenyl and the combination of B and D corresponds in each case to one row of table A (Compounds (X)-(1).91 aA-1 to (X)-(1).91aA-745)

table 92a aA-745
Compounds (X)-(1), wherein A is 2-methyl-3-chlorophenyl and the combination of B and D corresponds in each case to one row of table A (Compounds (X)-(1).92aA-1 to (X)-(1).92aA-745)

table 93a
Compounds (X)-(1), wherein A is 2-methyl-4-chlorophenyl and the combination of B and D corresponds in each case to one row of table A (Compounds (X)-(1).93aA-1 to (X)-(1).93aA-745)

table 94a
Compounds (X)-(1), wherein A is 2-methyl-5-chlorophenyl and the combination of B and D corresponds in each case to one row of table A (Compounds (X)-(1).94aA-1 to (X)-(1).94aA-745)

table 95a
Compounds (X)-(1), wherein A is 2-methyl-6-chlorophenyl and the combination of B and D corresponds in each case to one row of table A (Compounds (X)-(1).95aA-1 to (X)-(1).95aA-745)

table 96a
Compounds (X)-(1), wherein A is 3-methyl-4-chlorophenyl and the combination of B and D corresponds in each case to one row of table A (Compounds (X)-(1).96aA-1 to (X)-(1).96aA-745)

table 97a
Compounds (X)-(1), wherein A is 3-methyl-5-chlorophenyl and the combination of B and D corresponds in each case to one row of table A (Compounds (X)-(1).97aA-1 to (X)-(1).97aA-745)

table 98a
Compounds (X)-(1), wherein A is 2-chloro-3-methylphenyl and the combination of B and D corresponds in each case to one row of table A (Compounds (X)-(1).98aA-1 to (X)-(1).98aA-745)

table 99a
Compounds (X)-(1), wherein A is 2-chloro-4-methylphenyl and the combination of B and D corresponds in each case to one row of table A (Compounds (X)-(1).99aA-1 to (X)-(1).99aA-745)

table 100a
Compounds (X)-(1), wherein A is 2-chloro-5-methylphenyl and the combination of B and D corresponds in each case to one row of table A (Compounds (X)-(1).100aA-1 to (X)-(1).100aA-745)

table 101a
Compounds (X)-(1), wherein A is 3-chloro-4-methylphenyl and the combination of B and D corresponds in each case to one row of table A (Compounds (X)-(1).101aA-1 to (X)-(1).101aA-745)

table 102a
Compounds (X)-(1), wherein A is 2-methoxy-3-chlorophenyl and the combination of B and D corresponds in each case to one row of table A (Compounds (X)(1).102aA-1 to (X)-(1).102aA-745)

table 103a
Compounds (X)-(1), wherein A is 2-methoxy-4-chlorophenyl and the combination of B and D corresponds in each case to one row of table A (Compounds (X)(1).103aA-1 to (X)-(1).103aA-745)

table 104a
Compounds (X)-(1), wherein A is 2-methoxy-5-chlorophenyl and the combination of B and D corresponds in each case to one row of table A (Compounds (X)(1).104aA-1 to (X)-(1).104aA-745)

table 105a
Compounds (X)-(1), wherein A is 2-methoxy-6-chlorophenyl and the combination of B and D corresponds in each case to one row of table A (Compounds (X)(1).105aA-1 to (X)-(1).105aA-745)

table 106a
Compounds (X)-(1), wherein A is 3-methoxy-4-chlorophenyl and the combination of B and D corresponds in each case to one row of table A (Compounds (X)(1).106aA-1 to (X)-(1).106aA-745)

table 107a
Compounds (X)-(1), wherein A is 3-methoxy-5-chlorophenyl and the combination of B and D corresponds in each case to one row of table A (Compounds (X)(1).107aA-1 to (X)-(1).107aA-745)

table 108a
Compounds (X)-(1), wherein A is 2-chloro-3-methoxyphenyl and the combination of B and D corresponds in each case to one row of table A (Compounds (X)(1).108aA-1 to (X)-(1).108aA-745)

table 109a
Compounds (X)-(1), wherein A is 2-chloro-4-methoxyphenyl and the combination of B and D corresponds in each case to one row of table A (Compounds (X)(1).109aA-1 to (X)-(1).109aA-745)

table 110a
Compounds (X)-(1), wherein A is 2-chloro-5-methoxyphenyl and the combination of B and D corresponds in each case to one row of table A (Compounds (X)(1).110aA-1 to (X)-(1).110aA-745)

table 111a
Compounds (X)-(1), wherein A is 3-chloro-4-methoxyphenyl and the combination of B and D corresponds in each case to one row of table A (Compounds (X)(1).111aA-1 to (X)-(1).111aA-745)

table 112a
Compounds (X)-(1), wherein A is 2-(trifluoromethyl)-3-chlorophenyl and the combination of B and D corresponds in each case to one row of table A (Compounds (X)(1).112aA-1 to (X)-(1).112aA-745)

table 113a
Compounds (X)-(1), wherein A is 2-(trifluoromethyl)-4-chlorophenyl and the combination of B and D corresponds in each case to one row of table A (Compounds (X)(1).113aA-1 to (X)-(1).113aA-745)

table 114a
Compounds (X)-(1), wherein A is 2-(trifluoromethyl)-5-chlorophenyl and the combination of B and D corresponds in each case to one row of table A (Compounds (X)(1).114aA-1 to (X)-(1).114aA-745)

table 115a
Compounds (X)-(1), wherein A is 2-(trifluoromethyl)-6-chlorophenyl and the combination of B and D corresponds in each case to one row of table A (Compounds (X)(1).115aA-1 to (X)-(1).115aA-745)

table 116a
Compounds (X)-(1), wherein A is 3-(trifluoromethyl)-4-chlorophenyl and the combination of B and D corresponds in each case to one row of table A (Compounds (X)(1).116aA-1 to (X)-(1).116aA-745)

table 117a
Compounds (X)-(1), wherein A is 3-(trifluoromethyl)-5-chlorophenyl and the combination of B and D corresponds in each case to one row of table A (Compounds (X)(1).117aA-1 to (X)-(1).117aA-745)

table 118a
Compounds (X)-(1), wherein A is 2-chloro-3-(trifluoromethyl)phenyl and the combination of B and D corresponds in each case to one row of table A (Compounds (X)(1).118aA-1 to (X)-(1).118aA-745)

table 119a
Compounds (X)-(1), wherein A is 2-chloro-4-(trifluoromethyl)phenyl and the combination of B and D corresponds in each case to one row of table A (Compounds (X)(1).119aA-1 to (X)-(1).119aA-745)

table 120a
Compounds (X)-(1), wherein A is 2-chloro-5-(trifluoromethyl)phenyl and the combination of B and D corresponds in each case to one row of table A (Compounds (X)(1).120aA-1 to (X)-(1).120aA-745)

table 121a
Compounds (X)-(1), wherein A is 3-chloro-4-(trifluoromethyl)phenyl and the combination of B and D corresponds in each case to one row of table A (Compounds (X)(1).121aA-1 to (X)-(1).121aA-745)

table 122a
Compounds (X)-(1), wherein A is 2-(trifluoromethoxy)-3-chlorophenyl and the combination of B and D corresponds in each case to one row of table A (Compounds (X)-(1).122aA-1 to (X)-(1).122aA-745)

table 123a
Compounds (X)-(1), wherein A is 2-(difluoromethoxy)-3-chlorophenyl and the combination of B and D corresponds in each case to one row of table A (Compounds (X)-(1).123aA-1 to (X)-(1).123aA-745)

table 124a
Compounds (X)-(1), wherein A is 2-(difluoromethoxy)-4-chlorophenyl and the combination of B and D corresponds in each case to one row of table A (Compounds (X)-(1).124aA-1 to (X)-(1).124aA-745)

table 125a
Compounds (X)-(1), wherein A is 2-(difluoromethoxy)-5-chlorophenyl and the combination of B and D corresponds in each case to one row of table A (Compounds (X)-(1).125aA-1 to (X)-(1).125aA-745)

table 126a
Compounds (X)-(1), wherein A is 2-(difluoromethoxy)-6-chlorophenyl and the combination of B and D corresponds in each case to one row of table A (Compounds (X)-(1).126aA-1 to (X)-(1).126aA-745)

table 127a
Compounds (X)-(1), wherein A is 3-(difluoromethoxy)-4-chlorophenyl and the combination of B and D corresponds in each case to one row of table A (Compounds (X)-(1).127aA-1 to (X)-(1).127aA-745)

table 128a
Compounds (X)-(1), wherein A is 3-(difluoromethoxy)-5-chlorophenyl and the combination of B and D corresponds in each case to one row of table A (Compounds (X)-(1).128aA-1 to (X)-(1).128aA-745)

table 129a
Compounds (X)-(1), wherein A is 2-chloro-3-(difluoromethoxy)phenyl and the combination of B and D corresponds in each case to one row of table A (Compounds (X)-(1).129aA-1 to (X)-(1).129aA-745)

table 130a
Compounds (X)-(1), wherein A is 2-chloro-4-(difluoromethoxy)phenyl and the combination of B and D corresponds in each case to one row of table A (Compounds (X)-(1).130aA-1 to (X)-(1).130aA-745)

table 131a
Compounds (X)-(1), wherein A is 2-chloro-5-(difluoromethoxy)phenyl and the combination of B and D corresponds in each case to one row of table A (Compounds (X)-(1).131aA-1 to (X)-(1).131aA-745)

table 132a
Compounds (X)-(1), wherein A is 3-chloro-4-(difluoromethoxy)phenyl and the combination of B and D corresponds in each case to one row of table A (Compounds (X)-(1).132aA-1 to (X)-(1).132aA-745)

table 133a
Compounds (X)-(1), wherein A is 2,3,4-trichlorophenyl and the combination of B and D corresponds in each case to one row of table A (Compounds (X)-(1).133aA-1 to (X)-(1).133aA-745)

table 134a
Compounds (X)-(1), wherein A is 2,3,5-trichlorophenyl and the combination of B and D corresponds in each case to one row of table A (Compounds (X)-(1).134aA-1 to (X)-(1).134aA-745)

table 135a
Compounds (X)-(1), wherein A is 2,3,6-trichlorophenyl and the combination of B and D corresponds in each case to one row of table A (Compounds (X)-(1).135aA-1 to (X)-(1).135aA-745)

table 136a
Compounds (X)-(1), wherein A is 2,4,5-trichlorophenyl and the combination of B and D corresponds in each case to one row of table A (Compounds (X)-(1).136aA-1 to (X)-(1).136aA-745)

table 137a
Compounds (X)-(1), wherein A is 2,4,6-trichlorophenyl and the combination of B and D corresponds in each case to one row of table A (Compounds (X)-(1).137aA-1 to (X)-(1).137aA-745)

table 138a
Compounds (X)-(1), wherein A is 3,4,5-trichlorophenyl and the combination of B and D corresponds in each case to one row of table A (Compounds (X)-(1).138aA-1 to (X)-(1).138aA-745)

TABLE A

| row | B | D |
| --- | --- | --- |
| A-1 | phenyl | MgCl |
| A-2 | 2-chlorophenyl | MgCl |
| A-3 | 3-chlorophenyl | MgCl |
| A-4 | 4-chlorophenyl | MgCl |
| A-5 | 2-fluorophenyl | MgCl |
| A-6 | 3-fluorophenyl | MgCl |
| A-7 | 4-fluorophenyl | MgCl |
| A-8 | 2-methylphenyl | MgCl |
| A-9 | 3-methylphenyl | MgCl |
| A-10 | 4-methylphenyl | MgCl |
| A-11 | 2-ethylphenyl | MgCl |
| A-12 | 3-ethylphenyl | MgCl |
| A-13 | 4-ethylphenyl | MgCl |
| A-14 | 2-methoxyphenyl | MgCl |
| A-15 | 3-methoxyphenyl | MgCl |
| A-16 | 4-methoxyphenyl | MgCl |
| A-17 | 2-trifluoromethylphenyl | MgCl |
| A-18 | 3-trifluoromethylphenyl | MgCl |
| A-19 | 4-trifluoromethylphenyl | MgCl |
| A-20 | 2-trifluoromethoxyphenyl | MgCl |
| A-21 | 3-trifluoromethoxyphenyl | MgCl |
| A-22 | 4-trifluoromethoxyphenyl | MgCl |
| A-23 | 2-difluoromethoxyphenyl | MgCl |
| A-24 | 3-difluoromethoxyphenyl | MgCl |
| A-25 | 4-difluoromethoxyphenyl | MgCl |
| A-26 | 2-trifluoromethylthiophenyl | MgCl |
| A-27 | 3-trifluoromethylthiophenyl | MgCl |
| A-28 | 4-trifluoromethylthiophenyl | MgCl |
| A-29 | 2,3-dichlorophenyl | MgCl |
| A-30 | 2,4-dichlorophenyl | MgCl |
| A-31 | 2,5-dichlorophenyl | MgCl |
| A-32 | 2,6-dichlorophenyl | MgCl |
| A-33 | 3,4-dichlorophenyl | MgCl |
| A-34 | 3,5-dichlorophenyl | MgCl |
| A-35 | 2,3-difluorophenyl | MgCl |
| A-36 | 2,4-difluorophenyl | MgCl |
| A-37 | 2,5-difluorophenyl | MgCl |
| A-38 | 2,6-difluorophenyl | MgCl |
| A-39 | 3,4-difluorophenyl | MgCl |
| A-40 | 3,5-difluorophenyl | MgCl |
| A-41 | 2,3-dimethylphenyl | MgCl |
| A-42 | 2,4-dimethylphenyl | MgCl |
| A-43 | 2,5-dimethylphenyl | MgCl |
| A-44 | 2,6-dimethylphenyl | MgCl |
| A-45 | 3,4-dimethylphenyl | MgCl |
| A-46 | 3,5-dimethylphenyl | MgCl |
| A-47 | 2-fluoro-3-chlorophenyl | MgCl |
| A-48 | 2-fluoro-4-chlorophenyl | MgCl |
| A-49 | 2-fluoro-5-chlorophenyl | MgCl |
| A-50 | 2-fluoro-6-chlorophenyl | MgCl |
| A-51 | 3-fluoro-4-chlorophenyl | MgCl |
| A-52 | 3-fluoro-5-chlorophenyl | MgCl |
| A-53 | 2-chloro-3-fluorophenyl | MgCl |
| A-54 | 2-chloro-4-fluorophenyl | MgCl |
| A-55 | 2-chloro-5-fluorophenyl | MgCl |
| A-56 | 3-chloro-4-fluorophenyl | MgCl |
| A-57 | 2-methyl-3-chlorophenyl | MgCl |
| A-58 | 2-methyl-4-chlorophenyl | MgCl |
| A-59 | 2-methyl-5-chlorophenyl | MgCl |
| A-60 | 2-methyl-6-chlorophenyl | MgCl |
| A-61 | 3-methyl-4-chlorophenyl | MgCl |
| A-62 | 3-methyl-5-chlorophenyl | MgCl |
| A-63 | 2-chloro-3-methylphenyl | MgCl |
| A-64 | 2-chloro-4-methylphenyl | MgCl |
| A-65 | 2-chloro-5-methylphenyl | MgCl |
| A-66 | 3-chloro-4-methylphenyl | MgCl |
| A-67 | 2-methyl-3-fluorophenyl | MgCl |
| A-68 | 2-methyl-4-fluorophenyl | MgCl |
| A-69 | 2-methyl-5-fluorophenyl | MgCl |
| A-70 | 2-methyl-6-fluorophenyl | MgCl |
| A-71 | 3-methyl-4-fluorophenyl | MgCl |
| A-72 | 3-methyl-5-fluorophenyl | MgCl |
| A-73 | 2-fluoro-3-methylphenyl | MgCl |
| A-74 | 2-fluoro-4-methylphenyl | MgCl |
| A-75 | 2-fluoro-5-methylphenyl | MgCl |
| A-76 | 3-fluoro-4-methylphenyl | MgCl |
| A-77 | 2-chloro-3-ethylphenyl | MgCl |
| A-78 | 2-chloro-4-ethylphenyl | MgCl |
| A-79 | 2-chloro-5-ethylphenyl | MgCl |
| A-80 | 3-chloro-4-ethylphenyl | MgCl |
| A-81 | 2-ethyl-3-chlorophenyl | MgCl |
| A-82 | 2-ethyl-4-chlorophenyl | MgCl |
| A-83 | 2-ethyl-5-chlorophenyl | MgCl |
| A-84 | 2-ethyl-6-chlorophenyl | MgCl |
| A-85 | 3-ethyl-4-chlorophenyl | MgCl |
| A-86 | 3-ethyl-5-chlorophenyl | MgCl |
| A-87 | 2-ethyl-3-fluorophenyl | MgCl |
| A-88 | 2-ethyl-4-fluorophenyl | MgCl |
| A-89 | 2-ethyl-5-fluorophenyl | MgCl |
| A-90 | 2-ethyl-6-fluorophenyl | MgCl |
| A-91 | 3-ethyl-4-fluorophenyl | MgCl |
| A-92 | 3-ethyl-5-fluorophenyl | MgCl |

TABLE A-continued

| row | B | D |
|---|---|---|
| A-93 | 2-fluoro-3-ethylphenyl | MgCl |
| A-94 | 2-fluoro-4-ethylphenyl | MgCl |
| A-95 | 2-fluoro-5-ethylphenyl | MgCl |
| A-96 | 3-fluoro-4-ethylphenyl | MgCl |
| A-97 | 2-methoxy-3-chlorophenyl | MgCl |
| A-98 | 2-methoxy-4-chlorophenyl | MgCl |
| A-99 | 2-methoxy-5-chlorophenyl | MgCl |
| A-100 | 2-methoxy-6-chlorophenyl | MgCl |
| A-101 | 3-methoxy-4-chlorophenyl | MgCl |
| A-102 | 3-methoxy-5-chlorophenyl | MgCl |
| A-103 | 2-chloro-3-methoxyphenyl | MgCl |
| A-104 | 2-chloro-4-methoxyphenyl | MgCl |
| A-105 | 2-chloro-5-methoxyphenyl | MgCl |
| A-106 | 3-chloro-4-methoxyphenyl | MgCl |
| A-107 | 2-methoxy-3-fluorophenyl | MgCl |
| A-108 | 2-methoxy-4-fluorophenyl | MgCl |
| A-109 | 2-methoxy-5-fluorophenyl | MgCl |
| A-110 | 2-methoxy-6-fluorophenyl | MgCl |
| A-111 | 3-methoxy-4-fluorophenyl | MgCl |
| A-112 | 3-methoxy-5-fluorophenyl | MgCl |
| A-113 | 2-fluoro-3-methoxyphenyl | MgCl |
| A-114 | 2-fluoro-4-methoxyphenyl | MgCl |
| A-115 | 2-fluoro-5-methoxyphenyl | MgCl |
| A-116 | 3-fluoro-4-methoxyphenyl | MgCl |
| A-117 | 3-fluoro-5-methoxyphenyl | MgCl |
| A-118 | 2-(difluoromethoxy)-3-chlorophenyl | MgCl |
| A-119 | 2-(difluoromethoxy)-4-chlorophenyl | MgCl |
| A-120 | 2-(difluoromethoxy)-5-chlorophenyl | MgCl |
| A-121 | 2-(difluoromethoxy)-6-chlorophenyl | MgCl |
| A-122 | 3-(difluoromethoxy)-4-chlorophenyl | MgCl |
| A-123 | 3-(difluoromethoxy)-5-chlorophenyl | MgCl |
| A-124 | 2-chloro-3-(difluoromethoxy)phenyl | MgCl |
| A-125 | 2-chloro-4-(difluoromethoxy)phenyl | MgCl |
| A-126 | 2-chloro-5-(difluoromethoxy)phenyl | MgCl |
| A-127 | 3-chloro-4-(difluoromethoxy)phenyl | MgCl |
| A-128 | 2-(difluoromethoxy)-3-fluorophenyl | MgCl |
| A-129 | 2-(difluoromethoxy)-4-fluorophenyl | MgCl |
| A-130 | 2-(difluoromethoxy)-5-fluorophenyl | MgCl |
| A-131 | 2-(difluoromethoxy)-6-fluorophenyl | MgCl |
| A-132 | 3-(difluoromethoxy)-4-fluorophenyl | MgCl |
| A-133 | 3-(difluoromethoxy)-5-fluorophenyl | MgCl |
| A-134 | 2-fluoro-3-(difluoromethoxy)phenyl | MgCl |
| A-135 | 2-fluoro-4-(difluoromethoxy)phenyl | MgCl |
| A-136 | 2-fluoro-5-(difluoromethoxy)phenyl | MgCl |
| A-137 | 3-fluoro-4-(difluoromethoxy)phenyl | MgCl |
| A-138 | 2,3,4-trichlorophenyl | MgCl |
| A-139 | 2,3,5-trichlorophenyl | MgCl |
| A-140 | 2,3,6-trichlorophenyl | MgCl |
| A-141 | 2,4,5-trichlorophenyl | MgCl |
| A-142 | 2,4,6-trichlorophenyl | MgCl |
| A-143 | 3,4,5-trichlorophenyl | MgCl |
| A-144 | 2,3,4-trifluorophenyl | MgCl |
| A-145 | 2,3,5-trifluorophenyl | MgCl |
| A-146 | 2,3,6-trifluorophenyl | MgCl |
| A-147 | 2,4,5-trifluorophenyl | MgCl |
| A-148 | 2,4,6-trifluorophenyl | MgCl |
| A-149 | 3,4,5-trifluorophenyl | MgCl |
| A-150 | phenyl | MgBr |
| A-151 | 2-chlorophenyl | MgBr |
| A-152 | 3-chlorophenyl | MgBr |
| A-153 | 4-chlorophenyl | MgBr |
| A-154 | 2-fluorophenyl | MgBr |
| A-155 | 3-fluorophenyl | MgBr |
| A-156 | 4-fluorophenyl | MgBr |
| A-157 | 2-methylphenyl | MgBr |
| A-158 | 3-methylphenyl | MgBr |
| A-159 | 4-methylphenyl | MgBr |
| A-160 | 2-ethylphenyl | MgBr |
| A-161 | 3-ethylphenyl | MgBr |
| A-162 | 4-ethylphenyl | MgBr |
| A-163 | 2-methoxyphenyl | MgBr |
| A-164 | 3-methoxyphenyl | MgBr |
| A-165 | 4-methoxyphenyl | MgBr |
| A-166 | 2-trifluoromethylphenyl | MgBr |
| A-167 | 3-trifluoromethylphenyl | MgBr |
| A-168 | 4-trifluoromethylphenyl | MgBr |
| A-169 | 2-trifluoromethoxyphenyl | MgBr |
| A-170 | 3-trifluoromethoxyphenyl | MgBr |
| A-171 | 4-trifluoromethoxyphenyl | MgBr |
| A-172 | 2-difluoromethoxyphenyl | MgBr |
| A-173 | 3-difluoromethoxyphenyl | MgBr |
| A-174 | 4-difluoromethoxyphenyl | MgBr |
| A-175 | 2-trifluoromethylthiophenyl | MgBr |
| A-176 | 3-trifluoromethylthiophenyl | MgBr |
| A-177 | 4-trifluoromethylthiophenyl | MgBr |
| A-178 | 2,3-dichlorophenyl | MgBr |
| A-179 | 2,4-dichlorophenyl | MgBr |
| A-180 | 2,5-dichlorophenyl | MgBr |
| A-181 | 2,6-dichlorophenyl | MgBr |
| A-182 | 3,4-dichlorophenyl | MgBr |
| A-183 | 3,5-dichlorophenyl | MgBr |
| A-184 | 2,3-difluorophenyl | MgBr |
| A-185 | 2,4-difluorophenyl | MgBr |
| A-186 | 2,5-difluorophenyl | MgBr |
| A-187 | 2,6-difluorophenyl | MgBr |
| A-188 | 3,4-difluorophenyl | MgBr |
| A-189 | 3,5-difluorophenyl | MgBr |
| A-190 | 2,3-dimethylphenyl | MgBr |
| A-191 | 2,4-dimethylphenyl | MgBr |
| A-192 | 2,5-dimethylphenyl | MgBr |
| A-193 | 2,6-dimethylphenyl | MgBr |
| A-194 | 3,4-dimethylphenyl | MgBr |
| A-195 | 3,5-dimethylphenyl | MgBr |
| A-196 | 2-fluoro-3-chlorophenyl | MgBr |
| A-197 | 2-fluoro-4-chlorophenyl | MgBr |
| A-198 | 2-fluoro-5-chlorophenyl | MgBr |
| A-199 | 2-fluoro-6-chlorophenyl | MgBr |
| A-200 | 3-fluoro-4-chlorophenyl | MgBr |
| A-201 | 3-fluoro-5-chlorophenyl | MgBr |
| A-202 | 2-chloro-3-fluorophenyl | MgBr |
| A-203 | 2-chloro-4-fluorophenyl | MgBr |
| A-204 | 2-chloro-5-fluorophenyl | MgBr |
| A-205 | 3-chloro-4-fluorophenyl | MgBr |
| A-206 | 2-methyl-3-chlorophenyl | MgBr |
| A-207 | 2-methyl-4-chlorophenyl | MgBr |
| A-208 | 2-methyl-5-chlorophenyl | MgBr |
| A-209 | 2-methyl-6-chlorophenyl | MgBr |
| A-210 | 3-methyl-4-chlorophenyl | MgBr |
| A-211 | 3-methyl-5-chlorophenyl | MgBr |
| A-212 | 2-chloro-3-methylphenyl | MgBr |
| A-213 | 2-chloro-4-methylphenyl | MgBr |
| A-214 | 2-chloro-5-methylphenyl | MgBr |
| A-215 | 3-chloro-4-methylphenyl | MgBr |
| A-216 | 2-methyl-3-fluorophenyl | MgBr |
| A-217 | 2-methyl-4-fluorophenyl | MgBr |
| A-218 | 2-methyl-5-fluorophenyl | MgBr |
| A-219 | 2-methyl-6-fluorophenyl | MgBr |
| A-220 | 3-methyl-4-fluorophenyl | MgBr |
| A-221 | 3-methyl-5-fluorophenyl | MgBr |
| A-222 | 2-fluoro-3-methylphenyl | MgBr |
| A-223 | 2-fluoro-4-methylphenyl | MgBr |
| A-224 | 2-fluoro-5-methylphenyl | MgBr |
| A-225 | 3-fluoro-4-methylphenyl | MgBr |
| A-226 | 2-chloro-3-ethylphenyl | MgBr |
| A-227 | 2-chloro-4-ethylphenyl | MgBr |
| A-228 | 2-chloro-5-ethylphenyl | MgBr |
| A-229 | 3-chloro-4-ethylphenyl | MgBr |
| A-230 | 2-ethyl-3-chlorophenyl | MgBr |
| A-231 | 2-ethyl-4-chlorophenyl | MgBr |
| A-232 | 2-ethyl-5-chlorophenyl | MgBr |
| A-233 | 2-ethyl-6-chlorophenyl | MgBr |
| A-234 | 3-ethyl-4-chlorophenyl | MgBr |
| A-235 | 3-ethyl-5-chlorophenyl | MgBr |
| A-236 | 2-ethyl-3-fluorophenyl | MgBr |
| A-237 | 2-ethyl-4-fluorophenyl | MgBr |
| A-238 | 2-ethyl-5-fluorophenyl | MgBr |
| A-239 | 2-ethyl-6-fluorophenyl | MgBr |
| A-240 | 3-ethyl-4-fluorophenyl | MgBr |
| A-241 | 3-ethyl-5-fluorophenyl | MgBr |
| A-242 | 2-fluoro-3-ethylphenyl | MgBr |
| A-243 | 2-fluoro-4-ethylphenyl | MgBr |
| A-244 | 2-fluoro-5-ethylphenyl | MgBr |
| A-245 | 3-fluoro-4-ethylphenyl | MgBr |
| A-246 | 2-methoxy-3-chlorophenyl | MgBr |
| A-247 | 2-methoxy-4-chlorophenyl | MgBr |
| A-248 | 2-methoxy-5-chlorophenyl | MgBr |

TABLE A-continued

| row | B | D |
|---|---|---|
| A-249 | 2-methoxy-6-chlorophenyl | MgBr |
| A-250 | 3-methoxy-4-chlorophenyl | MgBr |
| A-251 | 3-methoxy-5-chlorophenyl | MgBr |
| A-252 | 2-chloro-3-methoxyphenyl | MgBr |
| A-253 | 2-chloro-4-methoxyphenyl | MgBr |
| A-254 | 2-chloro-5-methoxyphenyl | MgBr |
| A-255 | 3-chloro-4-methoxyphenyl | MgBr |
| A-256 | 2-methoxy-3-fluorophenyl | MgBr |
| A-257 | 2-methoxy-4-fluorophenyl | MgBr |
| A-258 | 2-methoxy-5-fluorophenyl | MgBr |
| A-259 | 2-methoxy-6-fluorophenyl | MgBr |
| A-260 | 3-methoxy-4-fluorophenyl | MgBr |
| A-261 | 3-methoxy-5-fluorophenyl | MgBr |
| A-262 | 2-fluoro-3-methoxyphenyl | MgBr |
| A-263 | 2-fluoro-4-methoxyphenyl | MgBr |
| A-264 | 2-fluoro-5-methoxyphenyl | MgBr |
| A-265 | 3-fluoro-4-methoxyphenyl | MgBr |
| A-266 | 3-fluoro-5-methoxyphenyl | MgBr |
| A-267 | 2-(difluoromethoxy)-3-chlorophenyl | MgBr |
| A-268 | 2-(difluoromethoxy)-4-chlorophenyl | MgBr |
| A-269 | 2-(difluoromethoxy)-5-chlorophenyl | MgBr |
| A-270 | 2-(difluoromethoxy)-6-chlorophenyl | MgBr |
| A-271 | 3-(difluoromethoxy)-4-chlorophenyl | MgBr |
| A-272 | 3-(difluoromethoxy)-5-chlorophenyl | MgBr |
| A-273 | 2-chloro-3-(difluoromethoxy)phenyl | MgBr |
| A-274 | 2-chloro-4-(difluoromethoxy)phenyl | MgBr |
| A-275 | 2-chloro-5-(difluoromethoxy)phenyl | MgBr |
| A-276 | 3-chloro-4-(difluoromethoxy)phenyl | MgBr |
| A-277 | 2-(difluoromethoxy)-3-fluorophenyl | MgBr |
| A-278 | 2-(difluoromethoxy)-4-fluorophenyl | MgBr |
| A-279 | 2-(difluoromethoxy)-5-fluorophenyl | MgBr |
| A-280 | 2-(difluoromethoxy)-6-fluorophenyl | MgBr |
| A-281 | 3-(difluoromethoxy)-4-fluorophenyl | MgBr |
| A-282 | 3-(difluoromethoxy)-5-fluorophenyl | MgBr |
| A-283 | 2-fluoro-3-(difluoromethoxy)phenyl | MgBr |
| A-284 | 2-fluoro-4-(difluoromethoxy)phenyl | MgBr |
| A-285 | 2-fluoro-5-(difluoromethoxy)phenyl | MgBr |
| A-286 | 3-fluoro-4-(difluoromethoxy)phenyl | MgBr |
| A-287 | 2,3,4-trichlorophenyl | MgBr |
| A-288 | 2,3,5-trichlorophenyl | MgBr |
| A-289 | 2,3,6-trichlorophenyl | MgBr |
| A-290 | 2,4,5-trichlorophenyl | MgBr |
| A-291 | 2,4,6-trichlorophenyl | MgBr |
| A-292 | 3,4,5-trichlorophenyl | MgBr |
| A-293 | 2,3,4-trifluorophenyl | MgBr |
| A-294 | 2,3,5-trifluorophenyl | MgBr |
| A-295 | 2,3,6-trifluorophenyl | MgBr |
| A-296 | 2,4,5-trifluorophenyl | MgBr |
| A-297 | 2,4,6-trifluorophenyl | MgBr |
| A-298 | 3,4,5-trifluorophenyl | MgBr |
| A-299 | phenyl | SMgCl |
| A-300 | 2-chlorophenyl | SMgCl |
| A-301 | 3-chlorophenyl | SMgCl |
| A-302 | 4-chlorophenyl | SMgCl |
| A-303 | 2-fluorophenyl | SMgCl |
| A-304 | 3-fluorophenyl | SMgCl |
| A-305 | 4-fluorophenyl | SMgCl |
| A-306 | 2-methylphenyl | SMgCl |
| A-307 | 3-methylphenyl | SMgCl |
| A-308 | 4-methylphenyl | SMgCl |
| A-309 | 2-ethylphenyl | SMgCl |
| A-310 | 3-ethylphenyl | SMgCl |
| A-311 | 4-ethylphenyl | SMgCl |
| A-312 | 2-methoxyphenyl | SMgCl |
| A-313 | 3-methoxyphenyl | SMgCl |
| A-314 | 4-methoxyphenyl | SMgCl |
| A-315 | 2-trifluoromethylphenyl | SMgCl |
| A-316 | 3-trifluoromethylphenyl | SMgCl |
| A-317 | 4-trifluoromethylphenyl | SMgCl |
| A-318 | 2-trifluoromethoxyphenyl | SMgCl |
| A-319 | 3-trifluoromethoxyphenyl | SMgCl |
| A-320 | 4-trifluoromethoxyphenyl | SMgCl |
| A-321 | 2-difluoromethoxyphenyl | SMgCl |
| A-322 | 3-difluoromethoxyphenyl | SMgCl |
| A-323 | 4-difluoromethoxyphenyl | SMgCl |
| A-324 | 2-trifluoromethylthiophenyl | SMgCl |
| A-325 | 3-trifluoromethylthiophenyl | SMgCl |
| A-326 | 4-trifluoromethylthiophenyl | SMgCl |
| A-327 | 2,3-dichlorophenyl | SMgCl |
| A-328 | 2,4-dichlorophenyl | SMgCl |
| A-329 | 2,5-dichlorophenyl | SMgCl |
| A-330 | 2,6-dichlorophenyl | SMgCl |
| A-331 | 3,4-dichlorophenyl | SMgCl |
| A-332 | 3,5-dichlorophenyl | SMgCl |
| A-333 | 2,3-difluorophenyl | SMgCl |
| A-334 | 2,4-difluorophenyl | SMgCl |
| A-335 | 2,5-difluorophenyl | SMgCl |
| A-336 | 2,6-difluorophenyl | SMgCl |
| A-337 | 3,4-difluorophenyl | SMgCl |
| A-338 | 3,5-difluorophenyl | SMgCl |
| A-339 | 2,3-dimethylphenyl | SMgCl |
| A-340 | 2,4-dimethylphenyl | SMgCl |
| A-341 | 2,5-dimethylphenyl | SMgCl |
| A-342 | 2,6-dimethylphenyl | SMgCl |
| A-343 | 3,4-dimethylphenyl | SMgCl |
| A-344 | 3,5-dimethylphenyl | SMgCl |
| A-345 | 2-fluoro-3-chlorophenyl | SMgCl |
| A-346 | 2-fluoro-4-chlorophenyl | SMgCl |
| A-347 | 2-fluoro-5-chlorophenyl | SMgCl |
| A-348 | 2-fluoro-6-chlorophenyl | SMgCl |
| A-349 | 3-fluoro-4-chlorophenyl | SMgCl |
| A-350 | 3-fluoro-5-chlorophenyl | SMgCl |
| A-351 | 2-chloro-3-fluorophenyl | SMgCl |
| A-352 | 2-chloro-4-fluorophenyl | SMgCl |
| A-353 | 2-chloro-5-fluorophenyl | SMgCl |
| A-354 | 3-chloro-4-fluorophenyl | SMgCl |
| A-355 | 2-methyl-3-chlorophenyl | SMgCl |
| A-356 | 2-methyl-4-chlorophenyl | SMgCl |
| A-357 | 2-methyl-5-chlorophenyl | SMgCl |
| A-358 | 2-methyl-6-chlorophenyl | SMgCl |
| A-359 | 3-methyl-4-chlorophenyl | SMgCl |
| A-360 | 3-methyl-5-chlorophenyl | SMgCl |
| A-361 | 2-chloro-3-methylphenyl | SMgCl |
| A-362 | 2-chloro-4-methylphenyl | SMgCl |
| A-363 | 2-chloro-5-methylphenyl | SMgCl |
| A-364 | 3-chloro-4-methylphenyl | SMgCl |
| A-365 | 2-methyl-3-fluorophenyl | SMgCl |
| A-366 | 2-methyl-4-fluorophenyl | SMgCl |
| A-367 | 2-methyl-5-fluorophenyl | SMgCl |
| A-368 | 2-methyl-6-fluorophenyl | SMgCl |
| A-369 | 3-methyl-4-fluorophenyl | SMgCl |
| A-370 | 3-methyl-5-fluorophenyl | SMgCl |
| A-371 | 2-fluoro-3-methylphenyl | SMgCl |
| A-372 | 2-fluoro-4-methylphenyl | SMgCl |
| A-373 | 2-fluoro-5-methylphenyl | SMgCl |
| A-374 | 3-fluoro-4-methylphenyl | SMgCl |
| A-375 | 2-chloro-3-ethylphenyl | SMgCl |
| A-376 | 2-chloro-4-ethylphenyl | SMgCl |
| A-377 | 2-chloro-5-ethylphenyl | SMgCl |
| A-378 | 3-chloro-4-ethylphenyl | SMgCl |
| A-379 | 2-ethyl-3-chlorophenyl | SMgCl |
| A-380 | 2-ethyl-4-chlorophenyl | SMgCl |
| A-381 | 2-ethyl-5-chlorophenyl | SMgCl |
| A-382 | 2-ethyl-6-chlorophenyl | SMgCl |
| A-383 | 3-ethyl-4-chlorophenyl | SMgCl |
| A-384 | 3-ethyl-5-chlorophenyl | SMgCl |
| A-385 | 2-ethyl-3-fluorophenyl | SMgCl |
| A-386 | 2-ethyl-4-fluorophenyl | SMgCl |
| A-387 | 2-ethyl-5-fluorophenyl | SMgCl |
| A-388 | 2-ethyl-6-fluorophenyl | SMgCl |
| A-389 | 3-ethyl-4-fluorophenyl | SMgCl |
| A-390 | 3-ethyl-5-fluorophenyl | SMgCl |
| A-391 | 2-fluoro-3-ethylphenyl | SMgCl |
| A-392 | 2-fluoro-4-ethylphenyl | SMgCl |
| A-393 | 2-fluoro-5-ethylphenyl | SMgCl |
| A-394 | 3-fluoro-4-ethylphenyl | SMgCl |
| A-395 | 2-methoxy-3-chlorophenyl | SMgCl |
| A-396 | 2-methoxy-4-chlorophenyl | SMgCl |
| A-397 | 2-methoxy-5-chlorophenyl | SMgCl |
| A-398 | 2-methoxy-6-chlorophenyl | SMgCl |
| A-399 | 3-methoxy-4-chlorophenyl | SMgCl |
| A-400 | 3-methoxy-5-chlorophenyl | SMgCl |
| A-401 | 2-chloro-3-methoxyphenyl | SMgCl |
| A-402 | 2-chloro-4-methoxyphenyl | SMgCl |
| A-403 | 2-chloro-5-methoxyphenyl | SMgCl |
| A-404 | 3-chloro-4-methoxyphenyl | SMgCl |

TABLE A-continued

| row | B | D |
|---|---|---|
| A-405 | 2-methoxy-3-fluorophenyl | SMgCl |
| A-406 | 2-methoxy-4-fluorophenyl | SMgCl |
| A-407 | 2-methoxy-5-fluorophenyl | SMgCl |
| A-408 | 2-methoxy-6-fluorophenyl | SMgCl |
| A-409 | 3-methoxy-4-fluorophenyl | SMgCl |
| A-410 | 3-methoxy-5-fluorophenyl | SMgCl |
| A-411 | 2-fluoro-3-methoxyphenyl | SMgCl |
| A-412 | 2-fluoro-4-methoxyphenyl | SMgCl |
| A-413 | 2-fluoro-5-methoxyphenyl | SMgCl |
| A-414 | 3-fluoro-4-methoxyphenyl | SMgCl |
| A-415 | 3-fluoro-5-methoxyphenyl | SMgCl |
| A-416 | 2-(difluoromethoxy)-3-chlorophenyl | SMgCl |
| A-417 | 2-(difluoromethoxy)-4-chlorophenyl | SMgCl |
| A-418 | 2-(difluoromethoxy)-5-chlorophenyl | SMgCl |
| A-419 | 2-(difluoromethoxy)-6-chlorophenyl | SMgCl |
| A-420 | 3-(difluoromethoxy)-4-chlorophenyl | SMgCl |
| A-421 | 3-(difluoromethoxy)-5-chlorophenyl | SMgCl |
| A-422 | 2-chloro-3-(difluoromethoxy)phenyl | SMgCl |
| A-423 | 2-chloro-4-(difluoromethoxy)phenyl | SMgCl |
| A-424 | 2-chloro-5-(difluoromethoxy)phenyl | SMgCl |
| A-425 | 3-chloro-4-(difluoromethoxy)phenyl | SMgCl |
| A-426 | 2-(difluoromethoxy)-3-fluorophenyl | SMgCl |
| A-427 | 2-(difluoromethoxy)-4-fluorophenyl | SMgCl |
| A-428 | 2-(difluoromethoxy)-5-fluorophenyl | SMgCl |
| A-429 | 2-(difluoromethoxy)-6-fluorophenyl | SMgCl |
| A-430 | 3-(difluoromethoxy)-4-fluorophenyl | SMgCl |
| A-431 | 3-(difluoromethoxy)-5-fluorophenyl | SMgCl |
| A-432 | 2-fluoro-3-(difluoromethoxy)phenyl | SMgCl |
| A-433 | 2-fluoro-4-(difluoromethoxy)phenyl | SMgCl |
| A-434 | 2-fluoro-5-(difluoromethoxy)phenyl | SMgCl |
| A-435 | 3-fluoro-4-(difluoromethoxy)phenyl | SMgCl |
| A-436 | 2,3,4-trichlorophenyl | SMgCl |
| A-437 | 2,3,5-trichlorophenyl | SMgCl |
| A-438 | 2,3,6-trichlorophenyl | SMgCl |
| A-439 | 2,4,5-trichlorophenyl | SMgCl |
| A-440 | 2,4,6-trichlorophenyl | SMgCl |
| A-441 | 3,4,5-trichlorophenyl | SMgCl |
| A-442 | 2,3,4-trifluorophenyl | SMgCl |
| A-443 | 2,3,5-trifluorophenyl | SMgCl |
| A-444 | 2,3,6-trifluorophenyl | SMgCl |
| A-445 | 2,4,5-trifluorophenyl | SMgCl |
| A-446 | 2,4,6-trifluorophenyl | SMgCl |
| A-447 | 3,4,5-trifluorophenyl | SMgCl |
| A-448 | phenyl | SMgBr |
| A-449 | 2-chlorophenyl | SMgBr |
| A-450 | 3-chlorophenyl | SMgBr |
| A-451 | 4-chlorophenyl | SMgBr |
| A-452 | 2-fluorophenyl | SMgBr |
| A-453 | 3-fluorophenyl | SMgBr |
| A-454 | 4-fluorophenyl | SMgBr |
| A-455 | 2-methylphenyl | SMgBr |
| A-456 | 3-methylphenyl | SMgBr |
| A-457 | 4-methylphenyl | SMgBr |
| A-458 | 2-ethylphenyl | SMgBr |
| A-459 | 3-ethylphenyl | SMgBr |
| A-460 | 4-ethylphenyl | SMgBr |
| A-461 | 2-methoxyphenyl | SMgBr |
| A-462 | 3-methoxyphenyl | SMgBr |
| A-463 | 4-methoxyphenyl | SMgBr |
| A-464 | 2-trifluoromethylphenyl | SMgBr |
| A-465 | 3-trifluoromethylphenyl | SMgBr |
| A-466 | 4-trifluoromethylphenyl | SMgBr |
| A-467 | 2-trifluoromethoxyphenyl | SMgBr |
| A-468 | 3-trifluoromethoxyphenyl | SMgBr |
| A-469 | 4-trifluoromethoxyphenyl | SMgBr |
| A-470 | 2-difluoromethoxyphenyl | SMgBr |
| A-471 | 3-difluoromethoxyphenyl | SMgBr |
| A-472 | 4-difluoromethoxyphenyl | SMgBr |
| A-473 | 2-trifluoromethylthiophenyl | SMgBr |
| A-474 | 3-trifluoromethylthiophenyl | SMgBr |
| A-475 | 4-trifluoromethylthiophenyl | SMgBr |
| A-476 | 2,3-dichlorophenyl | SMgBr |
| A-477 | 2,4-dichlorophenyl | SMgBr |
| A-478 | 2,5-dichlorophenyl | SMgBr |
| A-479 | 2,6-dichlorophenyl | SMgBr |
| A-480 | 3,4-dichlorophenyl | SMgBr |
| A-481 | 3,5-dichlorophenyl | SMgBr |
| A-482 | 2,3-difluorophenyl | SMgBr |
| A-483 | 2,4-difluorophenyl | SMgBr |
| A-484 | 2,5-difluorophenyl | SMgBr |
| A-485 | 2,6-difluorophenyl | SMgBr |
| A-486 | 3,4-difluorophenyl | SMgBr |
| A-487 | 3,5-difluorophenyl | SMgBr |
| A-488 | 2,3-dimethylphenyl | SMgBr |
| A-489 | 2,4-dimethylphenyl | SMgBr |
| A-490 | 2,5-dimethylphenyl | SMgBr |
| A-491 | 2,6-dimethylphenyl | SMgBr |
| A-492 | 3,4-dimethylphenyl | SMgBr |
| A-493 | 3,5-dimethylphenyl | SMgBr |
| A-494 | 2-fluoro-3-chlorophenyl | SMgBr |
| A-495 | 2-fluoro-4-chlorophenyl | SMgBr |
| A-496 | 2-fluoro-5-chlorophenyl | SMgBr |
| A-497 | 2-fluoro-6-chlorophenyl | SMgBr |
| A-498 | 3-fluoro-4-chlorophenyl | SMgBr |
| A-499 | 3-fluoro-5-chlorophenyl | SMgBr |
| A-500 | 2-chloro-3-fluorophenyl | SMgBr |
| A-501 | 2-chloro-4-fluorophenyl | SMgBr |
| A-502 | 2-chloro-5-fluorophenyl | SMgBr |
| A-503 | 3-chloro-4-fluorophenyl | SMgBr |
| A-504 | 2-methyl-3-chlorophenyl | SMgBr |
| A-505 | 2-methyl-4-chlorophenyl | SMgBr |
| A-506 | 2-methyl-5-chlorophenyl | SMgBr |
| A-507 | 2-methyl-6-chlorophenyl | SMgBr |
| A-508 | 3-methyl-4-chlorophenyl | SMgBr |
| A-509 | 3-methyl-5-chlorophenyl | SMgBr |
| A-510 | 2-chloro-3-methylphenyl | SMgBr |
| A-511 | 2-chloro-4-methylphenyl | SMgBr |
| A-512 | 2-chloro-5-methylphenyl | SMgBr |
| A-513 | 3-chloro-4-methylphenyl | SMgBr |
| A-514 | 2-methyl-3-fluorophenyl | SMgBr |
| A-515 | 2-methyl-4-fluorophenyl | SMgBr |
| A-516 | 2-methyl-5-fluorophenyl | SMgBr |
| A-517 | 2-methyl-6-fluorophenyl | SMgBr |
| A-518 | 3-methyl-4-fluorophenyl | SMgBr |
| A-519 | 3-methyl-5-fluorophenyl | SMgBr |
| A-520 | 2-fluoro-3-methylphenyl | SMgBr |
| A-521 | 2-fluoro-4-methylphenyl | SMgBr |
| A-522 | 2-fluoro-5-methylphenyl | SMgBr |
| A-523 | 3-fluoro-4-methylphenyl | SMgBr |
| A-524 | 2-chloro-3-ethylphenyl | SMgBr |
| A-525 | 2-chloro-4-ethylphenyl | SMgBr |
| A-526 | 2-chloro-5-ethylphenyl | SMgBr |
| A-527 | 3-chloro-4-ethylphenyl | SMgBr |
| A-528 | 2-ethyl-3-chlorophenyl | SMgBr |
| A-529 | 2-ethyl-4-chlorophenyl | SMgBr |
| A-530 | 2-ethyl-5-chlorophenyl | SMgBr |
| A-531 | 2-ethyl-6-chlorophenyl | SMgBr |
| A-532 | 3-ethyl-4-chlorophenyl | SMgBr |
| A-533 | 3-ethyl-5-chlorophenyl | SMgBr |
| A-534 | 2-ethyl-3-fluorophenyl | SMgBr |
| A-535 | 2-ethyl-4-fluorophenyl | SMgBr |
| A-536 | 2-ethyl-5-fluorophenyl | SMgBr |
| A-537 | 2-ethyl-6-fluorophenyl | SMgBr |
| A-538 | 3-ethyl-4-fluorophenyl | SMgBr |
| A-539 | 3-ethyl-5-fluorophenyl | SMgBr |
| A-540 | 2-fluoro-3-ethylphenyl | SMgBr |
| A-541 | 2-fluoro-4-ethylphenyl | SMgBr |
| A-542 | 2-fluoro-5-ethylphenyl | SMgBr |
| A-543 | 3-fluoro-4-ethylphenyl | SMgBr |
| A-544 | 2-methoxy-3-chlorophenyl | SMgBr |
| A-545 | 2-methoxy-4-chlorophenyl | SMgBr |
| A-546 | 2-methoxy-5-chlorophenyl | SMgBr |
| A-547 | 2-methoxy-6-chlorophenyl | SMgBr |
| A-548 | 3-methoxy-4-chlorophenyl | SMgBr |
| A-549 | 3-methoxy-5-chlorophenyl | SMgBr |
| A-550 | 2-chloro-3-methoxyphenyl | SMgBr |
| A-551 | 2-chloro-4-methoxyphenyl | SMgBr |
| A-552 | 2-chloro-5-methoxyphenyl | SMgBr |
| A-553 | 3-chloro-4-methoxyphenyl | SMgBr |
| A-554 | 2-methoxy-3-fluorophenyl | SMgBr |
| A-555 | 2-methoxy-4-fluorophenyl | SMgBr |
| A-556 | 2-methoxy-5-fluorophenyl | SMgBr |
| A-557 | 2-methoxy-6-fluorophenyl | SMgBr |
| A-558 | 3-methoxy-4-fluorophenyl | SMgBr |
| A-559 | 3-methoxy-5-fluorophenyl | SMgBr |
| A-560 | 2-fluoro-3-methoxyphenyl | SMgBr |

TABLE A-continued

| row | B | D |
|---|---|---|
| A-561 | 2-fluoro-4-methoxyphenyl | SMgBr |
| A-562 | 2-fluoro-5-methoxyphenyl | SMgBr |
| A-563 | 3-fluoro-4-methoxyphenyl | SMgBr |
| A-564 | 3-fluoro-5-methoxyphenyl | SMgBr |
| A-565 | 2-(difluoromethoxy)-3-chlorophenyl | SMgBr |
| A-566 | 2-(difluoromethoxy)-4-chlorophenyl | SMgBr |
| A-567 | 2-(difluoromethoxy)-5-chlorophenyl | SMgBr |
| A-568 | 2-(difluoromethoxy)-6-chlorophenyl | SMgBr |
| A-569 | 3-(difluoromethoxy)-4-chlorophenyl | SMgBr |
| A-570 | 3-(difluoromethoxy)-5-chlorophenyl | SMgBr |
| A-571 | 2-chloro-3-(difluoromethoxy)phenyl | SMgBr |
| A-572 | 2-chloro-4-(difluoromethoxy)phenyl | SMgBr |
| A-573 | 2-chloro-5-(difluoromethoxy)phenyl | SMgBr |
| A-574 | 3-chloro-4-(difluoromethoxy)phenyl | SMgBr |
| A-575 | 2-(difluoromethoxy)-3-fluorophenyl | SMgBr |
| A-576 | 2-(difluoromethoxy)-4-fluorophenyl | SMgBr |
| A-577 | 2-(difluoromethoxy)-5-fluorophenyl | SMgBr |
| A-578 | 2-(difluoromethoxy)-6-fluorophenyl | SMgBr |
| A-579 | 3-(difluoromethoxy)-4-fluorophenyl | SMgBr |
| A-580 | 3-(difluoromethoxy)-5-fluorophenyl | SMgBr |
| A-581 | 2-fluoro-3-(difluoromethoxy)phenyl | SMgBr |
| A-582 | 2-fluoro-4-(difluoromethoxy)phenyl | SMgBr |
| A-583 | 2-fluoro-5-(difluoromethoxy)phenyl | SMgBr |
| A-584 | 3-fluoro-4-(difluoromethoxy)phenyl | SMgBr |
| A-585 | 2,3,4-trichlorophenyl | SMgBr |
| A-586 | 2,3,5-trichlorophenyl | SMgBr |
| A-587 | 2,3,6-trichlorophenyl | SMgBr |
| A-588 | 2,4,5-trichlorophenyl | SMgBr |
| A-589 | 2,4,6-trichlorophenyl | SMgBr |
| A-590 | 3,4,5-trichlorophenyl | SMgBr |
| A-591 | 2,3,4-trifluorophenyl | SMgBr |
| A-592 | 2,3,5-trifluorophenyl | SMgBr |
| A-593 | 2,3,6-trifluorophenyl | SMgBr |
| A-594 | 2,4,5-trifluorophenyl | SMgBr |
| A-595 | 2,4,6-trifluorophenyl | SMgBr |
| A-596 | 3,4,5-trifluorophenyl | SMgBr |
| A-597 | phenyl | MgI |
| A-598 | 2-chlorophenyl | MgI |
| A-599 | 3-chlorophenyl | MgI |
| A-600 | 4-chlorophenyl | MgI |
| A-601 | 2-fluorophenyl | MgI |
| A-602 | 3-fluorophenyl | MgI |
| A-603 | 4-fluorophenyl | MgI |
| A-604 | 2-methylphenyl | MgI |
| A-605 | 3-methylphenyl | MgI |
| A-606 | 4-methylphenyl | MgI |
| A-607 | 2-ethylphenyl | MgI |
| A-608 | 3-ethylphenyl | MgI |
| A-609 | 4-ethylphenyl | MgI |
| A-610 | 2-methoxyphenyl | MgI |
| A-611 | 3-methoxyphenyl | MgI |
| A-612 | 4-methoxyphenyl | MgI |
| A-613 | 2-trifluoromethylphenyl | MgI |
| A-614 | 3-trifluoromethylphenyl | MgI |
| A-615 | 4-trifluoromethylphenyl | MgI |
| A-616 | 2-trifluoromethoxyphenyl | MgI |
| A-617 | 3-trifluoromethoxyphenyl | MgI |
| A-618 | 4-trifluoromethoxyphenyl | MgI |
| A-619 | 2-difluoromethoxyphenyl | MgI |
| A-620 | 3-difluoromethoxyphenyl | MgI |
| A-621 | 4-difluoromethoxyphenyl | MgI |
| A-622 | 2-trifluoromethylthiophenyl | MgI |
| A-623 | 3-trifluoromethylthiophenyl | MgI |
| A-624 | 4-trifluoromethylthiophenyl | MgI |
| A-625 | 2,3-dichlorophenyl | MgI |
| A-626 | 2,4-dichlorophenyl | MgI |
| A-627 | 2,5-dichlorophenyl | MgI |
| A-628 | 2,6-dichlorophenyl | MgI |
| A-629 | 3,4-dichlorophenyl | MgI |
| A-630 | 3,5-dichlorophenyl | MgI |
| A-631 | 2,3-difluorophenyl | MgI |
| A-632 | 2,4-difluorophenyl | MgI |
| A-633 | 2,5-difluorophenyl | MgI |
| A-634 | 2,6-difluorophenyl | MgI |
| A-635 | 3,4-difluorophenyl | MgI |
| A-636 | 3,5-difluorophenyl | MgI |
| A-637 | 2,3-dimethylphenyl | MgI |
| A-638 | 2,4-dimethylphenyl | MgI |
| A-639 | 2,5-dimethylphenyl | MgI |
| A-640 | 2,6-dimethylphenyl | MgI |
| A-641 | 3,4-dimethylphenyl | MgI |
| A-642 | 3,5-dimethylphenyl | MgI |
| A-643 | 2-fluoro-3-chlorophenyl | MgI |
| A-644 | 2-fluoro-4-chlorophenyl | MgI |
| A-645 | 2-fluoro-5-chlorophenyl | MgI |
| A-646 | 2-fluoro-6-chlorophenyl | MgI |
| A-647 | 3-fluoro-4-chlorophenyl | MgI |
| A-648 | 3-fluoro-5-chlorophenyl | MgI |
| A-649 | 2-chloro-3-fluorophenyl | MgI |
| A-650 | 2-chloro-4-fluorophenyl | MgI |
| A-651 | 2-chloro-5-fluorophenyl | MgI |
| A-652 | 3-chloro-4-fluorophenyl | MgI |
| A-653 | 2-methyl-3-chlorophenyl | MgI |
| A-654 | 2-methyl-4-chlorophenyl | MgI |
| A-655 | 2-methyl-5-chlorophenyl | MgI |
| A-656 | 2-methyl-6-chlorophenyl | MgI |
| A-657 | 3-methyl-4-chlorophenyl | MgI |
| A-658 | 3-methyl-5-chlorophenyl | MgI |
| A-659 | 2-chloro-3-methylphenyl | MgI |
| A-660 | 2-chloro-4-methylphenyl | MgI |
| A-661 | 2-chloro-5-methylphenyl | MgI |
| A-662 | 3-chloro-4-methylphenyl | MgI |
| A-663 | 2-methyl-3-fluorophenyl | MgI |
| A-664 | 2-methyl-4-fluorophenyl | MgI |
| A-665 | 2-methyl-5-fluorophenyl | MgI |
| A-666 | 2-methyl-6-fluorophenyl | MgI |
| A-667 | 3-methyl-4-fluorophenyl | MgI |
| A-668 | 3-methyl-5-fluorophenyl | MgI |
| A-669 | 2-fluoro-3-methylphenyl | MgI |
| A-670 | 2-fluoro-4-methylphenyl | MgI |
| A-671 | 2-fluoro-5-methylphenyl | MgI |
| A-672 | 3-fluoro-4-methylphenyl | MgI |
| A-673 | 2-chloro-3-ethylphenyl | MgI |
| A-674 | 2-chloro-4-ethylphenyl | MgI |
| A-675 | 2-chloro-5-ethylphenyl | MgI |
| A-676 | 3-chloro-4-ethylphenyl | MgI |
| A-677 | 2-ethyl-3-chlorophenyl | MgI |
| A-678 | 2-ethyl-4-chlorophenyl | MgI |
| A-679 | 2-ethyl-5-chlorophenyl | MgI |
| A-680 | 2-ethyl-6-chlorophenyl | MgI |
| A-681 | 3-ethyl-4-chlorophenyl | MgI |
| A-682 | 3-ethyl-5-chlorophenyl | MgI |
| A-683 | 2-ethyl-3-fluorophenyl | MgI |
| A-684 | 2-ethyl-4-fluorophenyl | MgI |
| A-685 | 2-ethyl-5-fluorophenyl | MgI |
| A-686 | 2-ethyl-6-fluorophenyl | MgI |
| A-687 | 3-ethyl-4-fluorophenyl | MgI |
| A-688 | 3-ethyl-5-fluorophenyl | MgI |
| A-689 | 2-fluoro-3-ethylphenyl | MgI |
| A-690 | 2-fluoro-4-ethylphenyl | MgI |
| A-691 | 2-fluoro-5-ethylphenyl | MgI |
| A-692 | 3-fluoro-4-ethylphenyl | MgI |
| A-693 | 2-methoxy-3-chlorophenyl | MgI |
| A-694 | 2-methoxy-4-chlorophenyl | MgI |
| A-695 | 2-methoxy-5-chlorophenyl | MgI |
| A-696 | 2-methoxy-6-chlorophenyl | MgI |
| A-697 | 3-methoxy-4-chlorophenyl | MgI |
| A-698 | 3-methoxy-5-chlorophenyl | MgI |
| A-699 | 2-chloro-3-methoxyphenyl | MgI |
| A-700 | 2-chloro-4-methoxyphenyl | MgI |
| A-701 | 2-chloro-5-methoxyphenyl | MgI |
| A-702 | 3-chloro-4-methoxyphenyl | MgI |
| A-703 | 2-methoxy-3-fluorophenyl | MgI |
| A-704 | 2-methoxy-4-fluorophenyl | MgI |
| A-705 | 2-methoxy-5-fluorophenyl | MgI |
| A-706 | 2-methoxy-6-fluorophenyl | MgI |
| A-707 | 3-methoxy-4-fluorophenyl | MgI |
| A-708 | 3-methoxy-5-fluorophenyl | MgI |
| A-709 | 2-fluoro-3-methoxyphenyl | MgI |
| A-710 | 2-fluoro-4-methoxyphenyl | MgI |
| A-711 | 2-fluoro-5-methoxyphenyl | MgI |
| A-712 | 3-fluoro-4-methoxyphenyl | MgI |
| A-713 | 3-fluoro-5-methoxyphenyl | MgI |
| A-714 | 2-(difluoromethoxy)-3-chlorophenyl | MgI |
| A-715 | 2-(difluoromethoxy)-4-chlorophenyl | MgI |
| A-716 | 2-(difluoromethoxy)-5-chlorophenyl | MgI |

TABLE A-continued

| row | B | D |
|---|---|---|
| A-717 | 2-(difluoromethoxy)-6-chlorophenyl | MgI |
| A-718 | 3-(difluoromethoxy)-4-chlorophenyl | MgI |
| A-719 | 3-(difluoromethoxy)-5-chlorophenyl | MgI |
| A-720 | 2-chloro-3-(difluoromethoxy)phenyl | MgI |
| A-721 | 2-chloro-4-(difluoromethoxy)phenyl | MgI |
| A-722 | 2-chloro-5-(difluoromethoxy)phenyl | MgI |
| A-723 | 3-chloro-4-(difluoromethoxy)phenyl | MgI |
| A-724 | 2-(difluoromethoxy)-3-fluorophenyl | MgI |
| A-725 | 2-(difluoromethoxy)-4-fluorophenyl | MgI |
| A-726 | 2-(difluoromethoxy)-5-fluorophenyl | MgI |
| A-727 | 2-(difluoromethoxy)-6-fluorophenyl | MgI |
| A-728 | 3-(difluoromethoxy)-4-fluorophenyl | MgI |
| A-729 | 3-(difluoromethoxy)-5-fluorophenyl | MgI |
| A-730 | 2-fluoro-3-(difluoromethoxy)phenyl | MgI |
| A-731 | 2-fluoro-4-(difluoromethoxy)phenyl | MgI |
| A-732 | 2-fluoro-5-(difluoromethoxy)phenyl | MgI |
| A-733 | 3-fluoro-4-(difluoromethoxy)phenyl | MgI |
| A-734 | 2,3,4-trichlorophenyl | MgI |
| A-735 | 2,3,5-trichlorophenyl | MgI |
| A-736 | 2,3,6-trichlorophenyl | MgI |
| A-737 | 2,4,5-trichlorophenyl | MgI |
| A-738 | 2,4,6-trichlorophenyl | MgI |
| A-739 | 3,4,5-trichlorophenyl | MgI |
| A-740 | 2,3,4-trifluorophenyl | MgI |
| A-741 | 2,3,5-trifluorophenyl | MgI |
| A-742 | 2,3,6-trifluorophenyl | MgI |
| A-743 | 2,4,5-trifluorophenyl | MgI |
| A-744 | 2,4,6-trifluorophenyl | MgI |
| A-745 | 3,4,5-trifluorophenyl | MgI |

According to another aspect of the present invention, thiotriazolo-group containing compounds (I), particularly pesticidal compounds of the triazole class having phytopathogenic activity of formula (I)

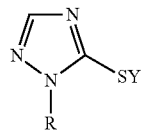
(I)

are synthesized from a compound of formula (IIa)

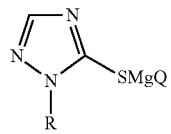
(IIa)

by means of the inventive process comprising the step (iii-1) or (iii-2) as defined above.

According to another aspect of the present invention, compounds of formula (IIa) can be obtained by a process comprising the step of reacting a compound (IIIa) with sulfur according to step (ii) as defined above.

According to one embodiment of the inventive process, step (i), then step (ii) and then step (iii-1) or (iii-2) are carried out. Thus, according to this embodiment, the inventive process comprises the steps (i), (ii) and, subsequently, (iii-1) or (iii-2).

According to another embodiment of the inventive process, step (iv) is carried out in order to synthesize compounds of formula (I) starting from compounds (IIIa). Thus, according to this embodiment, the inventive process comprises step (iv).

According to still another embodiment of the inventive process, step (i), then step (iv) is carried out. Thus, according to this embodiment, the inventive process comprises the steps (i) and (iv).

A further advantage of the inventive process is that thiotriazolo compounds (I) are accessible in a one-pot reaction. Furthermore, if desired, the reaction can be carried out without cooling or at slightly elevated temperatures and with the conversion to the desired products being high. Thereby, only few or virtually no significant amounts of side-products are formed. The process is thus very economic.

The novel compounds according to the invention contain chiral centers and are generally obtained in the form of racemates or as diastereomeric mixtures of erythro and threo forms. The erythro and threo diastereomers of the compounds according to the invention can be separated and isolated in pure form, for example, on the basis of their different solubilities or by column chromatography. Using known methods, such uniform pairs of diastereomers can be used to obtain uniform enantiomers.

Accordingly, the invention provides both the pure enantiomers or diastereomers and mixtures thereof. This applies to the compounds according to the invention. The scope of the present invention includes in particular the (R) and (S) isomers and the racemates of the compounds according to the invention, which have centers of chirality. Suitable compounds according to the invention also include all possible stereoisomers (cis/trans isomers) and mixtures thereof.

The compounds according to the invention may be present in various crystal modifications. They are likewise provided by the present invention.

Furthermore, in the inventive process, the reactants used, contain chiral centers and are generally used in the form of racemates or as diastereomeric mixtures of erythro and threo forms. The erythro and threo diastereomers of these compounds can be separated and isolated in pure form, for example, on the basis of their different solubilities or by column chromatography. Using known methods, such uniform pairs of diastereomers can be used to obtain uniform enantiomers.

Accordingly, the invention provides both the use of pure enantiomers or diastereomers and mixtures thereof. The scope of the present invention includes in particular the use of the (R) and (S) isomers and the racemates of the respective reactants, which have centers of chirality. Suitable compounds used according to the invention also include all possible stereoisomers (cis/trans isomers) and mixtures thereof.

The compounds used according to the invention may be present in various crystal modifications. They are likewise possible to be used in the inventive process.

In order to obtain compounds of formula (I) that contain a derivatized sulfur group (Y other that hydrogen), the compounds of formula (I), wherein Y=hydrogen (compounds (I.1)) can be further reacted according to processes known in the art.

For example, by further reaction of compounds (1.1) with $R^{8A}$-LG, where $R^8A$ is as defined below and LG is a leaving group such as, for example, halogen, such as Cl, Br or I, or perfluoroalkylsulfonate, e.g. trifluoromethylsulfonate or nonafluorobutanesulfonate, it is possible to prepare various compounds of the formula (I) carrying a S—$R^8A$ group instead of "S—H". To prepare compounds containing a group $SR^{8A}$ where $R^{8A}$ is $C_1$-$C_8$-alkyl, preferably $C_1$-$C_5$-alkyl or $C_1$-$C_4$-alkyl, in particular $C_3$-alkyl or $C_5$-alkyl, specifically methyl, ethyl, iso-propyl, n-butyl or n-pentyl, a compound (I.1) is reacted with the corresponding alkyl halide (see also WO 96/38440).

Further, the following S-residues can be formed from the respective SH-derivative of formula (I):

S—$R^{8A}$, where $R^{8A}$ is $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, C(=O)$R^{5A}$, C(=S)$R^{5A}$, $SO_2R^{6A}$ or CN; where $R^{5A}$ is $C_1$-$C_8$-alkyl, $C_1$-$C_8$-haloalkyl, $C_1$-$C_8$-alkoxy, $C_1$-$C_8$-haloalkoxy or $NA^{3A}A^{4A}$; and $R^{6A}$ is $C_1$-$C_8$-alkyl, phenyl-$C_1$-$C_8$-alkyl or phenyl, where the phenyl groups are in each case unsubstituted or substituted by one, two or three groups independently selected from the group consisting of halogen and $C_1$-$C_4$-alkyl;

$A^{3A}$,$A^{4A}$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl S-DII, wherein DII is

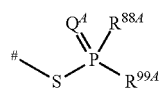

DII where # is the point of attachment to the triazolyl ring and $Q^A$, $R^{88A}$ and $R^{99A}$ are as defined below:

$Q^A$ is O or S;

$R^{88A}$, $R^{99A}$ independently of one another are $C_1$-$C_8$-alkyl, $C_1$-$C_8$-haloalkyl, $C_1$-$C_8$-alkoxy, $C_1$-$C_8$-alkoxy-$C_1$-$C_8$-alkoxy, $C_1$-$C_8$-haloalkoxy, $C_1$-$C_8$-alkoxy-$C_1$-$C_8$-alkyl, $C_1$-$C_8$-alkylthio, $C_2$-$C_8$-alkenylthio, $C_2$-$C_8$-alkynylthio, $C_3$-$C_8$-cycloalkyl, $C_3$-$C_8$-cycloalkylthio, phenyl, phenyl-$C_1$-$C_4$-alkyl, phenoxy, phenylthio, phenyl-$C_1$-$C_4$-alkoxy or $NR^{111A}R^{222A}$, where $R^{111A}$ is H or $C_1$-$C_8$-alkyl and $R^{222A}$ is $C_1$-$C_8$-alkyl, phenyl-$C_1$-$C_4$-alkyl or phenyl or $R^{111A}$ and $R^{222A}$ together are an alkylene chain having four or five carbon atoms or form a radical of the formula-$CH_2$—$CH_2$—O—$CH_2$—$CH_2$— or —$CH_2$—$CH_2$—$NR^{333A}$—$CH_2$—$CH_2$— in which $R^{333A}$ is hydrogen or $C_1$-$C_4$-alkyl; where the aromatic groups in the radicals mentioned above are in each case independently of one another unsubstituted or substituted by one, two or three groups selected from the group consisting of halogen and $C_1$-$C_4$-alkyl;

$SM^{1A}$, wherein $M^{1A}$ is an alkali metal cation, an equivalent of an alkaline earth metal cation, an equivalent of a copper, zinc, iron or nickel cation or an ammonium cation of the formula (E)

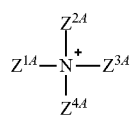

(E)

in which $Z^{1A}$ and $Z^{2A}$ independently are hydrogen or $C_1$-$C_8$-alkyl;

$Z^{3A}$ and $Z^{4A}$ independently are hydrogen, $C_1$-$C_8$-alkyl, benzyl or phenyl; where the phenyl groups are in each case unsubstituted or substituted by one, two or three groups independently selected from the group consisting of halogen and $C_1$-$C_4$-alkyl.

According to an embodiment of the invention Y in compounds (I) is derivatized into Na, ½Cu or an ammonium cation of the formula (E), wherein $Z^{1A}$ and $Z^{2A}$ preferably are independently selected from hydrogen and $C_1$-$C_4$-alkyl and $Z^{3A}$ and $Z^{4A}$ are preferably independently selected from hydrogen, $C_1$-$C_4$-alkyl, benzyl and phenyl; where the phenyl groups are in each case unsubstituted or substituted by one, two or three groups independently selected from the group consisting of halogen and $C_1$-$C_4$-alkyl. It may be preferred, if in group (E), $Z^{1A}$, $Z^{2A}$, $Z^{3A}$ and $Z^{4A}$ are independently selected from hydrogen and $C_1$-$C_4$-alkyl, in particular hydrogen, methyl and ethyl. One particular suitable group (E) is $HN(Et)_3$.

Compounds of the formula I which contain a group S—C(=O)$NA^{3A}A^{4A}$ can be synthesized analogously to the process described in WO 99/21853.

Compounds of the formula I which contain a group DII can be synthesized analogously to the process described in WO 99/05149.

Compounds of the formula I which contain a group S—$SO_2R^{10A}$ can be synthesized analogously to the process described in WO 97/44332.

Compounds of the formula I which contain a group S—CN can be synthesized analogously to the process described in WO 99/44331.

Compounds of the formula I which contain a group DI can be synthesized analogously to the process described in WO 97/43269.

Compounds of the formula I which contain a group S—C(=O)$R^{5A}$ where $R^{5A}$=$C_1$-$C_8$-alkyl, $C_1$-$C_8$-haloalkyl, $C_1$-$C_8$-alkoxy or $C_1$-$C_8$-haloalkoxy can be synthesized analogously to the process described in WO 97/42178.

Compounds of the formula I which contain a group $SM^{1A}$ can be synthesized analogously to the process described in WO 97/41107.

According to one aspect of the present invention, one of the steps for derivatizing the sulfur in the triazole ring as detailed above is carried out following the process of the present invention, wherein Y=H. According to one specific aspect, following the synthesis of compounds (I)-(1) with Y=H according to the process of the present invention, one of the steps for derivatizing the sulfur in the triazole ring is carried out. This represents a very useful approach for the synthesis of further fungicidal compounds, in particular where SH is derivatized into $SR^{8A}$, $R^{8A}$ being $C_1$-$C_8$-alkyl, in particular $C_1$-$C_5$-alkyl, $C_2$-$C_8$-alkenyl or CN (see specific examples above). According to one further specific aspect, following the synthesis of compounds (I)-(1) with Y=H according to the process of the present invention, the step of derivatizing the sulfur in the triazole ring is derivatized into $SM^{1A}$, wherein $M^{1A}$ is as defined and preferably defined above. See WO 97/41107.

EXAMPLES

The following examples further illustrate the present invention and do not restrict the invention in any manner.

Example 1

Synthesis of (2RS,3SR)-2-[3-(2-chloro-phenyl)-2-(2,4-difluoro-phenyl)oxiranylmethyl]-2,4-dihydro-[1,2,4]triazole-3-thione A solution of (2RS,3SR)-2-[3-(2-chloro-phenyl)-2-(2,4-difluoro-phenyl)-oxiranylmethyl]-[1,2,4]triazole (150 g, 431 mmol) in 1.25 L of THF was cooled to 0° C. A solution of iPrMgCl in THF (2.0 M in THF, 260 mL, 520 mmol) was added at a rate to keep the temperature below 5° C. The solution was then allowed to warm to 22° C. and stirred for an additional 60 min at that temperature. The solution was then cooled to 0° C. and sulfur (26.9 g, 839 mmol) was added portionwise at a rate to keep the temperature below 7° C. Stirring was continued for another 60 min at 0° C. Then, 4% HCl (1.1 kg) was added, followed by 550 mL of toluene. The phases were separated and the aqueous phase was extracted with toluene (2×275 mL). The combined organic phases were washed with water (275 mL). All volatiles were removed under reduced pressure and the residue was recrystallized from o-xylene (1.3 kg). The crystals were filtered off, rinsed with o-xylene and petrol ether and dried at a pressure of 20 mbar and a temperature of 60° C. overnight to give the product as a colorless solid (123 g, purity 95.5% by HPLC, 74% yield).

$^1$H NMR (CDCl$_3$, 500 MHz): δ (ppm)=13.31 (bs, 1H); 8.24 (s, 1H); 7.55-7.61 (m, 2H); 7.45-7.50 (m, 2H); 7.34 (q, J=9.5 Hz, 1H); 7.27 (dt, J=3.0 Hz, J=12.5 Hz, 1H); 7.05 (ddd, J=3.0 Hz, J=9.5 Hz, J=10.5 Hz, 1H); 4.46 (d, J=18.0 Hz, 1H); 4.39 (s, 1H); 4.12 (d, J=18.0 Hz, 1H).

Melting point: 180° C.

Example 2

Synthesis of (2RS,3SR)-2-[3-(2-chloro-phenyl)-2-(2-fluoro-phenyl)oxiranylmethyl]-2,4-dihydro-[1,2,4]triazole-3-thione A solution of (2RS,3SR)-2-[3-(2-chloro-phenyl)-2-(2-fluoro-phenyl)-oxiranylmethyl]-[1,2,4]triazole (3.0 g, 9.10 mmol) in 22 mL of THF was cooled to 0° C. A solution of iPrMgCl in THF (2.0 M in THF, 4.5 mL, 9.0 mmol) was added at a rate to keep the temperature below 5° C. The solution was then allowed to warm to 22° C. and stirred for an additional 60 min at that temperature. The solution was then cooled to 0° C. and a suspension of sulfur (0.57 g, 17.8 mmol) in 5 mL of THF was added portionwise at a rate to keep the temperature below 7° C. Stirring was continued for another 60 min at 0° C. Then, the solution was poured on 4% HCL (50 mL) and extracted with TBME (30 mL). The aqueous phase was extracted with TBME (30 mL). The combined organic phases were washed with water and brine and dried over Na$_2$SO$_4$. The crude product obtained after evaporation of all volatiles was purified by recrystallisation from xylenes (70 mL) to give the product as a colorless solid (2.3 g, 6.36 mmol, 70% yield).

$^1$H NMR (DMSO-d$_6$, 500 MHz): δ (ppm)=13.35 (s, 1H); 820 (s, 1H); 7.43-7.60 (m, 6H); 7.18 (t, J=9.5 Hz, 2H); 4.89 (d, J=15 Hz, 1H); 4.20 (s, 1H); 3.73 (d, J=15.0 Hz, 1H).

Melting point: 179° C.

Example 3

Synthesis of (2RS,3SR)-1-[3-(2-chloro-phenyl)-2-(2,4-difluoro-phenyl)oxiranylmethyl-5-allylsulfanyl-1H-[1,2,4]triazole A solution of (2RS,3SR)-2-[3-(2-chloro-phenyl)-2-(2,4-difluoro-phenyl)-oxiranylmethyl]-[1,2,4]triazole (5.0 g, 14.4 mmol) in 40 mL of THF was slowly treated with a solution of iPrMgCl in THF (2.0 M in THF, 8.6 mL, 17.0 mmol) at a rate to keep the temperature below 40° C. The solution was then stirred at 40° C. for 60 min and afterwards cooled to 0° C. Sulfur (0.90 g, 28.1 mmol) was then added portionwise a rate to keep the temperature below 7° C. Stirring was continued for another 60 min at 0° C. Then, allyl bromide (2.5 mL, 28.9 mmol) was added in one portion and the solution was slowly warmed to ambient temperature and stirred at that temperature overnight. To this solution was then added 50 mL of water and 50 mL of TBME. The organic phase was washed with water and brine and dried over Na$_2$SO$_4$. The crude product was obtained after removal of all volatiles under reduced pressure. Purification was accomplished through flash column chromatography on silica (cyclohexane/EtOAc mixtures) to obtain the product as a tan solid (4.4 g, 10.5 mmol, 73% yield).

$^1$H NMR (CDCl$_3$, 500 MHz): δ (ppm)=8.02 (s, 1H); 7.76 (dd, J=3.0 Hz, J=8.5 Hz, 1H); 7.73 (dd, J=3.5 Hz, 8.5 Hz, 1H); 7.61-7.66 (m, 2H); 7.42 (dt, J=3.0 Hz, J=12.5 Hz, 1H); 7.40 (dt, J=8.5 Hz, J=10.5 Hz, 1H); 7.21 (dt, J=2.5 Hz, J=10.5 Hz, 1H); 5.86 (tdd, J=9.0 Hz, J=12.5 Hz, J=21.0 Hz, 1H); 5.25 (dd, J=2.0 Hz, J=21.0 Hz, 1H); 5.14 (dd, J=2.0 Hz, J=12.5 Hz, 1H); 4.63 (d, J=18.5 Hz, 1H); 4.58 (s, 1H); 4.17 (d, J=18.5 Hz, 1H); 3.81 (d, J=9.0 Hz; 2H).

Melting point: 67° C.

Example 4

Synthesis of (2RS,3SR)-1-[3-(2-chloro-phenyl)-2-(2,4-difluoro-phenyl)oxiranylmethyl-5-methylsulfanyl-1H-[1,2,4]triazole A solution of (2RS,3SR)-2-[3-(2-chloro-phenyl)-2-(2,4-difluoro-phenyl)-oxiranylmethyl]-[1,2,4]triazole (2.1 g, 6.04 mmol) in 15 mL of THF was slowly treated with a solution of iPrMgCl in THF (2.0 M in THF, 3.6 mL, 7.2 mmol) at a rate to keep the temperature below 40° C. The solution was then stirred at 40° C. for 60 min and afterwards cooled to 0° C. A solution of S-methyl methanethiosulfonate (1.0 g, 7.9 mmol) in 2 mL, of THF was added at once. The solution was slowly warmed to room temperature and stirred overnight (16 h). The solution was than poured on 4% HCl (30 mL) and extracted with TBME. The aqueous phase was extracted with TBME (30 mL). The combined organic layers were washed with water and brine and dried over Na$_2$SO$_4$. The crude product was obtained after removal of all volatiles. Purification of the crude product was accomplished through flash column chromatography on silica (cyclohexane/EtOAc mixtures) to obtain the product as a colorless solid (1.75 g, 4.44 mmol, 74% yield).

$^1$H NMR (DMSO-d$_6$, 500 MHz): δ (ppm)=7.82 (s, 1H); 7.46-7.62 (m, 4H); 7.33 (dt, J=2.0 Hz, J=10.0 Hz, 1H); 7.21-7.27 (m, 1H); 7.06 (dt, J=2.0 Hz, J=8.5 Hz, 1H); 4.47 (d, J=15.0 Hz, 1H); 4.43 (s, 1H); 3.96 (d, J=15.0 Hz, 1H); 2.45 (s, 3H).

Melting point: 125° C.

Example 5

Synthesis of (2RS,3SR)-1-[3-(2-chloro-phenyl)-2-(2,4-difluoro-phenyl)oxiranylmethyl-5-phenylsulfanyl-1H-[1,2,4]triazole A solution of (2RS,3SR)-2-[3-(2-chloro-phenyl)-2-(2,4-difluoro-phenyl)-oxiranylmethyl]-[1,2,4]triazole (3.0 g, 8.63 mmol) in 20 mL of THF was slowly treated with a solution of iPrMgCl in THF (2.0 M in THF, 5.1 mL, 10.2 mmol) at a rate to keep the temperature below 40° C. The solution was then stirred at 40° C. for 60 min and afterwards cooled to 0° C. A solution of diphenyl disulfide (3.7 g, 16.9 mmol) in 5 mL of THF was slowly added. The solution was kept at that temperature for another 60 min and then poured on ice-cold 4% HCl (50 mL). The aqueous phase was extracted with TBME (2×25 mL). The combined organic layers were washed with water and brine and dried over $Na_2SO_4$. The crude product was obtained after removal of all volatiles under reduced pressure. Purification was then accomplished through flash column chromatography on silica (cyclohexane/EtOAc mixtures) to obtain the product as a colorless liquid that solidified upon standing (3.3 g, 7.24 mmol, 84% yield).

$^1$H NMR (DMSO-$d_6$, 500 MHz): δ (ppm)=7.80 (s, 1H); 7.46-7.63 (m, 4H); 7.15-7.34 (m, 7H); 7.04 (dt, J=2.0 Hz, J=10.5 Hz, 1H); 4.63 (d, J=19.0 Hz, 1H); 4.46 (s, 1H); 4.19 (d, J=19.0 Hz, 1H).

Melting point: 78° C.

Example 6

Synthesis of 2-[5-(4-chloro-benzylidene)-1-hydroxy-2,2-dimethyl-cyclopentylmethyl]-2,4-dihydro-[1,2,4]triazole-3-thione To an ice-cold solution of 5-(4-chloro-benzylidene)-2,2-dimethyl-1-[1,2,4]triazol-1-ylmethyl-cyclopentanol (3.00 g, 9.44 mmol) in 25 mL of THF was added a solution iPrMgCl in THF (2.0 M, 12.0 mL, 24.0 mmol). Upon the addition of the base, a colorless precipitate formed. The suspension was warmed to 40° C. and kept at that temperature for 90 min. Then, the clear solution was cooled to 0° C. and portionwise treated with sulfur (1.0 g, 31.2 mmol) and stirred for another 60 min at that temperature. The solution was then poured onto 4% HCl (100 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless solid (2.80 g, 8.00 mmol, 85% yield).

$^1$H NMR (DMSO-$d_6$, 500 MHz): δ (ppm)=13.35 (s, 1H); 8.29 (s, 1H); 7.34 (d, J=10.5 Hz, 2H); 7.19 (d, J=10.5 Hz, 2H); 5.81 (s, 1H); 4.89 (s, 1H); 4.56 (d, J=17.5 Hz, 1H); 3.99 (d, J=17.5 Hz, 1H); 2.84-2.94 (m, 1H); 2.34-2.46 (m, 1H); 1.80-1.90 (m, 1H); 1.55-1.64 (m, 1H); 1.08 (s, 3H); 0.78 (s, 3H).

Melting point: 177° C.

Example 7

Synthesis of (cis/trans)-2-[5-(4-chloro-benzyl)-1-hydroxy-2,2-dimethyl-cyclopentylmethyl]-2,4-dihydro-[1,2,4]triazole-3-thione To an ice-cold solution of 5-(4-chloro-benzyl)-2,2-dimethyl-1-[1,2,4]triazol-1-ylmethyl-cyclopentanol (3.00 g, 9.38 mmol) in 25 mL of THF was added a solution iPrMgCl in THF (2.0 M, 12.0 mL, 24.0 mmol). The solution was warmed to 40° C. and kept at that temperature for 90 min. Then, it was cooled to 0° C. and portionwise treated with sulfur (1.0 g, 31.2 mmol) and stirred for another 60 min at that temperature. The solution was then poured onto 4% HCl (100 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless solid (2.60 g, 7.39 mmol, 79% yield).

Major Diastereoisomer $^1$H NMR (DMSO-$d_6$, 500 MHz): δ (ppm)=13.70 (s, 1H); 8.48 (s, 1H); 7.18-7.32 (m, 4H); 4.50 (d, J=20.0 Hz, 1H); 4.37 (s, 1H); 4.17 (d, J=20.0 Hz, 1H); 2.52-2.62 (m, 1H); 2.31-2.48 (m, 2H); 1.63-1.73 (m, 1H); 1.38-1.52 (m, 1H); 1.13-1.29 (m, 2H); 0.97 (s, 3H); 0.91 (s, 3H), Melting point: 194° C.

Example 8

Synthesis of 2-{2-[2-(4-chloro-phenyl)-ethyl]-2-hydroxy-3,3-dimethyl-butyl}-2,4-dihydro-[1,2,4]triazole-3-thione To an ice-cold solution of 1-(4-chloro-phenyl)-4,4-dimethyl-3-[1,2,4]triazol-1-ylmethyl-pentan-3-ol (236 mg, 0.77 mmol) in 2 mL of THF was added a solution iPrMgCl in THF (2.0 M, 1.0 mL, 2.0 mmol). The solution was warmed to 40° C. and kept at that temperature for 90 min. Then, it was cooled to 0° C. and treated and a suspension of sulfur (75 g, 2.34 mmol) in 1 mL of THF was added portionwise and the mixture stirred for another 60 min at 0° C. The solution was then poured onto 4% HCl (20 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid (151 mg, 0.44 mmol, 58% yield).

$^1$H NMR (DMSO-$d_6$, 500 MHz): δ (ppm)=8.40 (s, 1H); 7.29 (d, J=12.0 Hz, 2H); 7.18 (d, J=12.0 Hz, 2H); 4.51-4.58 (m, 2H); 4.00-4.06 (m, 1H); 2.61 (dt, J=5.0 Hz, J=17.0 Hz, 1H); 2.20-2.30 (m, 1H); 1.94-2.04 (m, 1H); 1.70 (dt, J=5.0 Hz, J=19.0 Hz, 1H); 0.94 (s, 9H).

Example 9

Synthesis of [2-2-(1-chloro-cyclopropyl)-3-(2-chloro-phenyl)-2-hydroxypropyl]-2,4-dihydro-[1,2,4]triazole-3-thione To a solution of 2-(1-chloro-cylopropyl)-1-(2-chloro-phenyl)-3-[1,2,4]triazol-1-yl-propan-2-ol (252 mg, 0.81 mmol) in 2 mL of THF was added a solution iPrMgCl in THF (2.0 M, 1.0 mL, 2.0 mmol). The suspension was warmed to 40° C. and kept at that temperature for 90 min. Then, the clear solution was cooled to 0° C. and portionwise treated with sulfur (75 mg, 2.34 mmol) and stirred for another 60 min at that temperature. To the solution was then added 4% HCl (20 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a odorless solid (189 mg, 0.55 mmol, 68% yield).

$^1$H NMR (CDCl$_3$, 500 MHz): δ (ppm)=12.49 (bs, 1H); 7.86 (s, 1H); 7.52-7.56 (m, 1H); 7.34-7.39 (m, 1H); 7.16-7.25 (m, 2H); 4.79 (d, J=18.5 Hz, 1H); 4.49 (d, J=18.5 Hz, 1H); 4.23 (s, 1H); 3.61 (d, J=17.5 Hz, 1H); 3.18 (d, J=17.5 Hz, 1H); 0.90-0.96 (m, 1H); 0.74-0.88 (m, 3H).

Melting point: 137° C.

Example 10

Synthesis of 2-[2-(4-chloro-phenyl)-3-cyclopropy-2-hydroxy-butyl]-2,4-dihydro-[1,2,4]triazole-3-thione To an ice-cold solution of 2-(4-chloro-phenyl)-3-cyclopropyl-1-[1,2,4]triazol-1-yl-butan-2-ol (340 mg, 1.17 mmol) in 2.5 mL of THF was added a solution iPrMgCl in THF (2.0 M, 1.5 mL, 3.0 mmol). The solution was warmed to 40° C. and kept at that temperature for 90 min. Then, the clear solution was cooled to 0° C. and portionwise treated with sulfur (107 mg, 3.34 mmol) and stirred for another 60 min at that temperature. The solution was then poured onto 4% HCl (20 mL). The aqueous phase was extracted with TBME (2×20 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid that solidified upon standing (225 mg, 0.69 mmol, 60% yield of a 60:40 mixture of diastereoisomers).

Major Diastereoisomer $^1$H NMR (CDCl$_3$, 500 MHz): δ (ppm)=10.90 (bs, 1H); 7.62 (s, 1H); 7.44 (d, J=8.5 Hz, 2H); 7.21 (d, J=8.5 Hz, 2H); 5.36 (d, J=14.5 Hz, 1H); 4.82 (d, J=14.5 Hz, 1H); 1.14 (q, J=7.0 Hz, 1H); 1.01 (d, J=7.0 Hz, 3H); 0.03-0.70 (m, 5H).

Minor Diastereoisomer $^1$H NMR (CDCl$_3$, 500 MHz): δ (ppm)=10.90 (bs, 1H); 7.60 (s, 1H); 7.32 (d, J=8.5 Hz, 2H); 7.17 (d, J=8.5 Hz, 2H); 4.92 (d, J=14.5 Hz, 1H); 4.29 (d, J=14.5 Hz, 1H); 1.24 (q, J=7.0 Hz, 1H); 0.81 (d, J=7.0 Hz, 3H); 0.03-0.70 (m, 5H).

Melting point: 137° C.

Example 11

Synthesis of 2-{1-[3-(2,4-dichloro-phenyl)-2-methyl-propyl]-2-hydroxy-3,3-dimethyl-butyl}-2,4-dihydro-[1,2,4]triazole-3-thione To a solution of 7-(2,4-dichloro-phenyl)-2,2,6-trimethyl-4-[1,2,4]triazol-1-yl-heptan-3-ol (3.00 g, 8.93 mmol) in 14 mL of THF was added a solution iPrMgCl in THF (2.0 M, 11.0 mL, 22.0 mmol). The solution was warmed to 40° C. and kept at that temperature for 120 min. Then, the clear solution was cooled to 0° C. and portionwise treated with sulfur (0.85 g, 26.6 mmol) and stirred for another 60 min at that temperature. To the solution was added 4% HCl, followed by TBME (both 50 mL). The aqueous phase was extracted with TBME (25 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid that solidified upon standing (2.2 g, 5.98 mmol, 67% yield of a 1:1 mixture)

Diastereoisomer I $^1$H NMR (CDCl$_3$, 500 MHz): δ (ppm)=12.81 (s, 1H); 7.38 (s, 1H); 6.62 (d, J=2.5 Hz); 6.48 (dd, J=2.5 Hz, J=8.0 Hz, 1H); 6.41 (d, J=8.0 Hz, 1H); 4.48 (d, J=9.0 Hz, 1H); 3.27 (d, J=9.0 Hz, 1H); 2.65 (d. J=9.0 Hz, 1H); 1.98 (dd, J=6.5 Hz, J=8.5 Hz, 1H); 1.75 (dd, J=8.0 Hz, J=8.5 Hz, 1H); 1.46-1.52 (m, 1H); 0.78-0.91 (m, 2H); 0.29 (d, J=6.5 Hz, 3H); 0.11 (s, 9H).

Diastereoisomer II $^1$H NMR (CDCl$_3$, 500 MHz): δ (ppm)=8.21 (s, 1H); 7.36 (d, J=2.0 Hz, 1H); 7.32-7.35 (m, 1H); 7.19 (dd, J=2.0 Hz, J=8.0 Hz); 5.20-5.26 (m, 1H); 4.05 (d, J=8.0 Hz, 1H); 3.36 (d, J=8.5 Hz, 1H); 3.01 (dd, J=4.0 Hz, J=13.0 Hz, 1H); 2.51-2.57 (m, 1H); 1.93-2.00 (m, 1H); 1.82-1.88 (m, 1H); 1.62-1.68 (m, 1H); 0.82 (s, 9H); 0.78 (d, J=6.5 Hz, 3H).

Melting point: 164° C.

Example 12

Synthesis of 2-{2-[2-chloro-4-(4-chloro-phenoxy)-phenyl]-4-methyl-[1,3]dioxolan-2-ylmethyl}-2,4-dihydro-[1,2,4]triazole-3-thione To a solution of 1-{2-[2-chloro-4-(4-chloro-phenoxy)-phenyl]-4-methyl-[1,3]dioxolan-2-ylmethyl}1H-[1,2,4]triazole (524 mg, 1.28 mmol) in 1.3 mL of THF was added a solution iPrMgCl in THF (2.0 M, 1.0 mL, 2.0 mmol). The solution was warmed to 40° C. and kept at that temperature for 90 min. Then, the clear solution was cooled to 0° C. and portionwise treated with sulfur (82 mg, 2.55 mmol) and stirred for another 60 min at that temperature. To the solution was added 4% HCl, followed by TBME (both 5 mL). The aqueous phase was extracted with TBME (5 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid that solidified upon standing (333 mg, 0.76 mmol, 59% yield of a 1:1 mixture of diastereoisomers)

Mixture of Diastereoisomers $^1$H NMR (CDCl$_3$, 500 MHz): δ (ppm)=13.18 (s, 1H); 7.72 (s, 0.5H); 7.68 (s, 0.5H); 7.63 (d, J=3.0 Hz, 0.5H); 7.61 (d, J=3.0 Hz, 0.5H); 7.33 (d, J=8.5 Hz, 2H); 6.97-7.01 (m, 2H); 6.79-6.83 (m, 1H); 4.85 (d, J=14.0 Hz, 0.5H); 4.84 (d, J=14.0 Hz, 0.5H); 4.77 (d, J=14.0 Hz, 0.5H); 4.69 (d, J=14.0 Hz, 0.5H); 4.32-4.38 (m, 0.5H); 4.22 (dd. J=6.0 Hz, J=8.0 Hz, 0.5H); 4.11-4.16 (m, 0.5H); 3.98 (dd, J=6.5 Hz, J=7.5 Hz, 0.5H); 3.49 (t, J=7.5 Hz, 0.5H); 3.40 (t, J=8.0 Hz, 0.5H); 2.74 (bs, 1H); 1.21-1.27 (m, 3H).

Melting point: 130° C.

Example 13

Synthesis of 2-[2-(2,4-dichloro-phenyl)-4-propyl-[1,3]dioxolan-2-ylmethyl]-2,4-dihydro-[1,2,4]triazole-3-thione To a solution of 1-[2-(2,4-dichloro-phenyl)-4-propyl-[1,3]dioxolan-1-ylmethyl]-1H-[1,2,4]triazole (511 mg, 1.49 mmol) in 1.5 mL of THF was added a solution iPrMgCl in THF (2.0 M, 1.1 mL, 2.2 mmol). The solution was warmed to 40° C. and kept at that temperature for 90 min. Then, the clear solution was cooled to 0° C. and portionwise treated with sulfur (96 mg, 2.99 mmol) and stirred for another 60 min at that temperature. To the solution was added 4% HCl, followed by TBME (both 5 mL). The aqueous phase was extracted with TBME (5 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid that solidified upon standing (198 mg, 0.53 mmol, 35% yield of a 1:1 mixture of diastereoisomers)

Mixture of Diastereoisomers $^1$H NMR (CDCl$_3$, 500 MHz): δ (ppm)=13.15 (s, 1H); 7.91 (s, 0.5H); 7.86 (s, 0.5H); 7.59 (d, J=8.5 Hz, 0.5 Hz); 7.58 (d, J=8.5 Hz, 0.5 Hz); 7.42 (d, J=2.0 Hz, 1H); 7.17-7.24 (m, 1H); 4.86 (d, J=14.0 Hz, 0.5H); 4.85 (d, J=14.5 Hz, 0.5H); 4.77 (d, J=14.0 Hz, 0.5H); 4.70 (d, J=14.5 Hz, 0.5H); 4.19-4.25 (m, 1H); 3.90-4.00 (m, 1H); 3.55 (t, J=7.0 Hz, 0.5H); 3.42-3.47 (m, 0.5H); 1.52-1.63 (m, 1H); 1.24-1.46 (m, 3H); 0.90 (t, J=7.5 Hz, 1.5H); 0.89 (t, J=7.5 Hz, 1H).

Melting point: 128° C.

Example 14

Synthesis of 2-[2-(2,4-dichloro-phenyl)-2-hydroxy-pentyl]-2,4-dihydro-[1,2,4]triazole-3-thione To an ice-cold solution of 2-(2,4-dichloro-phenyl)-1-[1,2,4]triazol-1-yl-pentan-2-ol (330 mg, 1.05 mmol) in 2.5 mL of THF was added a solution iPrMgCl in THF (2.0 M, 1.3 mL, 2.6 mmol). The solution was warmed to 40° C. and kept at that temperature for 90 min. Then, it was cooled to 0° C. and treated and a suspension of sulfur (107 mg, 3.18 mmol) in 1 mL of THF was added portionwise and the mixture stirred for another 60 min at 0° C. The solution was then poured onto 4% HCl (20 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a odorless liquid (290 mg, 0.84 mmol, 80% yield) that solidified upon standing.

$^1$H NMR (CDCl$_3$, 500 MHz): δ (ppm)=12.40 (bs, 1H); 7.74 (d, J=10.5 Hz, 1H); 7.72 (s, 1H); 7.37 (d, J=3.0 Hz, 1H); 7.20 (dd. J=3.0 Hz, J=10.5 Hz, 1H); 4.94 (d, 18.0 Hz, 1H); 4.83 (d, J=18.0 Hz, 1H); 2.57 (dt, J=3.0 Hz, J=15.5 Hz, 1H); 1.72-1.81 (m, 1H); 1.20-1.32 (m, 2H); 0.84-0.90 (m, 2H); 0.83 (t, J=9.0 Hz, 3H).

Melting point: 148° C.

Example 15

Synthesis of 2-[2-(4-fluoro-phenyl)-2-hydroxy-3-trimethylsilanylpropyl]-2,4-dihydro-[1,2,4]triazole-3-thione To a solution of 2-(4-fluoro-phenyl)-1-[1,2,4]-1-yl-3-trimethyl-silanyl-propan-2-ol (226 mg, 0.77 mmol) in 3 mL of THF was added a solution iPrMgCl in THF (2.0 M, 1.2 mL, 2.4 mmol). The solution was warmed to 40° C. and kept at that temperature for 90 min. Then, it was cooled to 0° C. and treated and a suspension of sulfur (85 mg, 2.65 mmol) in 1 mL of THF was added portionwise and the mixture stirred for another 60 min at 0° C. The solution was then poured onto 4% HCl (20 mL). The aqueous phase was extracted with TBME (2×20 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid (182 mg, 0.56 mmol, 73% yield) that solidified upon standing.

$^1$H NMR (CDCl$_3$, 500 MHz): δ (ppm)=12.86 (bs, 1H); 7.91 (s, 1H); 7.60-7.64 (m, 2H); 7.16 (t, J=9.0 Hz, 2H); 4.79 (d, J=14.5 Hz, 1H); 4.58 (d, J=14.5 Hz, 1H); 4.49 (bs, 1H); 1.54 (d, J=14.5 Hz, 1H); 1.45 (d, J=14.5 Hz, 1H); 0.00 (s, 9H).

Melting point: 107° C.

Example 16

Synthesis of 2-{[bis-(4-fluoro-phenyl)-methyl-silanyl]-methyl}-2,4-dihydro-[1,2,4]triazole-3-thione To an ice-cold solution of 1-{[bis-(4-fluoro-phenyl)methyl-silanyl]-methyl}-1H-[1,2,4]triazole (3.00 g, 9.51 mmol) in 25 mL of THF was added a solution iPrMgCl in THF (2.0 M, 6.0 mL, 12.0 mmol). The solution was warmed to 40° C. and kept at that temperature for 90 min. Then, it was cooled to 0° C. and portionwise treated with sulfur (1.0 g, 31.2 mmol) and stirred for another 60 min at that temperature. The solution was then poured onto 4% HCl (100 mL). The aqueous phase was extracted with TBME (2×30 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless solid (2.90 g, 8.06 mmol, 85% yield).

$^1$H NMR (CDCl$_3$, 500 MHz); δ (ppm)=12.80 (bs, 1H); 7.87 (s, 1H); 7.55 (dd, J=8.0 Hz, J=10.5 Hz, 4H); 7.07 (t, J=10.5 Hz, 4H); 4.20 (s, 2H); 0.74 (s, 3H).

Melting point: 105° C.

Example 17

Synthesis of 2-[2-(2,4-dichloro-phenyl)-pentyl]-2,4-dihydro-[1,2,4]triazole-3-thione To a solution of 1-[2-(2,4-dichloro-phenyl)-pentyl]-1H-[1,2,4]triazole (338 mg, 1.19 mmol) in 2.5 mL of THF was added a solution iPrMgCl in THF (2.0 M, 0.9 mL, 1.8 mmol). The solution was warmed to 40° C. and kept at that temperature for 90 min. Then, it was cooled to 0° C. and portionwise treated with sulfur (83 mg, 2.59 mmol) and stirred for another 60 min at that temperature. The solution was then poured onto 4% HCl (20 mL). The aqueous phase was extracted with TBME (2×20 mL). The combined org. phases were successively washed with water and brine. The crude product was obtained after drying over $Na_2SO_4$ and removal of all volatiles. Purification was accomplished through flash column chromatography on silica (cyclohexane/EtOAc mixtures) to obtain the product as a colorless liquid (225 mg, 0.71 mmol, 60% yield).

$^1$H NMR (CDCl$_3$, 500 MHz): δ (ppm)=13.09 (s, 1H); 7.77 (s, 1H); 7.32 (d, J=2.0 Hz, 1H); 7.29 (d, J=8.5 Hz, 1H); 7.22 (dd, 2.0 Hz, J=8.5 Hz, 1H); 4.42 (dd, J=7.0 Hz, J=13.5 Hz, 1H); 4.31 (dd, J=8.5 Hz, J=13.5 Hz, 1H); 3.97 (pent., J=7.5 Hz, 1H); 1.69 (q, J=7.5 Hz, 2H); 1.20-1.29 (m, 2H); 0.87 (t, J=7.0 Hz, 3H).

Melting point: 104° C.

Example 18

Synthesis of (2RS,3SR)-1-[3-(2-chloro-phenyl)-2-(2,4-difluorophenyl)-oxiranylmethyl-5-thiocyanato-1H-[1,2,4]triazole A solution of (2RS,3SR)-2-[3-(2-chloro-phenyl)-2-(2,4-difluoro-phenyl)-oxiranylmethyl]-[1,2,4]triazole (2.0 g, 5.6 mmol) in 8 mL of THF was slowly treated with a solution of iPrMgCl in THF (2.0 M in THF, 3.4 mL, 6.8 mmol) at a rate to keep the temperature below 40° C. The solution was then stirred at 40 for 60 min and afterwards cooled to 0° C. A suspension of sulfur (0.27 g, 8.39 mmol) in 2 mL of THF was then added portionwise a rate to keep the temperature below 7° C. Stirring was continued for another 60 min at 0° C. Then, cyanogen bromide (0.89 g, 8.39 mmol) was added and the solution was slowly warmed to ambient temperature and stirred at that temperature overnight. To this solution was then added 50 mL of water and 50 mL of TBME. The aqueous phase was extracted with DCM (25 mL). The combined organic phases were washed with water and brine and dried over $Na_2SO_4$. The crude product was obtained after removal of all volatiles under reduced pressure. Purification was accomplished through flash column chromatography on silica (cyclohexane/EtOAc mixtures) to obtain the product as a yellow solid (0.88 g, 2.17 mmol, 39% yield).

$^1$H NMR (CDCl$_3$, 500 MHz): δ (ppm)=7.87 (s, 1H); 7.58-7.62 (m, 1H); 7.48-7.51 (m, 1H); 7.37-7.44 (m, 2H); 7.21-7.28 (m, 1H); 6.81-6.92 (m, 2H); 4.90 (d, J=21.0 Hz, 1H); 4.30 (s, 1H); 4.15 (d, J=21.0 Hz, 1H).

Melting point: 159° C.

Example 19

Synthesis of S-{(2RS,3SR)-1-[3-(2-chloro-phenyl)-2-(2,4-difluorophenyl)-oxiranylmethyl-5-mercapto-1H-[1,2,4]triazole}methanethio-sulfonate A solution of (2RS,3SR)-2-[3-(2-chloro-phenyl)-2-(2,4-difluoro-phenyl-oxiranylmethyl]-[1,2,4]triazole (5.0 g, 14.0 mmol) in 20 mL of THF was slowly treated with a solution of iPrMgCl in THF (2.0 M in THF, 8.5 mL, 17.0 mmol) at a rate to keep the temperature below 40° C. The solution was then stirred at 40° C. for 60 min and afterwards cooled to 0° C. A suspension of sulfur (0.67 g, 21.0 mmol) in 5 mL of THF was then added portionwise a rate to keep the temperature below 7° C. Stirring was continued for another 60 min at 0° C. Then, methanesulfonyl chloride (3.21 g, 28.0 mmol) was added and the solution was slowly warmed to ambient temperature and stirred at that temperature overnight. To this solution was then added 50 mL of water and 50 mL of TBME. The aqueous phase was extracted with TBME (25 mL). The combined organic phases were washed with water and brine and dried over Na$_2$SO$_4$. The crude product was obtained after removal of all volatiles under reduced pressure. Purification was accomplished through flash column chromatography on silica (cyclohexane/EtOAc mixtures) to obtain the product as a colorless liquid (3.50 g, 7.64 mmol, 55% yield).

$^1$H NMR (CDCl$_3$, 500 MHz): δ (ppm)=7.94 (s, 1H); 7.63 (dd, J=1.5 Hz, J=7.5 Hz, 1H); 7.47 (dd, J=1.5 Hz, J=8.0 Hz, 1H); 7.41 (dt, J=1.5 Hz, J=7.5 Hz, 1H); 7.37 (dt, J=2.0 Hz, J=7.5 Hz, 1H); 7.23 (dt, J=6.0 Hz, J=8.0 Hz, 1H); 6.86 (ddd, J=2.0 Hz, J=9.0 Hz, J=11.0 Hz, 1H); 6.80 (dt, J=2.0 Hz, J=9.0 Hz, 1H); 4.88 (d, J=15.0 Hz, 1H); 4.30 (s, 1H); 4.28 (d, J=15.0 Hz, 1H); 3.46 (s, 3H).

The invention claimed is:

1. A process for the preparation of a compound of formula (I)

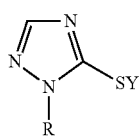

comprising either step (ii) together with (iii-1) or (iii-2); or comprising step (iv):

(ii) reacting a compound of formula (IIIa)

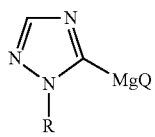

with sulfur, in order to obtain a compound of formula (IIa)

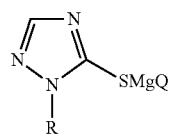

and (iii-1) protonating said compound of formula (IIa), in order to obtain compounds of formula (I), wherein Y is hydrogen; or (iii-2) reacting said compound of formula (IIa) with an electrophilic compound Y$^1$-LG in order to obtain compounds of formula (I), wherein Y is Y$^1$, wherein Y$^1$ is (C$_1$-C$_8$)-alkyl, (C$_1$-C$_8$)-haloalkyl, (C$_2$-C$_8$)-alkenyl, (C$_2$-C$_8$)-haloalkenyl, (C$_2$-C$_8$)-alkynyl, (C$_2$-C$_8$)-haloalkynyl, C(=S)R$^9$, SO$_2$R$^{10}$ or CN; wherein R$^9$ and R$^{10}$ are as defined below; and LG is a leaving group;

or (iv) reacting a compound of formula (IIIa)

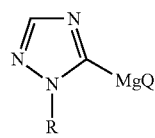

with an electrophile selected from (VI) a disulfide R$^2$—S—S—R$^2$, in order to obtain a compound of formula (I), wherein Y is R$^2$;

(VII) R$^3$—S—SO$_2$—R$^3$, in order to obtain a compound of formula (I), wherein Y is R$^3$; or (VIII) R$^4$—S-Hal, wherein Hal is halogen, in order to obtain a compound of formula (I), wherein Y is R$^4$;

wherein

R is an organic group;

Q is R$^1$ or X, wherein X is halogen; and

Y is hydrogen, halogen, (C$_1$-C$_8$)-alkyl, (C$_1$-C$_8$)-haloalkyl, (C$_2$-C$_8$)-alkenyl, (C$_2$-C$_8$)-haloalkenyl, (C$_2$-C$_8$)-alkynyl, (C$_2$-C$_8$)-haloalkynyl, (C$_6$-C$_{10}$)-aryl, a five-, six-, seven-, eight-, nine- or ten-membered aromatic heterocycle that contains one, two, three or four heteroatoms selected from the group consisting of O, N and S, C(=S)R$^9$, SO$_2$R$^{10}$ or CN; wherein R$^9$ is NA$^3$A$^4$; wherein A$^3$,A$^4$ independently of one another are hydrogen, C$_1$-C$_8$-alkyl, C$_1$-C$_8$-haloalkyl, C$_2$-C$_8$-alkenyl, C$_2$-C$_8$-haloalkenyl, C$_2$-C$_8$-alkynyl, C$_2$-C$_8$-haloalkynyl, C$_3$-C$_8$-cycloalkyl, C$_3$-C$_8$-halocycloalkyl, C$_3$-C$_8$-cycloalkenyl, C$_3$-C$_8$-halocycloalkenyl, $(C_6-C_{10})$-aryl, a five-, six-, seven-, eight-, nine- or ten-membered aromatic heterocycle that contains one, two, three or four heteroatoms from the group consisting of O, N and S;

$R^{10}$ is $(C_1-C_8)$-alkyl, phenyl-$(C_1-C_8)$-alkyl or phenyl, where the phenyl groups are in each case unsubstituted or substituted by one, two or three groups independently selected from the group consisting of halogen and $(C_1-C_4)$-alkyl;

$R^2$, $R^3$ are independently from another $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms from the group consisting of O, N and S, $C(=S)R^9$ or CN; and $R^4$ is halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl or a five-, six-, seven-, eight-, nine- or ten-membered aromatic heterocycle that contains one, two, three or four heteroatoms from the group consisting of O, N and S, or CN.

2. The process of claim 1, wherein said compound (IIIa) is prepared by a process comprising
(i) reacting a compound of formula (IV)

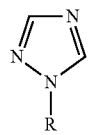

(IV)

with a Grignard reagent $R^1MgQ$ (V), wherein:
R is an organic group;
Q is $R^1$ or X, wherein X is halogen; and
$R^1$ is $(C_1-C_{10})$-alkyl, $(C_2-C_{10})$-alkenyl, $(C_2-C_{10})$-alkynyl, $(C_3-C_8)$-cycloalkyl or $(C_6-C_{10})$-aryl, wherein the aryl is unsubstituted or substituted by one, two or three groups independently selected from the group consisting of halogen and $(C_1-C_4)$-alkyl.

3. A process for the preparation of a compound of formula (I)

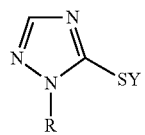

(I)

comprising either step (i) together with step (ii) and (iii-1); step (i) together with step (ii) and step (iii-2); or step (i) together with (iv):
(i) reacting a compound of formula (IV)

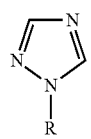

(IV)

with a Grignard reagent $R^1MgQ$ (V), wherein
R is an organic group;
Q is $R^1$ or X, wherein X is halogen; and
$R^1$ is $(C_1-C_{10})$-alkyl, $(C_2-C_{10})$-alkenyl, $(C_2-C_{10})$-alkynyl, $(C_3-C_8)$-cycloalkyl or $(C_6-C_{10})$-aryl, wherein the aryl is unsubstituted or substituted by one, two or three groups independently selected from the group consisting of halogen and $(C_1-C_4)$-alkyl;

(ii) reacting the reaction mixture resulting from step (i) with sulfur; and (iii-1) reacting the product of step (ii) with a protonating agent, in order to obtain compounds of formula (I), wherein Y is hydrogen; or (iii-2) reacting the product of step (ii) with an electrophilic compound $Y^1$-LG in order to obtain compounds of formula (I), wherein Y is $Y^1$, wherein $Y^1$ and LG is a leaving group;

or (iv) reacting the reaction mixture resulting from step (i) with an electrophile selected from
(VI) a disulfide $R^2$—S—S—$R^2$, in order to obtain a compound of formula (I),
wherein Y is $R^2$;
(VII) $R^3$—S—$SO_2$—$R^3$, in order to obtain a compound of formula (I),
wherein Y is $R^3$; or
(VIII) $R^4$—S-Hal, wherein Hal is halogen, in order to obtain a compound of formula (I), wherein Y is $R^4$;

wherein
R is an organic group;
Q is $R^1$ or X, wherein X is halogen; and
Y is hydrogen, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms selected from the group consisting of O, N and S, $C(=S)R^9$, $SO_2R^{10}$ or CN; wherein $R^9$ is $NA^3A^4$; wherein $A^3$, $A^4$ independently of one another are hydrogen, $C_1-C_8$-alkyl, $C_1-C_8$-haloalkyl, $C_2-C_8$-alkenyl, $C_2-C_8$-haloalkenyl, $C_2-C_8$-alkynyl, $C_2-C_8$-haloalkynyl, $C_3-C_8$-cycloalkyl, $C_3-C_8$-halocycloalkyl, $C_3-C_8$-cycloalkenyl, $C_3-C_8$-halocycloalkenyl, $(C_6-C_{10})$-aryl, a five-, six-, seven-, eight-, nine- or ten-membered aromatic heterocycle that contains one, two, three or four heteroatoms from the group consisting of O, N and S;

$R^{10}$ is $(C_1-C_8)$-alkyl, phenyl-$(C_1-C_8)$-alkyl or phenyl, where the phenyl groups are in each case unsubstituted or substituted by one, two or three groups independently selected from the group consisting of halogen and $(C_1-C_4)$-alkyl;

$R^2$, $R^3$ are independently from another $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl, a five-, six-, seven-, eight-, nine- or ten-membered aromatic heterocycle that contains one, two, three or four heteroatoms from the group consisting of O, N and S, $C(=S)R^9$ or CN; and $R^4$ is halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_6-C_{10})$-aryl or a five-, six-, seven-, eight-, nine- or ten-membered aromatic heterocycle that contains one, two, three or four heteroatoms from the group consisting of O, N and S, or CN.

4. The process of claim 3, wherein LiCl is either added to the reaction mixture of step (i) or the Grignard reagent (V) is brought together with LiCl before contacting the same with a compound of formula (IV), thereby forming an addition product $R^1MgX\cdot LiCl((V)\cdot LiCl)$, which is then used in step (i).

5. The process of claim 2, wherein the reaction is carried out as a one-pot reaction.

6. The process of claim 3, wherein R is a group (1):

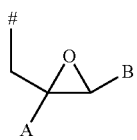
(1)

wherein # shall mean the point of attachment to the triazolo group, and A and B are as defined as follows:

A or B is a three-, four-, five-, six-, seven-, eight-, nine- or ten-membered saturated or partially unsaturated heterocycle or five-, six-, seven-, eight-, nine- or ten-membered aromatic heterocycle, where the heterocycle contains in each case one, two, three or four heteroatoms selected from the group consisting of O, N and S; or is naphthyl or phenyl;

and the respective other variable B or A has one of the meanings mentioned above for A or B or is $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, naphthyl or benzodioxolyl;

where A and/or B independently of one another are unsubstituted or substituted by one, two, three or four independently selected substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$, $A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino.

7. The process of claim 3, wherein R is a group (2):

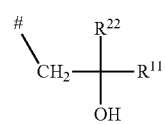
(2)

wherein # shall mean the point of attachment to the triazolo group and $R^{11}$ and $R^{22}$ have the following meanings:

$R^{11}$, $R^{22}$ independently of one another are $C_1$-$C_6$-alkyl, $C_1$-$C_6$-haloalkyl, $C_3$-$C_6$-cycloalkyl, $C_3$-$C_6$-halocycloalkyl or phenyl, wherein the alkyl, cycloalkyl and phenyl moieties may be unsubstituted or substituted by one, two, three or four substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$, $A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

or $R^{11}$ and $R^{22}$, together with the carbon atom to which they are attached, form a five- or six-membered saturated or partially unsaturated ring, that can be unsubstituted or substituted by one, two, three, four or five substituents L', wherein L' stands for L wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5, A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

or L' stands for a group

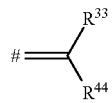

wherein $R^{33}$ and $R^{44}$ independently are selected from the group of hydrogen and L.

8. The process of claim 3, wherein R is a group (4):

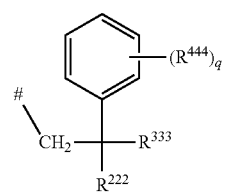

(4)

wherein # shall mean the point of attachment to the triazolo group and $R^{222}$, $R^{333}$ and $R^{444}$ have the following meanings:

$R^{222}$ and $R^{333}$ are independently selected from hydrogen, cyano, $C_1$-$C_6$-alkyl and $C_1$-$C_6$-haloalkyl, wherein the alkyl moieties may be unsubstituted or substituted by one, two, three or four substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$alkyl, $C_1$-$C_6$-alkylene, oxy-$C_2$-$C_4$-alkylene, oxy-$C_1$-$C_3$-alkyleneoxy, $C_1$-$C_8$-alkenyloximino-$C_1$-$C_8$-alkyl, $C_2$-$C_8$-alkynyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5, A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

q is one, two, three, or five; and $R^{444}$ are independently selected from L.

9. The process of claim 3, wherein R is a group (1):

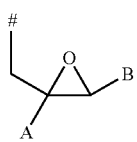

(1)

wherein # shall mean the point of attachment to the triazolo group, and A and B are as defined as follows:

A or B is a three-, four-, five-, six-, seven-, eight-, nine- or ten-membered saturated or partially unsaturated heterocycle or five-, six-, seven-, eight-, nine- or ten-membered aromatic heterocycle, where the heterocycle contains in each case one, two, three or four heteroatoms selected from the group consisting of O, N and S; or is naphthyl or phenyl;

and the respective other variable B or A has one of the meanings mentioned above for A or B or is $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, naphthyl or benzodioxolyl;

where A and/or B independently of one another are unsubstituted or substituted by one, two, three or four independently selected substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$, $A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino.

10. The process of claim 3, wherein R is a group (2):

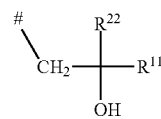

(2)

wherein # shall mean the point of attachment to the triazolo group and $R^{11}$ and $R^{22}$ have the following meanings:

$R^{11}$, $R^{22}$ independently of one another are $C_1$-$C_6$-alkyl, $C_1$-$C_6$-haloalkyl, $C_3$-$C_6$-cycloalkyl, $C_3$-$C_6$-halocycloalkyl or phenyl, wherein the alkyl, cycloalkyl and phenyl moieties may be unsubstituted or substituted by one, two, three or four substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$, $A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

or $R^{11}$ and $R^{22}$, together with the carbon atom to which they are attached, form a five- or six-membered saturated or partially unsaturated ring, that can be unsubstituted or substituted by one, two, three, four or five substituents L', wherein L' stands for L wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, S(=O)$_n$A$^1$, C(=O)A$^2$, C(=S)A$^2$, NA$^3$A$^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, A$^1$, A$^2$, A$^5$, A$^6$ are as defined below:

n is 0, 1 or 2;

A$^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, A$^2$ is one of the groups mentioned for A$^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

A$^5$, A$^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups R$^L$:

R$^L$ is halogen, cyano, nitro, $C_1$-$C_8$-alkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

or L' stands for a group

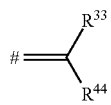

wherein R$^{33}$ and R$^{44}$ independently are selected from the group of hydrogen and L.

11. The process of claim 3, wherein R is a group (4):

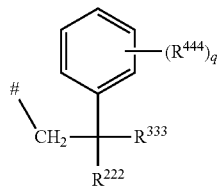

(4)

wherein # shall mean the point of attachment to the triazolo group and R$^{222}$, R$^{333}$ and R$^{444}$ have the following meanings:

R$^{222}$ and R$^{333}$ are independently selected from hydrogen, cyano, $C_1$-$C_6$-alkyl and $C_1$-$C_6$-haloalkyl, wherein the alkyl moieties may be unsubstituted or substituted by one, two, three or four substituents L; wherein L is halogen, cyano, nitro, cyanato (OCN), $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, S(=O)$_n$A$^1$, C(=O)A$^2$, C(=S)A$^2$, NA$^3$A$^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, A$^1$, A$^2$, A$^5$, A$^6$ are as defined below:

n is 0, 1 or 2;

A$^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, A$^2$ is one of the groups mentioned for A$^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

A$^5$, A$^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups R$^L$:

R$^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

q is one, two, three, or five; and

R$^{444}$ are independently selected from L.

12. The process of claim 3, wherein R is a group (1):

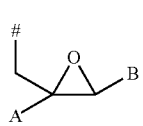

(1)

wherein # shall mean the point of attachment to the triazolo group, and A and B are as defined as follows:

A or B is a three-, four-, five-, six-, seven-, eight-, nine- or ten-membered saturated or partially unsaturated heterocycle or five-, six-, seven-, eight-, nine- or ten-membered aromatic heterocycle, where the heterocycle contains in each case one, two, three or four heteroatoms selected from the group consisting of O, N and S; or is naphthyl or phenyl;

and the respective other variable B or A has one of the meanings mentioned above for A or B or is $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, naphthyl or benzodioxolyl;

where A and/or B independently of one another are unsubstituted or substituted by one, two, three or four independently selected substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$alkyl, $C_1$-$C_8$-haloalkyl, amino, $C_1$-$C_8$alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$,$A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$alkylcarbonyloxy, $C_1$-$C_8$-alkoxycarbonyl, amino, $C_1$-$C_8$-alkylamino, di-$C_1$-$C_8$-alkylamino.

13. The process of claim 3, wherein R is a group (2):

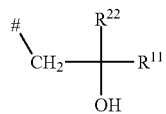

(2)

wherein # shall mean the point of attachment to the triazolo group and $R^{11}$ and $R^{22}$ have the following meanings:

$R^{11}$, $R^{22}$ independently of one another are $C_1$-$C_6$-alkyl, $C_1$-$C_6$-haloalkyl, $C_3$-$C_6$-cycloalkyl, $C_3$-$C_6$-halocycloalkyl or phenyl, wherein the alkyl, cycloalkyl and phenyl moieties may be unsubstituted or substituted by one, two, three or four substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1$, $A^2$, $A^5$, $A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5$,$A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$alkoxycarbonyl, amino, $C_1$-$C_8$-alkylamino, di-$C_1$-$C_8$-alkylamino;

or $R^{11}$ and $R^{22}$, together with the carbon atom to which they are attached, form a five- or six-membered saturated or partially unsaturated ring, that can be unsubstituted or substituted by one, two, three, four or five substituents L', wherein L' stands for L wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_1$-$C_8$-alkoximino-$C_1$-$C_8$-alkyl, $C_2$-$C_8$-alkenyloximino-$C_1$-$C_8$-alkyl, $C_2$-$C_8$-alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1, A^2, A^5, A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5,A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

or L' stands for a group

wherein $R^{33}$ and $R^{44}$ independently are selected from the group of hydrogen and L.

14. The process of claim 3, wherein R is a group (4):

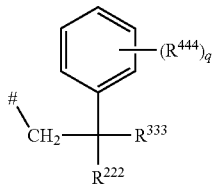

(4)

wherein # shall mean the point of attachment to the triazolo group and $R^{222}, R^{333}$ and $R^{444}$ have the following meanings:

$R^{222}$ and $R^{333}$ are independently selected from hydrogen, cyano, $C_1$-$C_6$-alkyl and $C_1$-$C_6$-haloalkyl, wherein the alkyl moieties may be unsubstituted or substituted by one, two, three or four substituents L; wherein L is halogen, cyano, nitro, cyanato (OCN), $C_1$-$C_8$-alkyl, $C_1$-$C_8$-haloalkyl, phenyl-$C_1$-$C_6$-alkyloxy, $C_2$-$C_8$-alkenyl, $C_2$-$C_8$-haloalkenyl, $C_2$-$C_8$-alkynyl, $C_2$-$C_8$-haloalkynyl, $C_4$-$C_{10}$-alkadienyl, $C_4$-$C_{10}$-haloalkadienyl, $C_1$-$C_8$-alkoxy, $C_1$-$C_8$-haloalkoxy, $C_1$-$C_8$-alkylcarbonyloxy, $C_1$-$C_8$-alkylsulfonyloxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkenyl, $C_3$-$C_8$-halocycloalkenyl, $C_3$-$C_8$-cycloalkoxy, $C_3$-$C_6$-cycloalkenyloxy, hydroxyimino-$C_1$-$C_8$-alkyl, $C_1$-$C_6$-alkylene, oxy-$C_2$-$C_4$-alkylene, oxy-$C_1$-$C_3$-alkyleneoxy, $C_2$-$C_8$-alkenyloximino-$C_1$-$C_8$-alkyl, $C_2$-$C_8$alkynyloximino-$C_1$-$C_8$-alkyl, $S(=O)_nA^1$, $C(=O)A^2$, $C(=S)A^2$, $NA^3A^4$, phenyl-$C_1$-$C_8$-alkyl, phenyl, phenyloxy or a five- or six-membered saturated, partially unsaturated or aromatic heterocycle which contains one, two, three or four heteroatoms selected from the group consisting of O, N and S; where n, $A^1, A^2, A^5, A^6$ are as defined below:

n is 0, 1 or 2;

$A^1$ is hydrogen, hydroxyl, $C_1$-$C_8$-alkyl, $C_1$-$C_8$-haloalkyl, amino, $C_1$-$C_8$-alkylamino or di-$C_1$-$C_8$-alkylamino, $A^2$ is one of the groups mentioned for $A^1$ or $C_2$-$C_8$-alkenyl, $C_2$-$C_8$-haloalkenyl, $C_2$-$C_8$-alkynyl, $C_2$-$C_8$-haloalkynyl, $C_1$-$C_8$-alkoxy, $C_1$-$C_8$-haloalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_3$-$C_8$-cycloalkyl, $C_3$-$C_8$-halocycloalkyl, $C_3$-$C_8$-cycloalkoxy or $C_3$-$C_8$-halocycloalkoxy;

$A^5,A^6$ independently of one another are hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_3$-$C_8$-halocycloalkyl, $C_3$-$C_8$-cycloalkenyl or $C_3$-$C_8$-halocycloalkenyl;

where the aliphatic and/or alicyclic and/or aromatic groups of the radical definitions of L for their part may carry one, two, three or four identical or different groups $R^L$:

$R^L$ is halogen, cyano, nitro, $C_1$-$C_8$-alkyl, $C_1$-$C_8$-haloalkyl, $C_1$-$C_8$-alkoxy, $C_1$-$C_8$-haloalkoxy, $C_3$-$C_8$-cycloalkyl, $C_3$-$C_8$-halocycloalkyl, $C_3$-$C_8$-cycloalkenyl, $C_3$-$C_8$-cycloalkoxy, $C_3$-$C_8$-halocycloalkoxy, $C_1$-$C_8$-alkylcarbonyl, $C_1$-$C_8$-alkylcarbonyloxy, $C_1$-$C_8$-alkoxycarbonyl, amino, $C_1$-$C_8$-alkylamino, di-$C_1$-$C_8$-alkylamino;

q is one, two, three, or five; and $R^{444}$ are independently selected from L.

15. The process of claim 3, wherein the reaction is carried out as a one-pot reaction.

* * * * *